United States Patent
D'Lima et al.

(10) Patent No.: US 11,497,830 B2
(45) Date of Patent: Nov. 15, 2022

(54) ELECTROSPINNING OF CARTILAGE AND MENISCUS MATRIX POLYMERS

(71) Applicant: Scripps Health, San Diego, CA (US)

(72) Inventors: Darryl D. D'Lima, San Diego, CA (US); Shawn Grogan, Mission Viejo, CA (US); Clifford W. Colwell, Jr., La Jolla, CA (US); Jihye Baek, San Diego, CA (US)

(73) Assignee: SCRIPPS HEALTH, San Diego, CA (US)

( * ) Notice: Subject to any disclaimer, the term of this patent is extended or adjusted under 35 U.S.C. 154(b) by 0 days.

(21) Appl. No.: 15/125,749

(22) PCT Filed: Mar. 13, 2015

(86) PCT No.: PCT/US2015/020553
§ 371 (c)(1),
(2) Date: Sep. 13, 2016

(87) PCT Pub. No.: WO2015/138970
PCT Pub. Date: Sep. 17, 2015

(65) Prior Publication Data
US 2017/0007741 A1    Jan. 12, 2017

Related U.S. Application Data

(60) Provisional application No. 61/955,082, filed on Mar. 18, 2014, provisional application No. 61/953,550, filed on Mar. 14, 2014.

(51) Int. Cl.
| | |
|---|---|
| A61F 2/38 | (2006.01) |
| A61L 27/26 | (2006.01) |
| A61F 2/30 | (2006.01) |
| A61L 27/20 | (2006.01) |
| A61L 27/24 | (2006.01) |
| A61L 27/54 | (2006.01) |
| A61L 27/52 | (2006.01) |
| A61L 27/50 | (2006.01) |
| A61L 27/38 | (2006.01) |
| A61L 27/18 | (2006.01) |
| A61L 27/58 | (2006.01) |
| D01D 5/00 | (2006.01) |
| D01D 5/34 | (2006.01) |
| A61F 2/44 | (2006.01) |

(52) U.S. Cl.
CPC ............ *A61L 27/26* (2013.01); *A61F 2/3094* (2013.01); *A61F 2/30756* (2013.01); *A61F 2/3872* (2013.01); *A61L 27/18* (2013.01); *A61L 27/20* (2013.01); *A61L 27/24* (2013.01); *A61L 27/3817* (2013.01); *A61L 27/3826* (2013.01); *A61L 27/3834* (2013.01); *A61L 27/50* (2013.01); *A61L 27/52* (2013.01); *A61L 27/54* (2013.01); *A61L 27/58* (2013.01); *D01D 5/0038* (2013.01); *D01D 5/34* (2013.01); *A61F 2002/4495* (2013.01); *A61F 2210/0004* (2013.01); *A61L 2300/414* (2013.01); *A61L 2430/06* (2013.01); *D10B 2331/041* (2013.01); *D10B 2401/12* (2013.01); *D10B 2509/00* (2013.01)

(58) Field of Classification Search
None
See application file for complete search history.

(56) References Cited

U.S. PATENT DOCUMENTS

| | | | |
|---|---|---|---|
| 4,689,186 | A | 8/1987 | Bornat |
| 5,526,027 | A | 6/1996 | Wade et al. |
| 2002/0177903 | A1 | 11/2002 | Geistlich et al. |
| 2003/0100824 | A1 | 5/2003 | Warren et al. |
| 2003/0175410 | A1 | 9/2003 | Campbell et al. |
| 2003/0207638 | A1 | 11/2003 | Bowlin et al. |
| 2004/0237822 | A1 | 12/2004 | Boland et al. |
| 2008/0038352 | A1 | 2/2008 | Simpson et al. |
| 2009/0074832 | A1 | 3/2009 | Zussman et al. |
| 2009/0117087 | A1 | 5/2009 | Carroll et al. |
| 2009/0202616 | A1 | 8/2009 | Chong et al. |
| 2009/0239302 | A1 | 9/2009 | Decher et al. |
| 2010/0129450 | A1 | 5/2010 | Atala et al. |
| 2010/0178274 | A1 | 7/2010 | Sekiya et al. |
| 2010/0236481 | A1 | 9/2010 | O'Brien et al. |
| 2010/0331980 | A1 | 12/2010 | Lee et al. |

(Continued)

FOREIGN PATENT DOCUMENTS

| | | |
|---|---|---|
| EP | 1027989 A2 | 8/2000 |
| EP | 1232863 A1 | 8/2002 |

(Continued)

OTHER PUBLICATIONS

Zhang (Biomacromolecules 2005, 6, 2583-2589).*
Chiu (J. Biomed. Mater. Res., 83A: 1117-1127, Jun. 25, 2007).*
Brinkman (Biomacromolecules 2003, 4, 890-895).*
Gupta (Macromolecules 2004, 37, 9211-9218).*
Haslauer (Journal of Biomaterials Science 22 (2011) 1695-1712).*
Sahoo (Biotechnol. Bioeng., 106: 690-698, Mar. 12, 2010).*
Bartolovic (Analyst, 2010, 135, 157-164).*
Li (Materials Letters 79 (2012) 245-247).*
Srouji (J Mater Sci: Mater Med (2008) 19:1249-1255).*

(Continued)

*Primary Examiner* — David J Blanchard
*Assistant Examiner* — Daniel F Coughlin
(74) *Attorney, Agent, or Firm* — Wilson Sonsini Goodrich & Rosati

(57) ABSTRACT

Disclosed herein are methods of producing a cartilaginous implant by producing a polymer scaffold composition by electrospinning a polymer solution onto a collector in order to obtain polymer fibers; crosslinking the polymer fibers; and adding a plurality of cells to the polymer scaffold composition, wherein the plurality of cells comprises cartilaginous cells to form a cartilaginous implant.

24 Claims, 30 Drawing Sheets

(56) References Cited

U.S. PATENT DOCUMENTS

| | | | |
|---|---|---|---|
| 2011/0098826 A1* | 4/2011 | Mauck | A61F 2/442 623/23.72 |
| 2011/0234668 A1 | 9/2011 | Hoisington et al. | |
| 2012/0089238 A1 | 4/2012 | Kang et al. | |
| 2014/0051169 A1 | 2/2014 | Ganey et al. | |
| 2014/0277572 A1* | 9/2014 | Martin | A61L 27/56 623/23.58 |
| 2015/0250927 A1 | 9/2015 | Macewan | |
| 2015/0351896 A1 | 12/2015 | D'Lima et al. | |

FOREIGN PATENT DOCUMENTS

| | | | |
|---|---|---|---|
| EP | 2343415 A2 | | 7/2011 |
| EP | 2458044 A1 | | 5/2012 |
| GB | 2343415 A | | 5/2000 |
| JP | S55057060 A | | 4/1980 |
| JP | 2002254654 A | | 9/2002 |
| JP | 2003180815 A | | 7/2003 |
| JP | 2004513698 A | | 5/2004 |
| JP | 2004216119 A | | 8/2004 |
| JP | 2004523484 A | | 8/2004 |
| JP | 2004254655 A | | 9/2004 |
| JP | 2005278909 A | | 10/2005 |
| JP | 2006051157 A | | 2/2006 |
| JP | 2006122147 A | | 5/2006 |
| JP | 2008514341 A | | 5/2008 |
| JP | 2009039401 A | | 2/2009 |
| JP | 2010501547 A | | 1/2010 |
| JP | 2011255513 A | | 12/2011 |
| JP | 2013512660 A | | 4/2013 |
| JP | 2013523227 A | | 6/2013 |
| JP | 2014514942 A | | 6/2014 |
| JP | 2015535893 A | | 12/2015 |
| JP | 2016519222 A | | 6/2016 |
| WO | WO-03028782 A1 | | 4/2003 |
| WO | WO-2004087012 A1 | | 10/2004 |
| WO | WO2005023324 | * | 3/2005 |
| WO | WO-2007102606 A1 | | 9/2007 |
| WO | WO-2012113812 A1 | | 8/2012 |
| WO | WO-2012136701 A1 | | 10/2012 |
| WO | WO-2013093921 A1 | | 6/2013 |
| WO | WO-2014110590 A1 | | 7/2014 |
| WO | WO-2015138970 A1 | | 9/2015 |

OTHER PUBLICATIONS

Li2 (International Journal of Biological Macromolecules 61 (2013) 69-74).*
Stankus (Biomaterials 28 (2007) 2738-2746).*
Shields (Tissue engineering. Sep. 1, 2004;10(9-10):1510-7).*
Kim (Macromol. Biosci. 2010, 10, 91-100).*
Torricelli (Materials Science and Engineering: C, vol. 36, Mar. 1, 2014, pp. 130-138).*
Zhao (Journal of Biomedical Materials Research Part A, 83(2), 372-382, 2007).*
Lee (Biomaterials 29 (2008) 2891-2898).*
Cui et al. Accelerated myotube formation using bioprinting technology for biosensor applications. Biotechnol Lett 35(3):315-321 (2013).
Cui et al. Direct Human Cartilage Repair Using Three-Dimensional Bioprinting Technology. Tissue Engineering Part A 18(11-12):1304-1312 (2012).
Cui et al. Synergistic Action of Fibroblast Growth Factor-2 and Transforming Growth Factor-beta1 Enhances Bioprinted Human Neocartilage Formation. Biotechnol. Bioeng. 109(9):2357-2368 (2012).
Cui et al. Thermal Inkjet Printing in Tissue Engineering and regenerative Medicine. Recent Pat Drug Deliv. Formul. 6(2):149-155 (2012).
Grogan et al. In vitro model for the study of necrosis and apoptosis in native cartilage. J. Pathol. 198:5-13 (2002).
Grogan et al. Mesenchymal progenitor cell markers in human articular cartilage: normal distribution and changes in osteoarthritis. Arthritis Res. Ther. 11:R85 (2009).
Gruene et al. Laser printing of stem cells for biofabrication of scaffold-free autologous grafts. Tissue Engineering: Part C Methods 17(1):79-89 (2011).
Li. Electrospinning of Core-Shell Collagen Nanofibers. Western Graduate & Postdoctoral Studies University of Western Ontario—Electronic Thesis (2013) (126 pgs.).
Martin et al. Quantitative analysis of gene expression in human articular cartilage from normal and osteoarthritic joints. Osteoarthritis Cartilage 9(2):112-118 2001.
Matsusaki et al. Three-dimensional human tissue chips fabricated by rapid and automatic inkjet cell printing. Adv. Healthcare Mater. 2(4):534-539 (2013).
Pauli et al. Macroscopic and histopathologic analysis of human knee menisci in aging and osteoarthritis. Osteoarthritis Cartilage 19(9):1132-1141 (2011).
PCT/US2014/011525 International Preliminary Report on Patentability dated Jul. 23, 2015.
PCT/US2014/011525 International Search Report and Written Opinion dated May 13, 2014.
PCT/US2015/020553 International Preliminary Report on Patentability dated Sep. 22, 2016.
PCT/US2015/020553 International Search Report and Written Opinion dated Jun. 8, 2015.
Pescosolido et al. Hyaluronic acid and dextran-based semi-IPN hydrogels as biomaterials for bioprinting. Biomacromolecules 12(5):1831-1838 (2011).
Roberts et al. Immunohistochemical study of collagen types I and II and procollagen IIA in human cartilage repair tissue following autologous chondrocyte implantation. Knee 16:398-404 (2009).
Schuurman et al. Bioprinting of hybrid tissue constructs with tailorable mechanical properties. Biofabrication 3(2):021001 (7 pgs.) (2011).
Song et al. Sodium alginate hydrogel-based bioprinting using a novel multinozzle bioprinting system. Artif. Org. 35(11):1132-1136 (2011).
Xu et al. Hybrid printing of mechanically and biologically improved constructs for cartilage tissue engineering applications. Biofabrication 5(1):015001 (10 pgs.) (2012).
Yamaguchi et al. Cell patterning through inkjet printing of one cell per droplet. Biofabrication 4(4):045005 (8 pgs.) (2012).
Yan et al. Laser-assisted printing of alginate long tubes and annular constructs. Biofabrication 5(1):015002 (8 pgs.) (2013).
Tsuda. Hone Kyushu Yokuseiyaku Koho to shite no Hakotsu Saibo Keisei Yokusei Inshi OCIF/OPG, Ko-RANKL Kotai, Oyobi sono Hoka no RANKL/RANK System Modulator J. Jpn Orthop Assoc. 78(8):1-P3-5 (2005) (w/English translation).
U.S. Appl. No. 14/759,398 Office Action dated Nov. 2, 2017.
Li. Electrospinning of Core-shell Collagen Nanofibers. Thesis. Western University Graduate & Postdoctoral Studies (126 pgs) (2013).
U.S. Appl. No. 14/759,398 Office Action dated Mar. 22, 2019.
Xu et al. Experimental and modeling study of collagen scaffolds with the effects of crosslinking and fiber alignment. Int J Biomater 2011:172389 (2011).
Liu et al. Photochemical crosslinked electrospun collagen nanofibers: synthesis, characterization and neural stem cell interactions. J Biomed Mater Res A 95:276-282 (2010).
U.S. Appl. No. 14/759,398 Office Action dated Sep. 24, 2019.
Wang et al. Fabrication and characterization of heparin-grafted poly-L-lactic acid-chitosan core-shell nanofibers scaffold for vascular gasket. ACS Appl Mater Interfaces 5:3757-3763 (2013).
Wu et al. In vivo fast equilibrium microextraction by stable and biocompatible nanofiber membrane sandwiched in microfluidic device. Anal Chem 85:11524-11531 (2013).
U.S. Appl. No. 14/759,398 Office Action dated Mar. 30, 2020.
Bone and Joint Regeneration Technology. National Institute of Advanced Industrial Science and Technology Today. Available at https://www.aist.go.jp/Portals/0/resource_images/aist_e/research_results/publications/pamphlet/today/b_regeneration_e.pdf (16 pgs) (2006).
U.S. Appl. No. 14/759,398 Office Action dated Aug. 13, 2021.
U.S. Appl. No. 14/759,398 Office Action dated Mar. 16, 2021.

* cited by examiner

FIG. 6A                    FIG. 6B

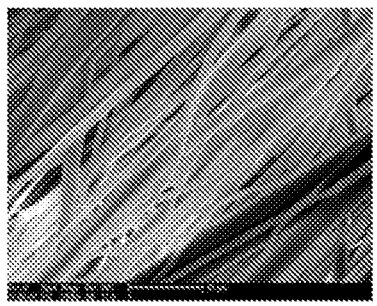  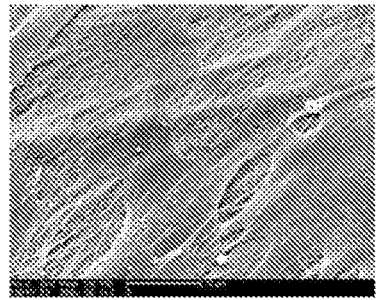
FIG. 13A  FIG. 13B  FIG. 13C
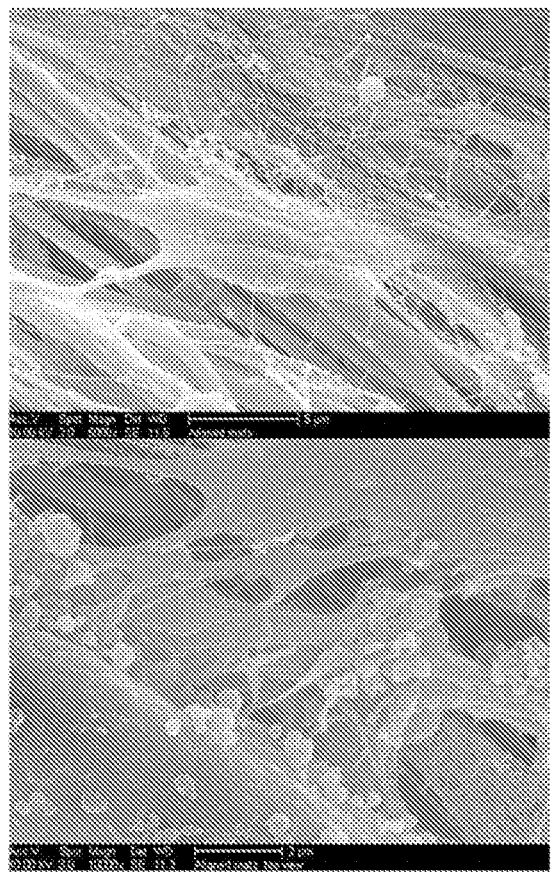 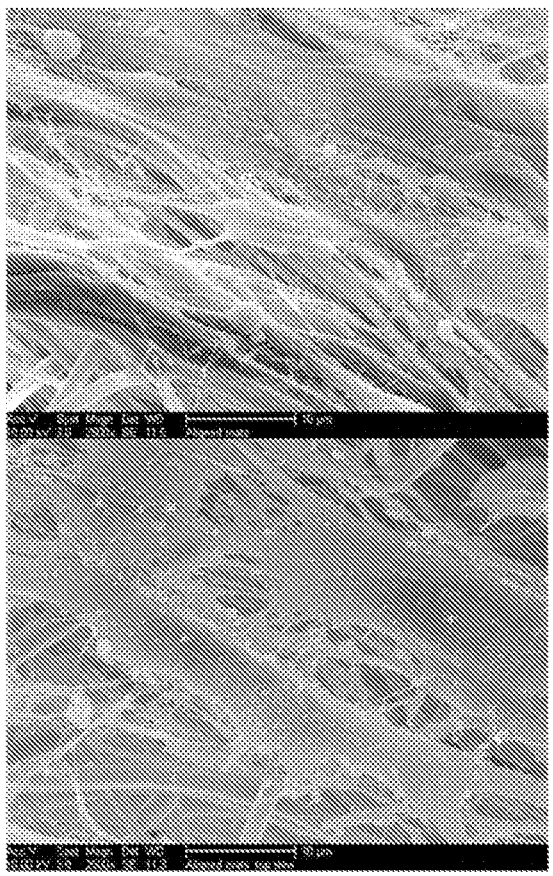
FIG. 14A  FIG. 14B

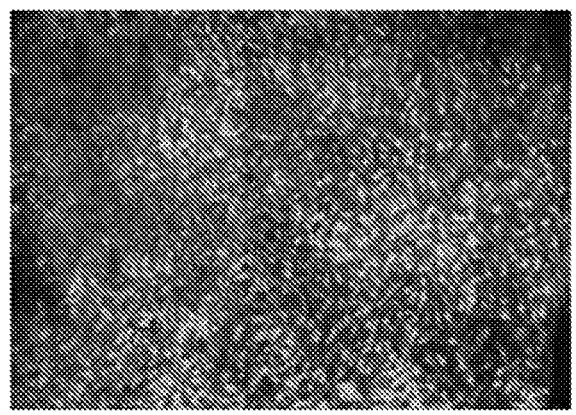
FIG. 17B
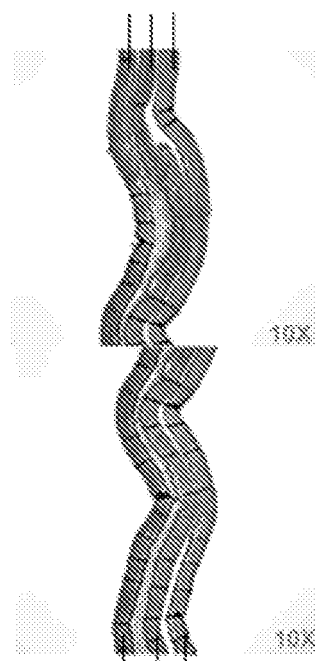
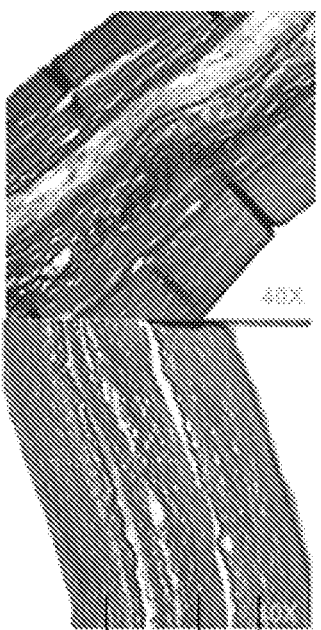
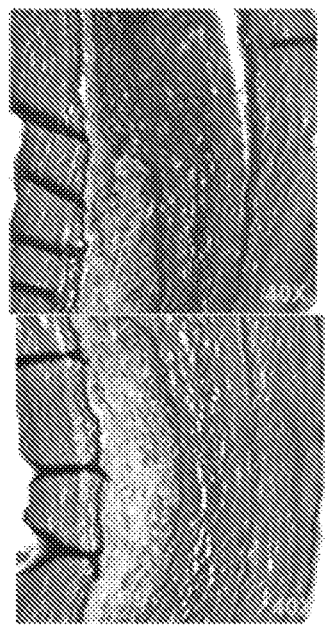
FIG. 18A  FIG. 18B  FIG. 18C

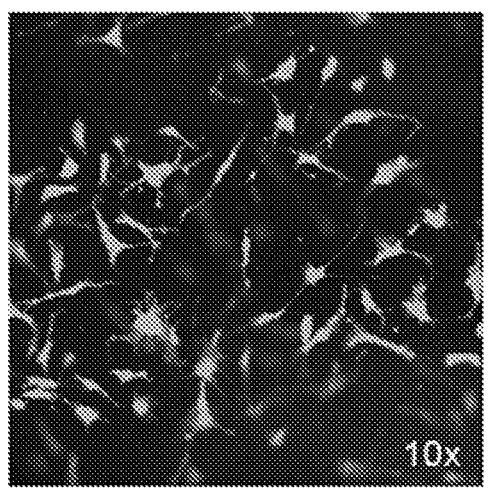
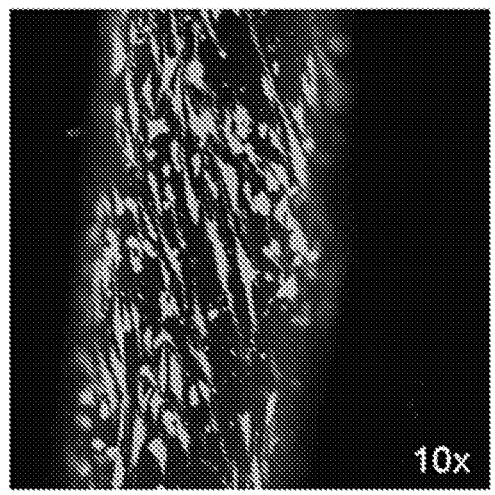
FIG. 20C  FIG. 20D
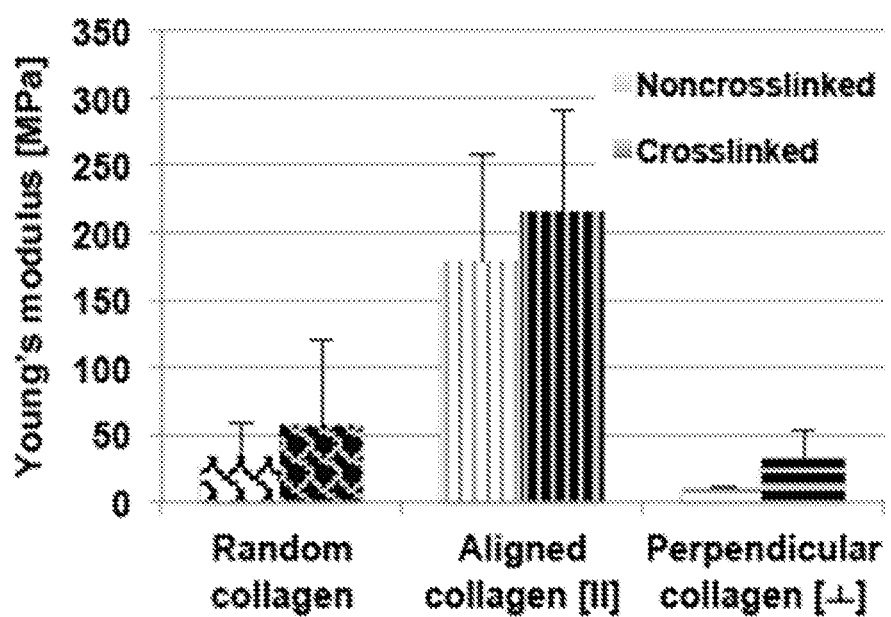
FIG. 21A

FIG. 27A
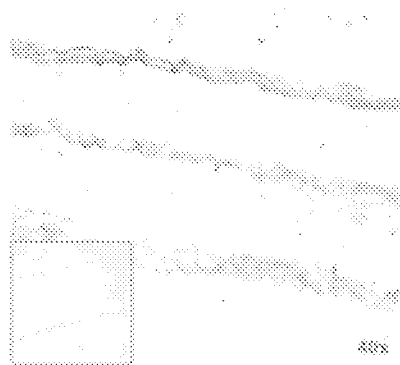
FIG. 27B
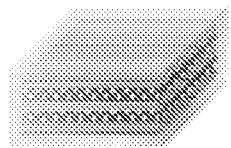
FIG. 27C
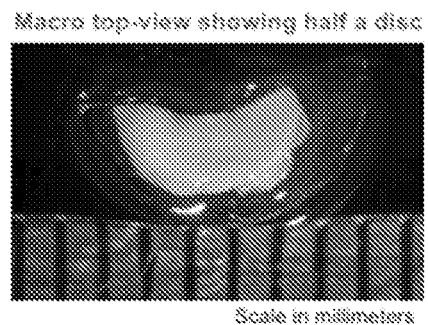
FIG. 28A
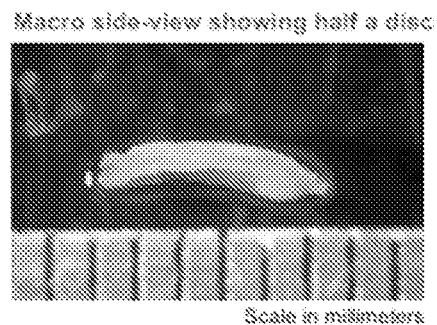
FIG. 28B
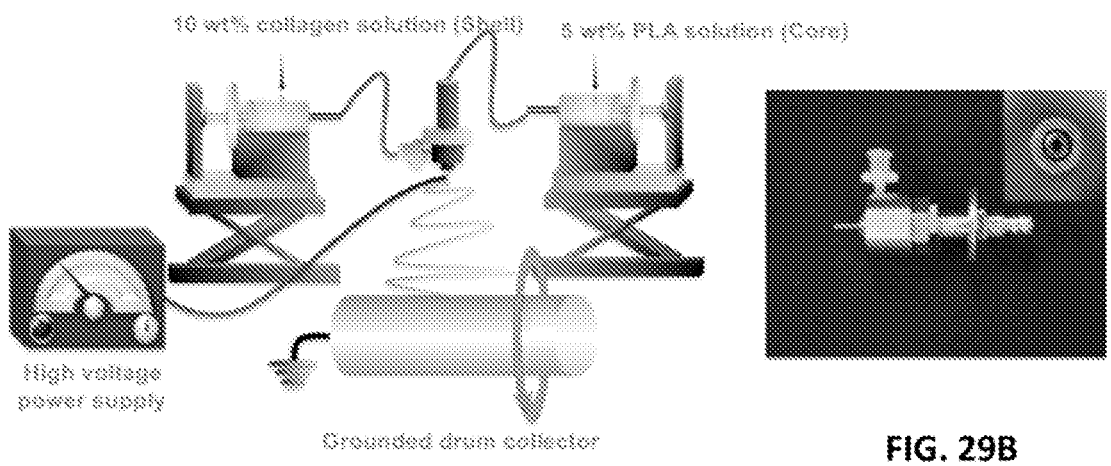
FIG. 29A
FIG. 29B 1 week 2 weeks 1 week 2 weeks

ELECTROSPINNING OF CARTILAGE AND MENISCUS MATRIX POLYMERS

CROSS-REFERENCE

This application is the National Phase entry of International Application No. PCT/US2015/020553, filed Mar. 13, 2015, which claims the benefit of U.S. Provisional Application No. 61/953,550, filed Mar. 14, 2014, and U.S. Provisional Application No. 61/955,082, filed Mar. 18, 2014, all of which are incorporated by reference herein in their entireties.

SUMMARY OF THE INVENTION

Disclosed herein are methods of producing a polymer scaffold composition, comprising: electrospinning a first polymer solution comprising a first polymer and a second polymer solution comprising a second polymer onto a collector to form polymer fibers, the electrospinning comprising: applying a first voltage to a first polymer solution in a first emitter and ejecting the first polymer solution through a first emitter outlet; and applying a second voltage to a second polymer solution in a second emitter and ejecting the second polymer solution through a second emitter outlet, and crosslinking the polymer fibers to produce the polymer scaffold composition. In some embodiments, the first polymer and/or second polymer is selected from the group consisting of polylactic acid, collagen, methacrylated collagen, chitosan, gelatin, latex, dextran, fibroin, keratin, poly(lactic acid-co-glycolic acid), polyglycolic acid, polydiaxanone, poly(propylene carbonate), poly(ethylene oxide), poly(ester-urethane)urea, poly(lactide-co-caprolactone) and combinations thereof. In some embodiments, electrospinning the first polymer solution produces a first plurality of polymer fibers on the collector and wherein the second polymer solution produces a second plurality of polymer fibers on the collector. In some embodiments, electrospinning the first polymer solution and electrospinning the second polymer solution occurs sequentially. In some embodiments, electrospinning the first polymer solution and the second polymer solution occurs simultaneously. In some embodiments, the first emitter outlet comprises a first duct with a first interior and the second emitter outlet comprises a second tube with a second interior, wherein the second tube is within the interior of the first tube and the first tube and the second tube are co-axial. In some embodiments, the first polymer solution encapsulates the second polymer solution as they are ejected from the emitter outlets on to the collector to form the polymer fibers, wherein the polymer fibers have a structure comprising: a shell comprising the first polymer; and a core comprising the second polymer. In some embodiments, the shell consists essentially of the first polymer. In some embodiments, the first polymer is collagen. In some embodiments, the first polymer solution comprises collagen dissolved in a mixed solvent of PBS and ethanol. In some embodiments, the first polymer solution comprises collagen dissolved to a 16% wt solution. In some embodiments, the first polymer solution comprises collagen dissolved in hexafluoro-2-propanol (HFIP). In some embodiments, the first polymer solution comprises collagen dissolved in water. In some embodiments, the collagen is methacrylated collagen and the polymer fibers comprise methacrylated collagen. In some embodiments, the methods further comprise releasing an oxidant from the polymer fibers, resulting in a chemical bond between one or more of the polymer fibers. In some embodiments, releasing the oxidant comprises contacting the polymer scaffold composition with riboflavin. In some embodiments, the methods further comprise contacting the polymer scaffold composition with a photoinitiator. In some embodiments, the methods further comprise exposing the polymer scaffold composition to an ultraviolet light to release the oxidant from the polymer fibers, resulting in a chemical bond between one or more of the polymer fibers. In some embodiments, the second polymer is selected from the group consisting of polylactic acid, collagen, methacrylated collagen, chitosan, gelatin, latex, dextran, fibroin, keratin, poly(lactic acid-co-glycolic acid), polyglycolic acid, polydiaxanone, poly(propylene carbonate), poly(ethylene oxide), poly(ester-urethane)urea, poly(lactide-co-caprolactone) and combination s thereof. In some embodiments, the second polymer is polylactic acid. In some embodiments, the polylactic acid is dissolved in a mixed solvent of dichloromethane and N,N-dimethylacetamide. In some embodiments, the polylactic acid is dissolved to a 10 wt % solution. In some embodiments, the first voltage and/or second voltage is about 15 kV to about 20 kV. In some embodiments, the methods further comprise applying a voltage to the collector. In some embodiments, the voltage is about −10 kV to about −1 kV. In some embodiments, electrospinning and crosslinking occur simultaneously. In some embodiments, crosslinking occurs after electrospinning. In some embodiments, collagen is conjugated to a biotin and the collector comprises avidin. In some embodiments, the methods further comprise contacting the polymer fibers with a plurality of cells to form a cell-seeded polymer scaffold composition. In some embodiments, contacting the polymer fibers with the plurality of cells comprises electrospraying the plurality of cells on to the polymer fibers. In some embodiments, electrospinning the polymer solution and electrospraying the plurality of cells occurs simultaneously. In some embodiments, electrospraying the plurality of cells occurs after electrospinning the polymer solution. In some embodiments, electrospraying the plurality of cells occurs after crosslinking the polymer fibers. In some embodiments, electrospraying the plurality of cells occurs before crosslinking. In some embodiments, electrospraying the plurality of cells and cross-linking the polymer fibers occur simultaneously. In some embodiments, electrospinning the polymer solution, electrospraying the plurality of cells and cross-linking the polymer fibers occurs simultaneously. In some embodiments, the methods comprise encapsulating the plurality of cells in the polymer scaffold composition. In some embodiments, the plurality of cells comprises mesenchymal stem cells, meniscal cells, chondroblasts, chondrocytes or a combination thereof. In some embodiments, the meniscal cells comprise vascular meniscal cells. In some embodiments, the meniscal cells comprise avascular meniscal cells. In some embodiments, the meniscal cells comprise vascular meniscal cells and avascular meniscal cells. In some embodiments, the plurality of cells is suspended in a biomimetic gel. In some embodiments, the plurality of cells has a density of about 50,000 cells per milliliter of biomimetic gel. In some embodiments, the biomimetic gel comprises type II collagen, chondroitin sulfate, hyaluronan or a combination thereof. In some embodiments, the methods further comprise crosslinking the biomimetic gel with alginate. In some embodiments, the biomimetic gel comprises one or more growth factors. In some embodiments, the biomimetic gel comprises an enzyme. In some embodiments, the enzyme is a protease. In some embodiments, the protease is a collagenase. In some embodiments, the methods further comprise maintaining the cell-seeded polymer scaffold composition in a cell culture.

In some embodiments, the cell culture comprises TGF-bet In some embodiments, the TGF-beta is present at a concentration of about 10 ng/ml in the cell culture. In some embodiments, the methods further comprise maintaining the cell-seeded polymer scaffold composition in the cell culture for about 1 week to about 3 weeks. In some embodiments, the methods further comprise maintaining the cell-seeded polymer scaffold composition in the cell culture for about 2 weeks. In some embodiments, electrospinning the polymer solution comprises feeding the first polymer solution and/or second polymer solution into and/or through the emitter on to the collector with a syringe pump. In some embodiments, the syringe pump operates at a feeding rate of about 2.0 mL/h. In some embodiments, the collector is stationary. In some embodiments, the polymer fibers comprise randomly oriented polymer fibers. In some embodiments, a spacing between the emitter output and the collector is about 16 cm. In some embodiments, the polymer fibers possess an average ultimate tensile strength of between about 0.1 MPa to about 1000 MPa after crosslinking. In some embodiments, the polymer fibers possess an average ultimate tensile strength of between about 1 MPa and about 500 MP after crosslinking. In some embodiments, the polymer fibers possess an average ultimate tensile strength of between about 1 MPa and about 100 MP after crosslinking. In some embodiments, the polymer fibers possess an average ultimate tensile strength of between about 25 MPa to about 90 MPa after crosslinking. In some embodiments, the collector comprises a rotating collector. In some embodiments, the collector comprises a rotating drum collector. In some embodiments, the collector or portion thereof possesses a cone shape. In some embodiments, electrospinning comprises aligning the polymer fibers on the rotating collector. In some embodiments, the methods further comprise rotating the rotating collector at about 2400 RPM. In some embodiments, a spacing between the emitter output and the collector is about 12 cm. In some embodiments, the polymer fibers possess an average ultimate tensile strength of between about 1 MPa and about 2000 MPa in the direction parallel to the aligned fibers after crosslinking. In some embodiments, the polymer fibers possess an average ultimate tensile strength of between about 10 MPa and about 1000 MPa in the direction parallel to the aligned fibers after crosslinking. In some embodiments, the polymer fibers possess an average ultimate tensile strength of between about 125 MPa to about 325 MPa in the direction parallel to the aligned fibers after crosslinking. In some embodiments, the polymer fibers possess a diameter of between about 5 nm and 10 µm. In some embodiments, the polymer fibers possess a diameter of between about 50 nm and about 5 µm. In some embodiments, the polymer fibers possess a diameter of about 1 µm. In some embodiments, the methods further comprise covering the collector with aluminum foil. In some embodiments, the methods further comprise coating the collector with an agent. In some embodiments, the agent comprises a non-stick agent. In some embodiments, the non-stick agent comprises polytetrafluoroethylene. In some embodiments, the methods further comprise contacting the polymer scaffold composition with a biomimetic gel. In some embodiments, the biomimetic gel is distributed throughout the polymer scaffold composition or a portion thereof. In some embodiments, the methods further comprise producing a plurality of polymer scaffold compositions. In some embodiments, the methods further comprise combining the plurality of polymer scaffold compositions to form a multilayer construct. In some embodiments, the methods further comprise contacting the multilayer construct with a biomimetic gel. In some embodiments, the methods further comprise layering the biomimetic gel and the polymer scaffold compositions. In some embodiments, the methods further comprise shaping the polymer scaffold composition or the multilayer construct to resemble a body part. In some embodiments, the body part is a knee meniscus or a portion thereof. In some embodiments, crosslinking the polymer fibers comprises photocrosslinking. In some embodiments, the methods further comprise photocrosslinking the polymer fibers multiple times. In some embodiments, crosslinking the polymer fibers comprises contacting the polymer fibers with a chemical crosslinking solution. In some embodiments, the chemical crosslinking solution comprises a chemical selected from an aldehyde, glutaraldehyde, calcium chloride or Trout's reagent.

Further disclosed herein are methods of producing a collagen scaffold composition, comprising: electrospinning a polymer solution consisting essentially of a collagen and a solvent onto a collector to form collagen fibers; and crosslinking the collagen fibers to produce the collagen scaffold composition. In some embodiments, the polymer solution does not comprise a polymer other than collagen. In some embodiments, electrospinning and crosslinking occur simultaneously. In some embodiments, crosslinking occurs after electrospinning. In some embodiments, the solvent comprises PBS and ethanol. In some embodiments, the collagen is dissolved to a 16 wt % solution. In some embodiments, the solvent comprises hexafluoro-2-propanol (HFIP). In some embodiments, the solvent comprises water. In some embodiments, the collagen is methacrylated collagen and the collagen fibers are methacrylated collagen fibers. In some embodiments, the methods further comprise releasing an oxidant from the methacrylated collagen fibers, resulting in a chemical bond between one or more of the methacrylated collagen fibers. In some embodiments, releasing the oxidant comprises contacting the collagen scaffold composition with riboflavin. In some embodiments, the methods further comprise contacting the collagen scaffold composition with a photoinitiator. In some embodiments, the methods further comprise exposing the collagen scaffold composition to an ultraviolet light to release the oxidant from the methacrylated collagen fibers, resulting in a chemical bond between one or more of the methacrylated collagen fibers. In some embodiments, the collagen is conjugated to a biotin and the collector comprises avidin. In some embodiments, the methods further comprise contacting the collagen fibers with a plurality of cells to form a cell-seeded collagen scaffold composition. In some embodiments, contacting the collagen fibers with the plurality of cells comprises electrospraying the plurality of cells on to the collagen fibers. In some embodiments, electrospinning the polymer solution and electrospraying the plurality of cells occurs simultaneously. In some embodiments, electrospraying the plurality of cells occurs after electrospinning the polymer solution. In some embodiments, electrospraying the plurality of cells occurs after crosslinking the collagen fibers. In some embodiments, electrospraying the plurality of cells occurs before crosslinking the collagen fibers. In some embodiments, electrospraying the plurality of cells and cross-linking the polymer fibers occur simultaneously. In some embodiments, electrospinning the polymer solution, electrospraying the plurality of cells and cross-linking the polymer fibers occurs simultaneously. In some embodiments, the method encapsulates the plurality of cells in the cell-seeded collagen scaffold composition. In some embodiments, the plurality of cells comprises mesenchymal stem cells, meniscal cells, chondroblasts, chondrocytes or a combination thereof. In some embodiments, the meniscal cells comprise vascular meniscal cells. In some embodiments, the meniscal cells comprise avascular meniscal cells. In some embodiments, the meniscal cells comprise vascular meniscal cells and avascular meniscal cells. In some embodiments, the plurality of cells is suspended in a biomimetic gel. In some embodiments, the plurality of cells has a density of about 50,000 cells per milliliter of biomimetic gel. In some embodiments, the biomimetic gel comprises type II collagen, chondroitin sulfate, hyaluronan, and combinations thereof. In some embodiments, the methods further comprise crosslinking the biomimetic gel with alginate. In some embodiments, the biomimetic gel comprises one or more growth factors. In some embodiments, the biomimetic gel comprises an enzyme. In some embodiments, the enzyme is a protease. In some embodiments, the protease is a collagenase. In some embodiments, the methods further comprise assaying the plurality of cells for cell viability, cell morphology and gene expression after adding the cells to the collagen scaffold composition. In some embodiments, the methods further comprise maintaining the cell-seeded collagen scaffold composition in a cell culture. In some embodiments, the cell culture comprises TGF-beta. In some embodiments, the TGF-beta is present at a concentration of 10 ng/ml of the cell culture. In some embodiments, the methods further comprise maintaining the cell-seeded collagen scaffold composition in the cell culture for about 1 week to about 3 weeks. In some embodiments, the methods further comprise maintaining the cell-seeded collagen scaffold composition in the cell culture for about 2 weeks. In some embodiments, electrospinning comprises applying a voltage to the polymer solution. In some embodiments, the voltage is about 15 kV to about 20 kV. In some embodiments, the methods further comprise applying a voltage to the collector. In some embodiments, the voltage is about −10 kV to about −1 kV. In some embodiments, electrospinning comprises loading an emitter with the polymer solution and ejecting the polymer solution through an emitter output. In some embodiments, electrospinning the polymer solution comprises feeding the polymer solution into and/or through the emitter with a syringe pump. In some embodiments, the syringe pump operates at a feeding rate of about 2.0 mL/h. In some embodiments, the collector is stationary. In some embodiments, the polymer fibers comprise randomly oriented polymer fibers. In some embodiments, a spacing between the emitter output and the collector is about 16 cm. In some embodiments, the polymer fibers possess an average ultimate tensile strength of between about 0.1 MPa to about 1000 MPa after crosslinking. In some embodiments, the polymer fibers possess an average ultimate tensile strength of between about 1 MPa and about 500 MP after crosslinking. In some embodiments, the polymer fibers possess an average ultimate tensile strength of between about 1 MPa and about 100 MP after crosslinking. In some embodiments, the collector is a rotating collector. In some embodiments, the collector is a rotating drum collector. In some embodiments, the collector is shaped like the collector depicted in FIG. 3 and FIG. 4A. In some embodiments, electrospinning comprises aligning the collagen fibers on the rotating collector. In some embodiments, the methods further comprise rotating the rotating collector at about 2400 RPM. In some embodiments, a spacing between the emitter output and the collector is about 12 cm. In some embodiments, the collagen fibers possess an average ultimate tensile strength of between about 1 MPa and about 2000 MPa in the direction parallel to the aligned fibers after crosslinking. In some embodiments, the collagen fibers possess an average ultimate tensile strength of between about 10 MPa and about 1000 MPa in the direction parallel to the aligned fibers after crosslinking. In some embodiments, the collagen fibers possess a diameter of between about 5 nm and 10 µm. In some embodiments, the collagen fibers possess a diameter of between about 50 nm and about 5 µm. In some embodiments, the collagen fibers possess a diameter of about 1 µm. In some embodiments, the methods further comprise covering the collector with aluminum foil. In some embodiments, the methods further comprise coating the collector with an agent. In some embodiments, the agent comprises a non-stick agent. In some embodiments, the non-stick agent comprises polytetrafluoroethylene. In some embodiments, the methods further comprise producing a plurality of collagen scaffold compositions. In some embodiments, the methods further comprise combining the plurality of collagen scaffold compositions to form a multilayer construct. In some embodiments, the methods further comprise contacting the multilayer construct with a biomimetic gel. In some embodiments, the methods further comprise layering the biomimetic gel and the collagen scaffold compositions. In some embodiments, the methods further comprise shaping the collagen scaffold composition or the multilayer construct to resemble a body part. In some embodiments, the body part is a knee meniscus or a portion thereof. In some embodiments, crosslinking the polymer fibers comprises photocrosslinking. In some embodiments, the methods further comprise photocrosslinking the polymer fibers multiple times. In some embodiments, crosslinking the polymer fibers comprises contacting the polymer fibers with a chemical crosslinking solution. In some embodiments, the chemical crosslinking solution comprises a chemical selected from an aldehyde, glutaraldehyde, calcium chloride or Trout's reagent. In some embodiments, the methods further comprise loading the chemical crosslinking solution into a chemical crosslinking solution emitter. In some embodiments, the methods further comprise ejecting the chemical crosslinking solution from the chemical crosslinking solution emitter and electrospinning the polymer solution simultaneously, wherein the chemical crosslinking solution and the polymer solution are combined before they are on the collector.

Disclosed herein are polymer scaffold compositions comprising a plurality of collagen fibers, wherein the collagen fibers are electrospun and crosslinked.

Further disclosed herein are polymer scaffold compositions polymer scaffold composition comprising a plurality of polymer fibers having a structure comprising: a shell comprising the first polymer; and a core comprising the second polymer, wherein the polymer fibers are electrospun and crosslinked. In some embodiments, the first polymer comprises collagen. In some embodiments, the first polymer consists essentially of collagen. In some embodiments, the polymer fibers are aligned. In some embodiments, the polymer scaffold composition is biodegradable.

Disclosed herein are cell-seeded polymer scaffold compositions comprising: a polymer scaffold composition comprising a plurality of collagen fibers, wherein the collagen fibers are electrospun and crosslinked; and a plurality of cells.

Further disclosed herein are cell-seeded polymer scaffold compositions comprising: polymer scaffold composition comprising a plurality of polymer fibers having a structure comprising: a shell comprising the first polymer; and a core comprising the second polymer, wherein the polymer fibers are electrospun and crosslinked; and a plurality of cells. In some embodiments, the first polymer fiber is collagen. In some embodiments, the second polymer fiber is polylactic acid. In some embodiments, the polymer fibers are aligned. In some embodiments, the plurality of cells comprises cartilaginous cells. In some embodiments, the plurality of cells comprises meniscal cells. In some embodiments, the cell-seeded polymer scaffold composition comprises a meniscal implant or portion thereof. In some embodiments, the polymer fibers are biodegradable. In some embodiments, the polymer fibers have a wet-strength half life of at least about 6 months.

Disclosed herein are methods of treating a tissue defect in a subject comprising administering to the subject a polymer scaffold composition comprising a plurality of collagen fibers, wherein the collagen fibers are electrospun and crosslinked.

Further disclosed herein are methods of treating a tissue defect in a subject comprising administering a polymer scaffold composition comprising a plurality of polymer fibers having a structure comprising: a shell comprising the first polymer; and a core comprising the second polymer, wherein the polymer fibers are electrospun and crosslinked.

Disclosed herein are methods of treating a tissue defect in a subject comprising administering a cell-seeded polymer scaffold composition comprising: a polymer scaffold composition comprising a plurality of collagen fibers, wherein the collagen fibers are electrospun and crosslinked; and a plurality of cells.

Further disclosed herein are methods of treating a tissue defect in a subject comprising administering a cell-seeded polymer scaffold composition comprising: a polymer scaffold composition comprising a plurality of polymer fibers having a structure comprising: a shell comprising the first polymer; and a core comprising the second polymer, wherein the polymer fibers are electrospun and crosslinked; and a plurality of cells. In some embodiments, treating the tissue defect results in preventing damage to articular cartilage. In some embodiments, the tissue defect is due to osteoarthritis. In some embodiments, the tissue defect is due to a joint defect or a joint injury. In some embodiments, the joint injury is selected from an elbow injury, a wrist injury, a neck injury, a hip injury, a shoulder injury, a knee injury, an ankle injury, a vertebrate injury, a finger injury and a toe injury. In some embodiments, the joint injury comprises a knee injury. In some embodiments, the knee injury comprises a meniscus lesion. In some embodiments, the plurality of cells is derived from the subject. In some embodiments, the plurality of cells is derived from a second subject. In some embodiments, in the subject is human. In some embodiments, the plurality of cells is derived from an animal. In some embodiments, the animal is a pig.

Disclosed herein are methods of replacing a meniscus or a portion thereof in a subject, comprising implanting the cell-seeded polymer scaffold composition of any one of claims 8-16.

Further disclosed herein are cell-seeded polymer scaffold compositions for use in treatment of a joint defect, wherein the cell-seeded polymer scaffold composition is made by any one of the methods disclosed herein.

Disclosed herein are polymer scaffold compositions for use in treatment of a joint defect, wherein the polymer scaffold composition is made by any one of the methods disclosed herein.

Further disclosed herein are systems for electrospinning a polymer solution, comprising: an emitter that can receive and emit a polymer solution; a syringe pump; a power supply that provides voltage to the emitter; and a collector for receiving a polymer fiber generated by the emitter. In some embodiments, the systems further comprise an emitter that can receive and emit a plurality of cells. In some embodiments, the collector comprises a grounded plate collector. In some embodiments, the collector comprises a rotating collector. In some embodiments, the rotating collector is a v-shaped rotating collector. In some embodiments, the rotating collector or portion thereof possesses a cone shape. In some embodiments, the system comprises a first emitter having a first emitter outlet and a second emitter having a second emitter outlet. In some embodiments, the first emitter outlet comprises a first duct with a first interior and the second emitter outlet comprises a second tube with a second interior, wherein the second tube is within the interior of the first tube and the first tube and the second tube are co-axial. In some embodiments, the emitter is stationary. In some embodiments, the emitter is mobile. In some embodiments, the systems further comprise a platform for the emitter. In some embodiments, the platform possesses an adjustable height. In some embodiments, the emitter comprises a needle. In some embodiments, the needle is a 21 gauge needle.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A-C depicts an overview of the electrospinning equipment and production of multiple polymer scaffold compositions. (A) A grounded plate collector was used to produce random polylactic acid (PLA) fibers and (B) a rotating collector was used to deposit aligned PLA fibers. (C) Process of production of multiple layers. Human meniscus cells encapsulated in a hydrogel consisting of collagen type II, chondroitin sulfate and hyaluronan were seeded onto a base aligned PLA scaffold, followed by placement of another scaffold above in the same fiber orientation. This was followed by another layer of cells and one more scaffold layer. To hold the layers together, a layer of 2% alginate was deposited over the entire stack and crosslinked.

FIG. 12A shows relative gene expression levels for CHAD and COL1A1. FIG. 12B shows relative gene expression levels for AGG and THY1.

FIG. 12C shows relative gene expression levels for COMP. Expression is shown as relative to monolayer cultured cells (dotted line).

FIG. 13A depicts aligned PLA fibers the same day they were electrospun, with no cells.

FIG. 13B depicts aligned PLA fibers 30 days after electrospinning, with no cells.

FIG. 13C depicts aligned PLA fibers 30 days after electrospinning, with cartilaginous cells.

FIG. 14A depicts scanning electron microscope images of fibrochondrocytes cultured on aligned mats of collagen I fibers (×10,000).

FIG. 14B depicts scanning electron microscope images of fibrochondrocytes cultured on aligned mats of collagen I fibers (×2,500).

FIG. 17B exemplifies high cell viability one month after simultaneous electrospraying and electrospinning.

FIG. 18A-C depicts microscopic images of two layered engineered tissue samples after 2 weeks in culture at 10× magnification (A) and 40× magnification of two different regions in the specimen (B & C). Lines point to electrospun layers.

FIG. 20A-D depicts the morphological structure of (A) aligned and (B) random ES collagen fibers, as well as meniscus avascular and vascular cells seeded upon (C) randomly aligned electrospun collagen scaffolds or (D) cells on aligned collagen scaffolds.

FIG. 21A-D depicts average tensile modulus of random ES collagen fibers, aligned ES collagen fibers and ES collagen fibers perpendicular to the direction of aligned fibers scaffolds, dried and cross-linked with glutaraldehyde (A), with or without cells after 1 or 3 weeks (B). Ultimate stress for respective samples is shown in (C) and (D).

FIG. 27A-C depicts collagen type I immunostain at (A) 10× and (B) 40× magnification in a (C) multi-layer construct after two weeks.

FIG. 28A-B depicts (A) a macro top-view and (B) a macro side-view of half a disc of a meniscus like shape of engineered tissue (scale in mm), produced according to schematic shown in FIG. 24.

FIG. 29A-B depicts a schematic (A) for co-axial electrospinning to produce electrospun fibers with a collagen shell and polylactic acid core and an exemplary drum collector (B).

DETAILED DESCRIPTION OF THE INVENTION

Figure 1A:
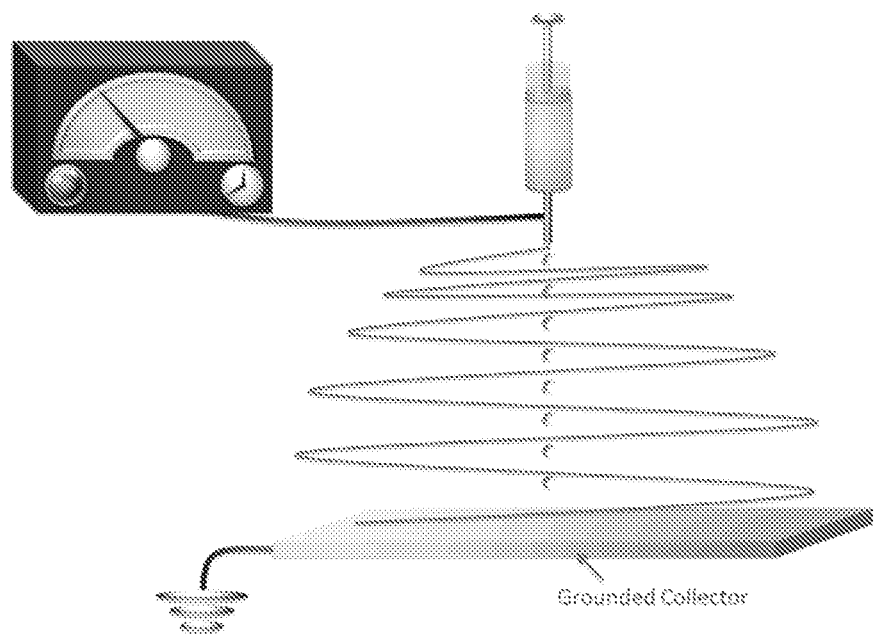
FIG. 1A exemplifies electrospinning of randomly oriented fibers. A syringe pump is used to extrude a polymer in solution through a needle (also called a spinneret). High voltage is applied to the needle which charges the polymer solution exiting the needle. A grounded collector plate provides a voltage differential to attract the charged polymer as a jet. The polymer jet dries in air and fibers are randomly deposited as a mat on the grounded plate.
Figure 1B:
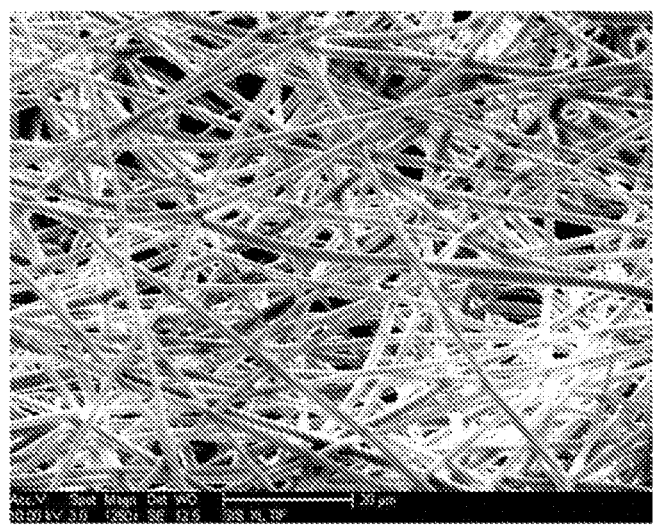
FIG. 1B depicts an electrospun polymer scaffold with randomly oriented polymer fibers.
Figure 2:
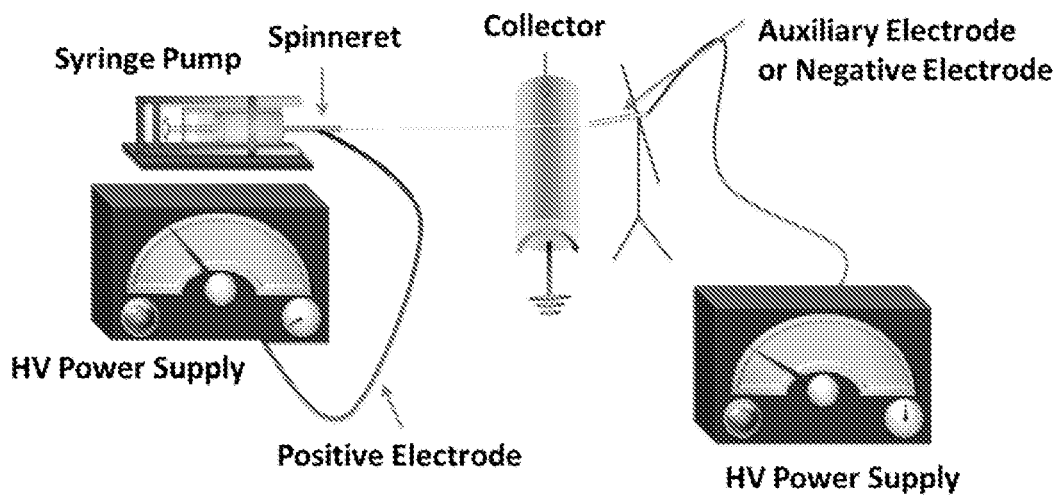
FIG. 2 exemplifies electrospinning of aligned fibers. A syringe pump is used to extrude a polymer in solution through a needle (also called a spinneret). High voltage is applied to the needle which charges the polymer solution exiting the needle. An auxiliary or negative electrode provides a voltage differential to attract the charged polymer as a jet. The rotating collector intercepts the fibers prior to their reaching the auxiliary electrode, and collects aligned electrospun fibers.

Many tissues do not have the capacity to regenerate or repair, so damage or injury to a tissue is irreversible. In addition to the poor ability to heal, injuries to tissues, such as cartilage, also result in significant pain and disability. Even with surgery, return of function is often limited. There is a growing interest in replacing tissues with modified cells or fabricated tissue implants. However, fabricating and implementing tissue implants presents several challenges. Ideally, a tissue implant does not contain any toxic components or foreign compounds that would be rejected by the immune system of a recipient. In addition, a tissue implant would have the capacity to be remodeled, broken down, vascularized and infiltrated by a recipient's endogenous cells. The methods, compositions and systems disclosed herein address these and other issues related to tissue repair and replacement.

Methods of Producing a Polymer Scaffold Composition

Disclosed herein, in some embodiments, are methods of producing a polymer scaffold composition, comprising: i) electrospinning a polymer solution onto a collector to form polymer fibers; and ii) crosslinking the polymer fibers to produce a polymer scaffold. In some embodiments, electrospinning comprises loading the polymer solution into an emitter, wherein the emitter comprises an emitter outlet, and ejecting the polymer solution from the emitter outlet to form polymer fibers.

Electrospinning

In some embodiments, electrospinning comprises applying a voltage to the polymer solution. In some embodiments, applying a voltage to the polymer solution results in a charged polymer solution. In some embodiments, the methods further comprise applying a grounding voltage to the collector. In some embodiments, applying the grounding voltage to the collector produces a voltage differential that attracts the charged polymer solution to the collector. In some embodiments, attracting the charged polymer solution to the collector results in a streaming or jetting of the polymer solution to the collector so that the polymer solution contacts the collector in a formation of a line or string. In some embodiments, the polymer solution polymerizes to produce the polymer fibers. In some embodiments, the polymer solution polymerizes in the formation of the line or string to produce the polymer fibers. In some embodiments, the polymer solution polymerizes to form the polymer fibers before the polymer fibers contact the collector. In some embodiments, the polymer solution partially polymerizes to form at least a portion of the polymer fibers before the polymer solution contacts the collector In some embodiments, the polymer solution polymerizes to form at least of the portion of the polymer fibers after the polymer solution contacts the collector.

In some embodiments, electrospinning comprises applying a voltage of about 1 kV, about 2 kV, about 3 kV, about 4 kV, about 5 kV, about 6 kV, about 7 kV, about 8 kV, about 9 kV, about 10 kV, about 11 kV, about 12 kV, about 13 kV, about 14 kV, about 15 kV, about 16 kV, about 17 kV, about 18 kV, about 19 kV, about 20 kV, about 21 kV, about 22 kV, about 23 kV, about 24 kV, about 25 kV, about 26 kV, about 27 kV, about 28 kV, about 29 kV, about 30 kV, about 35 kV, about 40 kV, about 45 kV or about 50 kV to the polymer solution. In some embodiments, electrospinning comprises applying a voltage of about 15 kV to about 20 kV to the polymer solution. In some embodiments, electrospinning comprises applying a voltage of about 17 kV to the polymer solution. In some embodiments, the methods further comprise applying a different voltage to a first polymer solution relative to a second polymer solution.

In some embodiments, applying the grounding voltage to the collector comprises applying a negative voltage to the collector. In some embodiments, the grounding voltage possesses an absolute value that is the same as the voltage applied to the polymer solution. In some embodiments, the grounding voltage possesses an absolute value that is different than the voltage applied to the polymer solution. In some embodiments, the grounding voltage possesses an absolute value that is less than the voltage applied to the polymer solution. In some embodiments, the grounding voltage possesses an absolute value that is greater than the voltage applied to the polymer solution. In some embodiments, the grounding voltage is about −1 kV, about −2 kV, about −3 kV, about −4 kV, about −5 kV, about −6 kV, about −7 kV, about −8 kV, about −9 kV, about −10 kV, about −11 kV, about −12 kV, about −13 kV, about −14 kV, about −15 kV, about −16 kV, about −17 kV, about −18 kV, about −19 kV, about −20 kV. In some embodiments, the grounding voltage is about −25 kV, about −30 kV, about −40 kV or about −50 kV. In some embodiments, electrospinning comprises applying a voltage of −1 kV to the collector.

In some embodiments, the methods comprise applying 20 kV to the polymer solution and −1 kV is applied to the collector. In some embodiments, the voltage differential is about 1 kV, about 2 kV, about 3 kV, about 4 kV, about 5 kV, about 6 kV, about 7 kV, about 8 kV, about 9 kV, about 10 kV, about 11 kV, about 12 kV, about 13 kV, about 14 kV, about 15 kV, about 16 kV, about 17 kV, about 18 kV, about 19 kV, about 20 kV, about 21 kV, about 22 kV, about 23 kV, about 24 kV, about 25 kV, about 26 kV, about 27 kV, about 28 kV, about 29 kV, about 30 kV, about 35 kV, about 40 kV, about 45 kV, about 50 kV, about 55 kV, about 60 kV, about 65 kV, about 70 kV, about 75 kV, about 80 kV, about 85 kV, about 90 kV, about 95 kV or about 100 kV.

In some embodiments, electrospinning comprises feeding the polymer solution into and/or through the emitter onto the collector with a syringe pump. In some embodiments, the syringe pump operates at a feeding rate of about 0.01 mL/h, about 0.02 mL/h, about 0.03 mL/h, about 0.04 mL/h, about 0.05 mL/h, about 0.06 mL/h, about 0.07 mL/h, about 0.08 mL/h, about 0.09 mL/h, about 0.1 mL/h, about 0.2 mL/h, about 0.3 mL/h, about 0.4 mL/h, about 0.5 mL/h, about 0.6 mL/h, about 0.7 mL/h, about 0.8 mL/h, about 0.9 mL/h, about 1.0 mL/h, about 1.1 mL/h, about 1.2 mL/h, about 1.3 mL/h, about 1.4 mL/h, about 1.5 mL/h, about 1.6 mL/h, about 1.7 mL/h, about 1.8 mL/h, about 1.9 mL/h, about 2.0 mL/h, about 2.1 mL/h, about 2.2 mL/h, about 2.3 mL/h, about 2.4 mL/h, about 2.5 mL/h, about 2.6 mL/h, about 2.7 mL/h, about 2.8 mL/h, about 2.9 mL/h, about 3.0 mL/h, about 4.0 mL/h, about 5.0 mL/h, about 6.0 mL/h, about 8.0 mL/h, or about 10.0 mL/h. In some embodiments, the syringe pump operates at a feeding rate of about 2 mL/h. In some embodiments, the syringe pump operates at a feeding rate of about 1 mL/h.

In some embodiments, the methods further comprise positioning the emitter outlet at a distance from the collector. In some embodiments, positioning the emitter at the distance controls the size of the polymer scaffold composition. In some embodiments, the methods comprise positioning the emitter outlet close to the collector to produce a small polymer scaffold composition relative to a polymer scaffold composition produced by positioning the emitter outlet far from the collector. In some embodiments, the methods comprise positioning the emitter outlet about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29 or about 30 cm from the collector. In some embodiments, the methods comprise positioning the emitter outlet 16 cm from the collector. In some embodiments, the methods comprise positioning the emitter outlet 12 cm from the collector. In some embodiments, the emitter is stationary. In some embodiments, the methods further comprise moving the emitter. In some embodiments, moving the emitter and electrospinning occur simultaneously. In some embodiments, moving the emitter and electrospinning occur sequentially.

Electrospinning a Plurality of Polymer Solutions

In some embodiments, the methods further comprise electrospinning a plurality of polymer solutions to form the polymer fibers on the collector. In some embodiments, the methods further comprise loading a plurality of polymer solutions into a plurality of emitters. In some embodiments, the methods further comprise electrospinning each polymer solution of the plurality of polymer solutions on to the collector simultaneously. In some embodiments, the methods further comprise electrospinning each polymer solution of the plurality of polymer solutions on to the collector sequentially. In some embodiments, the methods further comprise electrospinning a plurality of polymer solutions, wherein the plurality of polymer solutions possess different characteristics. In some embodiments, by non-limiting example, the different characteristics are selected from polymer identity, polymer concentration, protein content, chemical content, salt content, salt concentration and viscosity.

In some embodiments, the methods comprise co-axial electrospinning. In some embodiments, co-axial spinning comprises electrospinning a first polymer solution and a second polymer solution. In some embodiments, co-axial spinning comprises loading the first polymer solution into a first emitter and the second polymer solution into a second emitter. In some embodiments, the first emitter and the second emitter are connected to a hollow needle/cylinder that has two concentric channels (e.g. an inner channel within an outer channel). In some embodiments, the first polymer solution is ejected through the inner channel of the needle and the second polymer solution is ejected through the outer channel of the needle. In some embodiments, the second polymer solution surrounds/encapsulates the first polymer solution as they are emitted at the tip of the needle to produce the polymer fibers. In some embodiments, the polymer fiber comprises a core, wherein the core comprises a first polymer of the first polymer solution and a shell, wherein the shell comprises a second polymer of the second polymer solution. In some embodiments, co-axial electrospinning improves mechanical properties of fibers and scaffolds compared to electrospinning a single polymer solution. In some embodiments, the shell, but not the core, is exposed to an external environment (e.g. tissue). In some embodiments, the core comprises polylactic acid. In some embodiments, the shell comprises collagen. In some embodiments, the shell consists essentially of collagen. In some embodiments, the second polymer is less likely to cause a host immune response when implanted in host tissue than the first polymer. In some embodiments, the core increases the strength of the polymer fibers and/or electrospun polymer scaffold relative to a polymer fiber or an electrospun polymer scaffold that only comprises the second polymer. Exemplary embodiments of the aforementioned methods are demonstrated in Example 9 and FIGS. 29-33 of the present application.

In some embodiments, the methods comprise applying a first voltage to a first polymer solution to electrospin a first plurality of polymer fibers on the collector and applying a second voltage to a second polymer solution to electrospin a second plurality of polymer fibers on the collector. In some embodiments, electrospinning the first plurality of polymer fibers and electrospinning the second plurality of polymer fibers occurs simultaneously. In some embodiments, electrospinning the first plurality of polymer fibers and electrospinning the second plurality of polymer fibers occurs sequentially. In some embodiments, electrospinning the first plurality of polymer fibers and electrospinning the second plurality of polymer fibers occurs sequentially, such that an electrospun scaffold is produced, wherein the electrospun scaffold comprises the first plurality of polymer fibers and the second plurality of polymer fibers. In some embodiments, the first plurality of polymer fibers is encapsulated by the second plurality of polymer fibers. In some embodiments, the second plurality of polymer fibers is the plurality of polymer fibers that is exposed to an external environment (e.g. tissue). In some embodiments, the first plurality of polymer fibers comprises polylactic acid. In some embodiments, the second plurality of polymer fibers comprises collagen. In some embodiments, the second plurality of polymer fibers consists essentially of collagen. In some embodiments, the electrospun scaffold comprises external collagen fibers that are less likely to cause a host immune response when implanted in host tissue. In some embodiments, the electrospun scaffold comprises internal polylactic acid fibers that increase the strength of the electrospun scaffold relative to an electrospun scaffold that only comprises collagen fibers.

In some embodiments, the methods comprise applying the same voltage to each polymer solution of the plurality of polymer solutions. In some embodiments, the plurality of polymer solutions comprises at least a first polymer solution and a second polymer solution. In some embodiments, the methods comprise applying a first voltage to the first polymer solution and a second voltage to the second polymer solution, wherein the first voltage and second voltage are the same. In some embodiments, the methods comprise applying a first voltage to the first polymer solution and a second voltage to the second polymer solution, wherein the first voltage and second voltage are different.

Electrospinning Randomly Oriented Polymer Fibers

Electrospinning, as disclosed herein in some embodiments, comprises ejecting the polymer solution from the emitter outlet so that the polymer solution comes out of the emitter in a whip-like or flailing fashion and landing on the collector to form randomly oriented polymer fibers on the collector. In some embodiments, the collector is a stationary collector. In some embodiments, the collector is a stationary plate collector. In some embodiments, the stationary collector is a grounded collector. In some embodiments, the methods further comprise moving the collector. In some embodiments, electrospinning and moving the collector occur simultaneously. In some embodiments, electrospinning and moving the collector occur sequentially.

Electrospinning Aligned Polymer Fibers

In some embodiments, the methods comprise electrospinning a polymer solution onto a collector to form polymer fibers, wherein the polymer fibers are aligned. In some embodiments, the methods comprise aligning the polymer fibers by electrospinning the polymer solution on to a rotating collector. In some embodiments, the rotating collector is a grounded collector. In some embodiments, the methods comprise rotating the rotating collector at about 100 RPM, about 200 RPM, about 300 RPM, about 400 RPM, about 500 RPM, about 600 RPM, about 800 RPM, about 900 RPM, about 1000 RPM, about 1100 RPM, about 1200 RPM, about 1400 RPM, about 1600 RPM, about 1800 RPM, about 2000 RPM, about 2200 RPM, about 2250 RPM, about 2300 RPM, about 2350 RPM, about 2400 RPM, about 2450 RPM, about 2500 RPM, about 2550 RPM, about 2600 RPM, about 2800 RPM, about 3000 RPM, about 3200 RPM, about 3400 RPM, about 3600 RPM, about 3800 RPM, about 4000 RPM, about 4200 RPM, about 4400 RPM, about 4600 RPM, about 4800 RPM, about 5000 RPM, about 5200 RPM, about 5400 RPM, about 5600 RPM, about 5800 RPM, or about 6000 RPM. In some embodiments, the methods comprise rotating the rotating collector at about 2400 RPM. In some embodiments, the methods comprise rotating the rotating collector at a constant speed. In some embodiments, the methods comprise rotating the rotating collector at an alternating speed. In some embodiments, the methods comprise rotating the rotating collector at a variable speed. In some embodiments, the methods comprise rotating the rotating collector, stopping the rotating and resuming the rotating. In some embodiments, the methods comprise controlling a rotating speed of the rotating collector to control the degree of alignment. In some embodiments, controlling the degree of alignment modulates a mechanical property of the polymer fibers.

In some embodiments, the methods comprise rotating the rotating collector, stopping the rotating and resuming the rotating, thereby forming polymer fibers on the collector, wherein the polymer fibers comprise randomly oriented polymer fibers and aligned polymer fibers.

Preparing the Collector

In some embodiments, the methods further comprise covering the collector with a material or a formulation. In some embodiments, covering occurs before electrospinning. In some embodiments, covering is selected from coating, spraying, dusting, sprinkling, washing, polishing and wrapping. In some embodiments, the material or formulation is selected from a liquid, an oil, an emulsion, a gel, a paper, a polymer, resin, a foil and a wax. In some embodiments, the methods further comprise covering the collector with aluminum foil. In some embodiments, the methods further comprise covering the collector with a non-stick agent. In some embodiments, covering the collector with a non-stick agent prevents the polymer scaffold composition from sticking to the collector. In some embodiments, covering the collector with the non-stick agent allows the polymer scaffold composition to be removed from the collector with ease. In some embodiments, covering the collector with the non-stick agent allows the polymer scaffold composition to be removed from the collector without damage to the polymer scaffold composition. In some embodiments, covering comprises spraying the collector with the non-stick agent to produce a film of the non-stick agent on the collector. In some embodiments, the non-stick agent comprises a polymer. In some embodiments, the polymer comprises an acrylic polymer. In some embodiments, the polymer comprises a fluoropolymer. In some embodiments, the polymer comprises polytetrafluoroethylene (PTFE).

Method of Producing a Multilayer Construct

In some embodiments, the methods further comprise producing a plurality of polymer scaffold compositions. In some embodiments, the methods comprise producing the plurality of polymer scaffold compositions on one or more collectors. In some embodiments, the methods further comprise producing the plurality of polymer scaffold compositions simultaneously. In some embodiments, the methods further comprise producing the plurality of polymer scaffold compositions sequentially. In some embodiments, the methods further comprise combining the plurality of polymer scaffold compositions to form a multilayer construct. In some embodiments, the methods comprise producing the plurality of polymer scaffold compositions separately and combining the plurality of polymer scaffold compositions on a surface that is not the collector to form the multilayer construct. In some embodiments, combining the plurality of polymer scaffold compositions to form the multilayer construct comprises producing the plurality of polymer scaffold compositions sequentially on one collector. In some embodiments, the methods comprise combining 2, 3, 4, 5, 6, 7, 8, 9, 10 or more polymer scaffold compositions to form the multilayer construct. In some embodiments, the methods further comprise combining at least three polymer scaffold compositions to form the multilayer construct. In some embodiments, the methods comprise combining about 10, about 20, about 30, about 40, about 50, about 60, about 70, about 80, about 90, or about 100 polymer scaffold compositions to form the multilayer construct. In some embodiments, the methods further comprise combining about 200, about 300, about 400, about 500, about 600, about 700, about 800, about 900 or about 1000 polymer scaffold compositions to form the multilayer construct. In some embodiments, the methods further comprise combining about 10,000, about 100,000, or about 1,000,000 polymer scaffold compositions to form the multilayer construct.

Methods of Producing a Cell-Seeded Polymer Scaffold Composition and a Cell-Seeded Multilayer Construct Disclosed herein, in some embodiments, are methods of producing a cell-seeded polymer scaffold composition, comprising i) electrospinning a polymer solution onto a collector to form polymer fibers; ii) crosslinking the polymer fibers; and iii) contacting the polymer fibers with a cell.

Disclosed herein, in some embodiments, are methods of producing a cell-seeded polymer scaffold composition, comprising i) electrospinning a polymer solution onto a collector to form polymer fibers; ii) crosslinking the polymer fibers to produce the polymer scaffold composition; and iii) contacting the polymer scaffold composition with a cell, to form a cell-seeded polymer scaffold composition.

In some embodiments, the methods further comprise contacting the polymer fibers with a plurality of cells. In some embodiments, the methods further comprise contacting the polymer scaffold composition with a plurality of cells. In some embodiments the methods further comprise electrospinning a plurality of polymer scaffold compositions to produce a multilayer construct. In some embodiments, the methods further comprise contacting the multilayer construct with the cell to produce a cell-seeded multilayer construct. In some embodiments, the methods further comprise contacting the multilayer construct with a plurality of cells to produce the cell-seeded multilayer construct. Unless otherwise specified, in some embodiments, the terms cell-seeded polymer scaffold composition and cell-seeded multilayer construct are used interchangeably.

In some embodiments, contacting the polymer fibers with a cell or a plurality of cells comprises electrospraying the plurality of cells into the polymer solution as it is electrospun (e.g. electrospinning the polymer solution and electrospraying the plurality of cells occurs simultaneously). In some embodiments, the polymer solution is loaded into a polymer solution emitter with a first outlet and the plurality of cells is loaded into a cell emitter with a second outlet. In some embodiments, the first outlet and the second outlet are positioned close together such that the polymer solution contacts the plurality of cells when emitted. In some embodiments, the first outlet and the second outlet directed such that the polymer solution contacts the plurality of cells when emitted. In some embodiments, contacting the polymer fibers with a cell or a plurality of cells comprises electrospraying the plurality of cells on to the collector and electrospinning the polymer solution on to the collector simultaneously.

In some embodiments, contacting the polymer scaffold composition with a cell or a plurality of cells comprises electrospraying the plurality of cells. In some embodiments, contacting the polymer scaffold composition with a cell or a plurality of cells comprises electrospraying the plurality of cells on to the polymer scaffold composition. In some embodiments, contacting the polymer scaffold composition with a cell or a plurality of cells comprises electrospraying the plurality of cells on to the collector.

In some embodiments, electrospraying the plurality of cells comprises applying a voltage to the plurality of cells. In some embodiments, electrospraying comprises loading the plurality of cells into an emitter and applying a voltage to the plurality of cells. In some embodiments, the methods comprise electrospraying the plurality of cells on to the polymer scaffold composition. In some embodiments, the methods comprise electrospraying the plurality of cells into the polymer scaffold composition.

In some embodiments, electrospraying comprises applying a voltage of about 1 kV, about 2 kV, about 3 kV, about 4 kV, about 5 kV, about 6 kV, about 7 kV, about 8 kV, about 9 kV, about 10 kV, about 11 kV, about 12 kV, about 13 kV, about 14 kV, about 15 kV, about 16 kV, about 17 kV, about 18 kV, about 19 kV, about 20 kV, about 21 kV, about 22 kV, about 23 kV, about 24 kV, about 25 kV, about 26 kV, about 27 kV, about 28 kV, about 29 kV, about 30 kV, about 35 kV, about 40 kV, about 45 kV or about 50 kV to the plurality of cells. In some embodiments, electrospraying comprises applying a voltage of about 15 kV to about 20 kV to the plurality of cells. In some embodiments, electrospraying comprises applying a voltage of about 17 kV to the plurality of cells.

In some embodiments, the methods comprise electrospinning and crosslinking simultaneously. In some embodiments, the methods comprise electrospinning and electrospraying the plurality of cells simultaneously. In some embodiments, the methods comprise electrospinning, electrospraying and cross-linking simultaneously. In some embodiments, the methods comprise electrospinning and cross-linking sequentially. In some embodiments, the methods comprise electrospinning and electrospraying the plurality of cells sequentially. In some embodiments, the methods comprise electrospinning, electrospraying and cross-linking sequentially. In some embodiments, the methods comprise electrospinning and electrospraying simultaneously before cross-linking. In some embodiments, the methods comprise electrospinning and crosslinking simultaneously before electrospraying.

In some embodiments, electrospinning and electrospraying simultaneously results in a three-dimensional construct comprising the polymer fibers and the plurality of cells. In some embodiments, electrospinning and electrospraying simultaneously distributes the plurality of cells throughout the polymer scaffold composition. In some embodiments, electrospinning and electrospraying simultaneously distributes the plurality of cells in a portion of the polymer scaffold composition. In some embodiments, electrospinning and electrospraying simultaneously embeds the plurality of cells in the polymer scaffold composition or portions thereof. In some embodiments, the methods further comprise removing the polymer scaffold composition from the collector prior to electrospraying the plurality of cells on to the polymer scaffold composition.

In some embodiments, the cell or the plurality of cells is suspended in a biomimetic gel. In some embodiments, the methods comprise electrospraying the plurality of cells suspended in the biomimetic gel. In some embodiments, contacting the polymer scaffold composition with a cell or a plurality of cells comprises contacting the polymer scaffold composition with the plurality of cells in the biomimetic gel. In some embodiments, contacting the polymer scaffold composition with a cell or a plurality of cells comprises contacting the multilayer construct with the plurality of cells in the biomimetic gel. In some embodiments, the methods further comprise electrospraying the plurality of cells in the biomimetic gel to produce a layer of the biomimetic gel. In some embodiments, contacting the polymer scaffold composition with the plurality of cells in the biomimetic gel comprises producing the layer of a biomimetic gel on the polymer scaffold composition. In some embodiments, contacting the polymer scaffold composition with the plurality of cells in the biomimetic gel comprise contacting the multilayer construct with the layer of biomimetic gel. In some embodiments, the method of producing the cell-seeded multilayer construct comprises alternating producing layers of the polymer scaffold compositions and layers of the biomimetic gel, wherein the resulting multilayer construct comprises alternating layers of the polymer scaffold compositions and the layers of biomimetic gel.

In some embodiments, the methods comprise producing the layers of biomimetic gel and producing the polymer scaffold compositions. In some embodiments, the methods further comprise producing one layer of biomimetic gel between two polymer scaffold compositions. In some embodiments, the methods comprise layering one polymer scaffold composition between two layers of biomimetic gel. In some embodiments, the methods comprise alternating about 3 layers of biomimetic gel and about 3 polymer scaffolds. In some embodiments, the methods comprise alternating about 5 layers of biomimetic gel and about 5 polymer scaffolds. In some embodiments, the methods comprise alternating about 10 layers of biomimetic gel and about 10 polymer scaffolds. In some embodiments, the methods comprise alternating about 25 layers of biomimetic gel and about 25 polymer scaffolds. In some embodiments, the methods comprise alternating about 50 layers of biomimetic gel and about 50 polymer scaffolds. In some embodiments, the methods comprise alternating about 100 layers of biomimetic gel and about 100 polymer scaffolds. In some embodiments, the methods comprise alternating about 1000 layers of biomimetic gel and about 1000 polymer scaffolds. In some embodiments, the methods comprise producing a plurality of layers of biomimetic gel between the polymer scaffold compositions. In some embodiments, the methods comprise producing a plurality of polymer scaffold compositions between the layers of biomimetic gel.

In some embodiments, the methods comprise electrospraying the biomimetic gel onto the collector and electrospinning the polymer solution on to the collector simultaneously, so that the biomimetic gel is embedded in the polymer scaffold composition. In some embodiments, the methods comprise electrospraying the biomimetic gel onto the collector and electrospinning the polymer solution on to the collector simultaneously, so that the biomimetic gel is distributed throughout the polymer scaffold composition. In some embodiments, the methods comprise electrospraying the biomimetic gel onto the collector and electrospinning the polymer solution on to the collector simultaneously, so that the biomimetic gel is distributed in a portion of the polymer scaffold composition.

In some embodiments, the methods comprise electrospraying a plurality of biomimetic gels on to the collector. In some embodiments, the methods comprise electrospraying the plurality of biomimetic gels on to the collector simultaneously. In some embodiments, the methods comprise electrospraying the plurality of biomimetic gels on to the collector sequentially. In some embodiments, the methods comprise electrospraying the plurality of biomimetic gels on to the polymer scaffold composition simultaneously. In some embodiments, the methods comprise electrospraying the plurality of biomimetic gels on to the polymer scaffold composition sequentially.

Crosslinking

Chemical Crosslinking the Polymer Fibers

In some embodiments, the methods comprise crosslinking the polymer fibers. In some embodiments, crosslinking the polymer fibers comprises contacting the polymer fibers with a chemical crosslinking solution. In some embodiments, the chemical crosslinking solution is a liquid. In some embodiments, the chemical crosslinking solution is a gas/vapor. In some embodiments, the methods comprise crosslinking the polymer fibers of the polymer scaffold composition. In some embodiments, the methods comprise crosslinking the polymer fibers of the cell-seeded polymer scaffold composition. In some embodiments, the methods comprise crosslinking the polymer fibers of the cell-seeded multilayer construct. In some embodiments, contacting the polymer fibers with the chemical crosslinking solution occurs prior to adding the plurality of cells. In some embodiments, the methods further comprise washing the polymer fibers after contacting the polymer fibers with the chemical crosslinking solution. In some embodiments, the methods further comprise loading the chemical crosslinking solution into a chemical crosslinking solution emitter. In some embodiments, the methods further comprise ejecting the chemical crosslinking solution from the chemical crosslinking solution emitter on to the collector. In some embodiments, the methods further comprise ejecting the chemical crosslinking solution from the chemical crosslinking solution emitter on to the polymer fibers. In some embodiments, the methods further comprise ejecting the chemical crosslinking solution from the chemical crosslinking solution emitter and electrospinning the polymer solution simultaneously. In some embodiments, the methods further comprise ejecting the chemical crosslinking solution from the chemical crosslinking solution emitter and electrospinning the polymer solution, wherein the chemical crosslinking solution and the polymer solution are combined before they are on the collector. In some embodiments, crosslinking comprises contacting the polymer fibers with a chemical crosslinking solution occurs after adding the plurality of cells. In some embodiments, contacting the polymer fibers with a chemical crosslinking solution and adding the plurality of cells occurs simultaneously.

In some embodiments, the chemical crosslinking solution comprises an aldehyde. In some embodiments, the chemical crosslinking solution comprises Trout's reagent. In some embodiments, the chemical crosslinking solution comprises a glutaraldehyde solution to the polymer fibers. In some embodiments, the glutaraldehyde solution is between about 0.05% and about 5% w/w solution in PBS. In some embodiments, the glutaraldehyde solution is between about 0.1% and 1% w/w solution in PBS. In some embodiments, the glutaraldehyde solution is about 0.25% w/w solution in PBS. In some embodiments, the chemical crosslinking solution comprises a calcium chloride solution. In some embodiments, the calcium chloride solution is about 50 mM, about 75, mM, about 100 mM, about 125 mM, about 150 mM, about 175 mM or about 200 mM. In some embodiments, the calcium chloride solution is about 120 mM.

Photocrosslinking the Polymer Fibers

In some embodiments, crosslinking the polymer fibers comprises photocrosslinking the polymer fibers. In some embodiments, the methods comprise photocrosslinking the polymer fibers of the polymer scaffold composition. In some embodiments, the methods comprise photocrosslinking the polymer fibers of the cell-seeded polymer scaffold composition. In some embodiments, the methods comprise photocrosslinking the polymer fibers of the cell-seeded multilayer construct. In some embodiments, photocrosslinking the polymer fibers and adding the plurality of cells to the polymer scaffold composition occurs simultaneously. In some embodiments, photocrosslinking the polymer fibers occurs after adding the plurality of cells to the polymer scaffold composition or the multilayer construct. In some embodiments, photocrosslinking the polymer fibers occurs before adding the plurality of cells to the polymer scaffold composition or the multilayer construct. In some embodiments, photocrosslinking occurs once. In some embodiments, photocrosslinking occurs more than one time. In some embodiments, photocrosslinking occurs about 1 time, about 2 times, about 3 times, about 4 times, about 5 times, about 10 times, about 15 times, about 20 times, about 25 times, about 50 times, or about 100 times. In some embodiments, photocrosslinking occurs for less than about 1 sec, about 2 sec, about 3 sec, about 5 sec, about 10 sec, about 15 sec, about 20 sec, about 25 sec, about 30 sec, about 35 sec, about 40 sec, about 45 sec, about 50 sec, about 55 sec, about 60 sec, about 65 sec, about 70 sec, about 75 sec, bout 80 sec, about 85 sec, about 90 sec, about 95 sec, about 100 sec, about 105 sec, about 110 sec, about 115 sec, about 120 sec, about 125 sec, about 130 sec, about 135 sec, about 140 sec, about 145 sec about 150 sec, about 160 sec or about 180 sec. In some embodiments, photocrosslinking occurs for less than about 2 min.

In some embodiments, wherein the polymer fibers comprise methacrylated collagen fibers, cross-linking comprises exposing the methacrylated collagen fibers to an oxidant, resulting in a chemical bond between the methacrylated collagen fibers. In some embodiments, releasing the oxidant comprises adding riboflavin to the polymer scaffold composition. In some embodiments, releasing the oxidant comprises contacting the polymer scaffold composition with eosin. In some embodiments, the methods further comprise adding a photoinitiator to the polymer scaffold composition. In some embodiments, the methods further comprise exposing the polymer scaffold composition to light to release the oxidant, resulting in a chemical bond between one or more of the methacrylated collagen fibers. In some embodiments, the methods further comprise exposing the polymer scaffold composition to an ultraviolet light to release the oxidant resulting in the chemical bond between the methacrylated collagen fibers.

Crosslinking the Biomimetic Gel

In some embodiments, the methods further comprise crosslinking the biomimetic gel of the cell-seeded polymer scaffold composition. In some embodiments, the methods further comprise crosslinking the biomimetic gel of the cell-seeded multilayer construct. In some embodiments, crosslinking the biomimetic gel with alginate holds the plurality of cells in place. In some embodiments, crosslinking the biomimetic gel with alginate holds the plurality of cells in place temporarily. In some embodiments, crosslinking the biomimetic gel with alginate holds the plurality of cells in place until they proliferate or migrate. In some embodiments, crosslinking the biomimetic gel comprises contacting the biomimetic gel with a biomimetic gel crosslinking solution. In some embodiments, the biomimetic gel crosslinking solution comprises alginate. In some embodiments, the methods comprise crosslinking the biomimetic gel with alginate and adding the plurality of cells to the polymer scaffold composition simultaneously. In some embodiments, the methods comprise crosslinking the biomimetic gel with alginate after adding the plurality of cells to the polymer scaffold composition.

In some embodiments, the methods further comprise removing the polymer scaffold composition from the collector before crosslinking. In some embodiments, the methods further comprise crosslinking the polymer scaffold composition on the collector.

Further Modification of the Polymer Scaffold Composition/Construct

In some embodiments, the methods further comprise modifying or shaping the polymer scaffold composition, cell-seeded polymer scaffold composition or cell-seeded multilayer construct. In some embodiments, the methods further comprise cutting, melting, burning, mincing, carving, etching, trimming, breaking, bending, twisting, folding or hammering the polymer scaffold composition, the multilayer construct, the cell-seeded polymer scaffold composition or the cell-seeded multilayer construct.

In some embodiments, the methods further comprise shaping the polymer scaffold composition to resemble a body part or a portion thereof. In some embodiments, the methods further comprise shaping the cell-seeded polymer scaffold composition to resemble a body part or a portion thereof. In some embodiments, the methods further comprise shaping the multilayer construct to resemble a body part or a portion thereof. In some embodiments, the methods further comprise shaping the cell-seeded multilayer construct to resemble a body part or a portion thereof.

In some embodiments, the body part is selected from a nose, an ear, a skull, a collar bone, an esophagus, a trachea, a bronchial tube, a rib, a rib cage, a bone, a shoulder, an elbow, a wrist, a finger, a hand, a pelvis, a hip, a vertebrate, an intervertebral disc, a coccyx, a leg, a knee, a knee meniscus, an ankle, a foot and a toe, or a portion thereof. In some embodiments, the body part is a knee meniscus or a portion thereof. In some embodiments, the body part is a medial meniscus or a portion thereof. In some embodiments, the body part is a lateral meniscus or a portion thereof.

In some embodiments, the body part is an organ or a portion thereof. In some embodiments, the organ is selected from a heart, a kidney, a muscle, an epidermis, a brain, an eye, a lung, a stomach, an intestine, a colon, a uterus, an ovary, a prostate, a bladder, a liver, a pancreas, a thymus, a diaphragm or a portion thereof. In some embodiments the portion of the organ comprises a heart valve. In some embodiments the portion of the organ comprises a blood vessel.

In some embodiments, the body part is a gland. In some embodiments, the gland is selected from an adrenal gland, a pituitary gland and a thyroid gland.

In some embodiments, the body part comprises bone.

Obtaining and Culturing Cells for a Cell Seeded Polymer Scaffold Composition

In some embodiments, the methods further comprise harvesting or isolating the plurality of cells from a subject, a cadaver, an organ or a tissue. Wherein the plurality cells is harvested from a cadaver, in some embodiments, the plurality of cells is harvested less than about 1 hour, less than about 2 hours, less than about 4 hours, less than about 6 hours, less than about 12 hours, less than about 24 hours, less than about 36 hours, less than about 48 hours, or less than about 72 hours after death. In some embodiments, the plurality of cells is harvested from a cadaver less than about 72 hours after death. In some embodiments, isolating the plurality of cells comprises mincing the tissue. In some embodiments, isolating the plurality of cells comprises contacting the tissue with an enzymatic solution (e.g. trypsin). In some embodiments, isolating the plurality of cells comprises treating the plurality of cells with an antibiotic and/or an antimycotic. In some embodiments, the antibiotic is selected from penicillin, streptomycin, actinomycin D, ampicillin, blasticidin, carbenicillin, cefotaxime, fosmidomycin, gentamicin, kanamycin, neomycin, polymyxin B and a combination thereof. In some embodiments, the antimycotic is selected from amphotericin B, nystatin, natamycin and a combination thereof.

In some embodiments, the methods further comprise culturing the plurality of cells in a cell culture prior to contacting the polymer scaffold composition. In some embodiments, the plurality of cells are maintained in the cell culture for less than 24 hours, less than two days, less than three days or less than a week. In some embodiments, the plurality of cells are maintained in the cell culture for more than a week. In some embodiments, the plurality of cells are maintained in the cell culture for about 1 week to about 3 weeks. In some embodiments, the plurality of cells are maintained in the cell culture for about 2 weeks. In some embodiments, the plurality of cells are maintained in the cell culture for about one month. In some embodiments, the plurality of cells are maintained in the cell culture for more than one month.

In some embodiments, the methods comprise contacting the polymer scaffold composition with the plurality of cells when they have grown to about 10%, about 20%, about 30%, about 40%, about 50%, about 60%, about 70%, about 80%, about 90% or about 100% confluence in the cell culture.

In some embodiments, the methods comprise contacting the polymer scaffold composition with chondrocytes. As used herein, in some embodiments, the terms chondrocytes, cartilaginous cells, fibrocartilaginous cells, chondroblasts, meniscal cells and progenitors thereof are used interchangeably. In some embodiments, the chondrocytes are human chondrocytes. In some embodiments, the human chondrocytes are 80% to 90% confluent in cell culture. In some embodiments, the methods further comprise culturing the human chondrocytes at about 37° C. with humidified air containing 5% $CO_2$, and changing the cell culture medium about every four days.

Culturing the Cell-Seeded Polymer Scaffold Composition

In some embodiments, the methods comprise maintaining the cell-seeded polymer scaffold composition in the cell culture. In some embodiments, the methods comprise maintaining the cell-seeded polymer scaffold composition in the cell culture for less than 24 hours, less than two days, less than three days or less than a week. In some embodiments, the methods further comprise maintaining the cell-seeded polymer scaffold composition in the cell culture for more than a week. In some embodiments, the methods comprise maintaining the cell-seeded polymer scaffold composition in the cell culture for about 1 week to about 3 weeks. In some embodiments, the methods comprise maintaining the cell-seeded polymer scaffold composition in the cell culture for about 2 weeks. In some embodiments, the methods comprise maintaining the cell-seeded polymer scaffold composition in the cell culture for about one month. In some embodiments, the methods comprise maintaining the cell-seeded polymer scaffold composition in the cell culture for more than one month.

In some embodiments, the cell culture comprises an atmosphere of about 1%, about 2%, about 3%, about 5%, about 7%, about 10% or about 20% $O_2$. In some embodiments, the cell culture comprises an atmosphere of about 1%, about 2%, about 3%, about 4%, about 5%, about 6%, about 7%, about 8%, about 9% or about 10% $CO_2$. In some embodiments, the cell culture comprises an atmosphere of about 30° C., about 32° C., about 33° C., about 34° C., about 35°, about 36° C., about 37° C., about 38° C., about 39° C., about 40° C. or about 42° C.

In some embodiments, the methods further comprise storing the cell-seeded polymer scaffold composition at a cold temperature. In some embodiments, the methods further comprise storing the cell-seeded polymer scaffold composition at about 4° C. In some embodiments, the methods further comprise freezing the cell-seeded polymer scaffold composition. In some embodiments, the methods further comprise transporting the cell-seeded polymer scaffold composition at the temperature of cell culture conditions. In some embodiments, the methods further comprise transporting the cell-seeded polymer scaffold composition at about 4° C. In some embodiments, the methods further comprise transporting the cell-seeded polymer scaffold composition frozen.

In some embodiments, the methods further comprise assaying the plurality of cells for an activity or appearance. In some embodiments, by non-limiting example, the activity or appearance is selected from viability, differentiation, proliferation, morphology, adhesion, apoptosis, migration, integration with the polymer scaffold composition, protein expression, gene expression and a combination thereof. In some embodiments, by non-limiting example, the assaying comprises a method selected from confocal microscopy, fluorescence microscopy, scanning electron microscopy, real-time PCR, quantitative PCT, chromatin immunoprecipitation, immunohistochemistry, immunostaining, western blot, ELISA, northern blot, southern blot, fluorescence in situ hybridization, karyotyping, fluorescence activated cell sorting, cell counting, dye uptake, particle uptake, migration assay, adhesion assay or any combination thereof. In some embodiments, assaying the plurality of cells for gene expression comprises measuring gene expression of collagen type I, alpha I (COL1A1), SOX9, chondroadherin (CHAD), aggrecan (AGG), THY-1, or cartilage oligomeric matrix protein (COMP). In some embodiments, the methods further comprise comparing gene expression of the plurality of cells to their gene expression in a cell culture container. In some embodiments, by non-limiting example, the cell culture container is selected from a dish, a flask, a slide, a matrix, a tube and a chamber. In some embodiments, the cell culture container comprises a material selected from a plastic, a polymer, a metal, a paper, a wax, a gel, a resin and a glass.

Tissue Engineering

Disclosed herein, in some embodiments, are methods of tissue engineering, comprising i) electrospinning a polymer solution to produce a polymer scaffold composition; ii) placing the polymer scaffold composition in a cell culture; iii) contacting the cell culture with the plurality of cells; and iv) propagating the plurality of cells to produce an engineered tissue. Further disclosed herein, in some embodiments, are methods of tissue engineering, comprising i) electrospinning a polymer solution to produce a polymer scaffold composition; ii) contacting the polymer scaffold composition with the plurality of cells to form a cell-seeded polymer scaffold composition; iii) placing the cell-seeded polymer scaffold composition in a cell culture; and iv) propagating the plurality of cells to produce an engineered tissue. In some embodiments, the cell culture comprises a cell solution. In some embodiments, the cell solution comprises a cell culture medium. In some embodiments, the polymer scaffold composition provides a biomimetic environment for the cell. In some embodiments, the polymer scaffold composition supports growth and differentiation of the plurality of cells. In some embodiments, the methods further comprise propagating the plurality of cells. In some embodiments, the methods further comprise modifying the shape of the engineered tissue. In some embodiments, by non-limiting example, modifying the shape of the tissue comprises cutting, carving, molding, pressing, conforming, compressing, squeezing, rotating or folding the engineered tissue. In some embodiments, the methods further comprise contacting the cell culture with an extracellular matrix component.

In some embodiments, by non-limiting examples, the engineered tissue is selected from a vascular tissue, an osteochondral tissue, an epidermal tissue, a muscular tissue, an intestinal tissue, a neuronal tissue, fascia, dura mater, a reproductive tissue, a pancreatic tissue, an ocular tissue, an ear, an eye, a cornea, a nose, a brain, a sinus, a tooth, a bone, cartilage, skin, an esophagus, a trachea, a thymus, a thyroid, a heart, a heart valve, a blood vessel, a lung, a diaphragm, a lymph node, a breast, a nipple, a stomach, an intestine, a colon, a rectum, a pancreas, a spleen, a bladder, a kidney, a liver, an ovary, a uterus, a prostate, adipose tissue, skeletal muscle, smooth muscle, skin, and portions thereof, and combinations thereof.

Scaffold Composition

Disclosed herein, in various embodiments, are polymer scaffold compositions comprising a plurality of polymer fibers, wherein the polymer fibers electrospun and crosslinked. In some embodiments, the polymer scaffold compositions are produced by methods disclosed herein. In some embodiments, the methods comprise: electrospinning a polymer solution onto a collector to form polymer fibers; and crosslinking the polymer fibers to produce a polymer scaffold. In some embodiments, the polymer fibers comprise a shell. In some embodiments, the shell comprises collagen. In some embodiments, the shell consists essentially of collagen. In some embodiments, the polymer fibers comprise a core. In some embodiments, the core comprises polylactic acid.

In some embodiments, the polymer fibers of the polymer scaffold composition consist essentially of collagen.

In some embodiments, the polymer scaffold compositions possess pores. In some embodiments, pores are spaces or openings between the polymer fibers. In some embodiments, the pores possess a mean pore diameter. In some embodiments, the mean pore diameter is about 1 nm, about 5 nm, about 10 nm, about 15 nm, about 20 nm, about 25 nm, about 50 nm, about 100 nm. In some embodiments, the mean pore diameter is about 100 nm, about 200 nm, about 300 nm, about 400 nm, about 500 nm, about 600 nm, about 700 nm, about 800 nm, about 900 nm or about 1 micron. In some embodiments, the mean pore diameter is greater than 1 µm. In some embodiments, the mean pore diameter is about 1 µm, about 5 µm, about 10 µm, about 15 µm, about 20 µm, about 25 µm, about 50 µm, about 75 µm, about 100 µm, about 125 µm, about 150 µm, about 300 µm or about 500 µm.

In some embodiments, the polymer scaffold compositions are biodegradable. In some embodiments the electrospun polymer fibers or polymer scaffold composition possess a wet-strength half-life of about 2 weeks, about 3 weeks, about 4 weeks, about 5 weeks, about 6 weeks, about 7 weeks, about 8 weeks, about 9 weeks, about 10 weeks, about 12 weeks, about 4 months, about 5 months, about 6 months, about 7 months, about 8 months, about 9 months, about 10 months, about 11 months or about 1 year. In some embodiments, the electrospun polymer fibers have a wet-strength half life of about 6 months. In some embodiments, the polymer scaffold composition possesses a degradation rate that matches a rate of regenerating tissue. In some embodiments, the polymer scaffold composition degrades when placed in a subject (e.g. site of injury) and is replaced by regenerated tissue.

In some embodiments, the polymer scaffold compositions further comprise an extracellular matrix component or a portion thereof. In some embodiments, the extracellular matrix component is derived from a human, a cow, a horse, a sheep, a goat, a chimpanzee, a monkey, a rat, a pig, a mouse, a rabbit or a synthetic reaction. In some embodiments, the polymer scaffold compositions further comprise a support material, a protein, a glycoprotein, a proteoglycan, a biochemical or a combination thereof. In some embodiments, the polymer scaffold compositions further comprise a biomimetic gel.

In some embodiments, the polymer scaffold compositions further comprise chondroitin sulfate, hyaluronan, collagenase, lubricin or a combination thereof. In some embodiments, the polymer scaffold compositions further comprise a joint lubricant. In some embodiments, the joint lubricant comprises gelatin, heparin, synovial fluid or a combination thereof.

Cell-Seeded Polymer Scaffold/Multilayer Construct Compositions

Disclosed herein, in some embodiments, are cell-seeded polymer scaffold compositions comprising i) a polymer scaffold composition comprising a plurality of polymer fibers, wherein the plurality of polymer fibers are electrospun and crosslinked, and ii) a plurality of cells. Further disclosed herein are cell-seeded multilayer constructs comprising: a plurality of polymer scaffold compositions comprising a plurality of polymer fibers, wherein the plurality of polymer fibers is electrospun and crosslinked, and ii) a plurality of cells. In some embodiments, the polymer fibers comprise a shell. In some embodiments, the shell comprises collagen. In some embodiments, the shell consists essentially of collagen. In some embodiments, the polymer fibers comprise a core. In some embodiments, the core comprises polylactic acid. In some embodiments, the cell-seeded polymer scaffold compositions and the cell-seeded multilayer constructs are produced by any of the methods described herein. In some embodiments, the cell-seeded polymer scaffold compositions and the cell-seeded multilayer constructs are suitable for administering to a subject. In some embodiments, the cell-seeded polymer scaffold compositions and the cell-seeded multilayer constructs comprise an implant or a portion thereof. In some embodiments, implant is a meniscal implant. In some embodiments, the implant is an intervertebral implant. In some embodiments, the cell-seeded polymer scaffold compositions replace a tissue or a portion thereof. In some embodiments, the tissue is selected from cartilage, ligament, tendon, dura mater, fascia, cardiac tissue, epidermal tissue, skeletal muscle, smooth muscle, intestinal tissue, a neuronal tissue, osteochondral tissue and vascular tissue. In some embodiments, the cell-seeded polymer scaffold composition replaces a body part or portion thereof. In some embodiments, by non-limiting example, the body part is selected from an eye, a cornea, a brain, a sinus, a tooth, a bone, a joint, an esophagus, a trachea, a thymus, a thyroid, a heart, a heart valve, a blood vessel, a lung, a diaphragm, a lymph node, a breast, a nipple, a stomach, an intestine, a colon, a rectum, a pancreas, a spleen, a bladder, a kidney, a liver, an ovary, a uterus, a prostate gland or a portion thereof.

In some embodiments, the body part is selected from a nose, an ear, a skull, a collar bone, an esophagus, a trachea, a bronchial tube, a rib cage, a bone, a shoulder, an elbow, a wrist, a finger, a hand, a pelvis, a hip, a vertebrate, an intervertebral disc, a coccyx, a leg, a knee, a knee meniscus, an ankle, a foot, or a toe or a portion thereof. In some embodiments, the body part is a knee meniscus or a portion thereof. In some embodiments, the body part is a medial meniscus or a portion thereof. In some embodiments, the body part is a lateral meniscus or a portion thereof.

In some embodiments, the polymer fibers of the cell-seeded polymer scaffold compositions and the cell-seeded multilayer constructs consist essentially of collagen (e.g. a cell-seeded collagen scaffold composition). In some embodiments, the cell-seeded collagen scaffold compositions and the cell-seeded multilayer constructs are biodegradable, non-toxic and capable of being remodeled when placed in a subject, by the subject's endogenous enzymes.

Device/System

Disclosed herein, in some embodiments, are systems for electrospinning a polymer solution, comprising i) an emitter; ii) a collector for receiving a polymer fiber generated by the emitter; and iii) a power supply that provides a voltage to the emitter and the collector. In some embodiments, the systems are implemented for performing any of the methods disclosed herein. In some embodiments, the methods comprise: electrospinning a polymer solution onto a collector to form polymer fibers; and crosslinking the polymer fibers to produce a polymer scaffold.

Emitter

In some embodiments, the emitter comprises a syringe and a needle. In some embodiments, the emitter comprises a spinneret. In some embodiments, the spinneret comprises a syringe. In some embodiments, the emitter comprises a polymer solution chamber for loading and containing the polymer solution. In some embodiments, by non-limiting example, the polymer solution chamber is selected from a container, a syringe, a bottle, a barrel, a tube, a cup, a flask, a cylinder, a capillary, a channel, a pipe and a box. In some embodiments, the emitter comprises an emitter outlet, through which the polymer solution is ejected from the emitter. In some embodiments, by non-limiting example, the emitter outlet is selected from a tip, a needle, a capillary, a cone, a funnel, a nozzle, a hole and a combination thereof. In some embodiments, by non-limiting example, the emitter comprises a material selected from a glass, a plastic, a resin, a metal, a rubber, a polymer or a combination thereof.

In some embodiments, the polymer solution chamber possesses a volume selected from about 1 mL, about 2 mL, about 3 mL, about 4 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL. In some embodiments, the syringe volume is selected from about 200 mL, about 300 mL, about 400 mL, about 500 mL, about 600 mL, about 700 mL, about 800 mL, about 900 mL or about 1 L.

In some embodiments, the emitter outlet comprises a needle. In some embodiments, the needle is selected from a 3 gauge needle, 4 gauge needle, 5 gauge needle, 6 gauge needle, 7 gauge needle, 8 gauge needle, 9 gauge needle, 10 gauge needle, 11 gauge needle, 12 gauge needle, 13 gauge needle, a 14 gauge needle, a 15 gauge needle, a 16 gauge needle, a 17 gauge needle, a 18 gauge needle, a 19 gauge needle, a 20 gauge needle, a 21 gauge needle, a 22 gauge needle, a 23 gauge needle, a 24 gauge needle, a 25 gauge needle, a 26 gauge needle, a 27 gauge needle, a 28 gauge needle, a 29 gauge needle, a 30 gauge needle, a 31 gauge needle, a 32 gauge needle, a 33 gauge needle, a 34 gauge needle and a 35 gauge needle. In some embodiments, the needle comprises a 21 gauge needle.

In some embodiments, the length of the needle is about 1 mm, about 5 mm or about 1 cm. In some embodiments, the length of the needle is about ⅛ inch, about ¼ inch, about ½ inch, about ¾ inch, about 1 inch, about 1¼ inches, about 1½ inches, about 1¾ inches, about 2 inches, about 2¼ inches, about 2½ inches, about 2¾ inches, about 3 inches, about 3¼ inches, about 3½ inches, about 3¾ inches, about 4 inches, about 4¼ inches, about 4½ inches, about 4¾ inches or about 5 inches.

In some embodiments, the system further comprises a syringe pump.

Referring to FIGS. 6A and 6B, in some embodiments, the systems further comprise a platform for the emitter and/or the collector. In some embodiments, the platform is stationary. In some embodiments, the platform is secured to a table, a wall or a floor. In some embodiments, the platform is mobile (e.g. mounted on wheels). In some embodiments, the platform possesses an adjustable height.

Collector

In some embodiments, the collector comprises a surface material. In some embodiments, by non-limiting example, the surface material is selected from a plastic, a ceramic, a metal, a glass, a resin, a wax, a particulate, a synthetic material, a naturally-occurring product and a combination thereof. In some embodiments, the collector is coated, sprayed, or covered with a liquid, an oil, a gel, a paper, a polymer or a wax. In some embodiments, the collector is covered with aluminum foil. In some embodiments, the collector is coated with a non-stick agent. In some embodiments, the non-stick agent comprises an oil. In some embodiments, the non-stick agent comprises a wax. In some embodiments, the non-stick agent comprises a polymer. In some embodiments, by non-limiting example, the polymer comprises polytetrafluoroethylene (PTFE).

Figure 3:
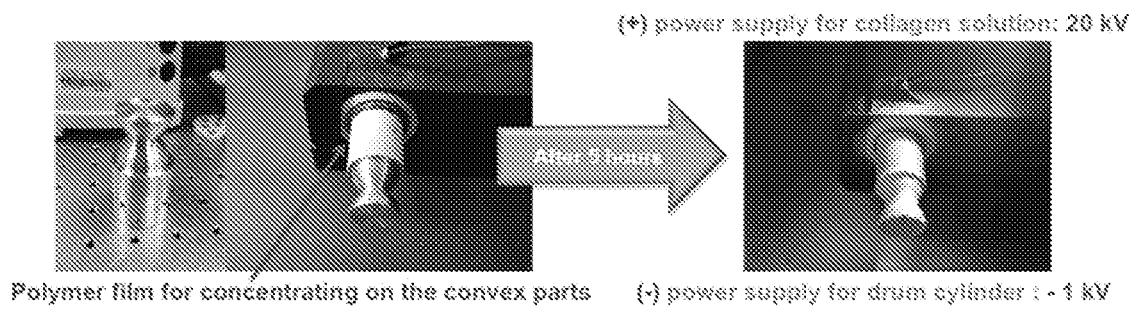
FIG. 3 exemplifies the process of collecting aligned electrospun fibers on a custom shaped rotating cylinder used to electrospin fibers in the shape of a human meniscus. Using low negative voltage for a drum cylinder is better for electrospinning to make a smaller electric field.
Figure 4A:
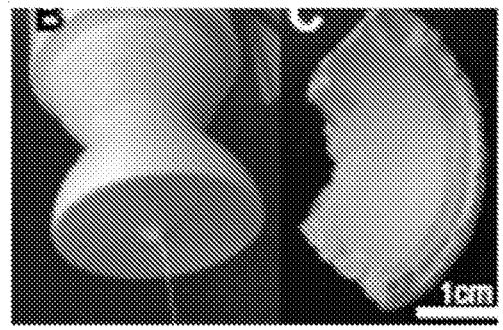
FIG. 4A depicts a custom shaped rotating cylinder (left) used to electrospin fibers in the shape of a meniscus (right).
Figure 4B:
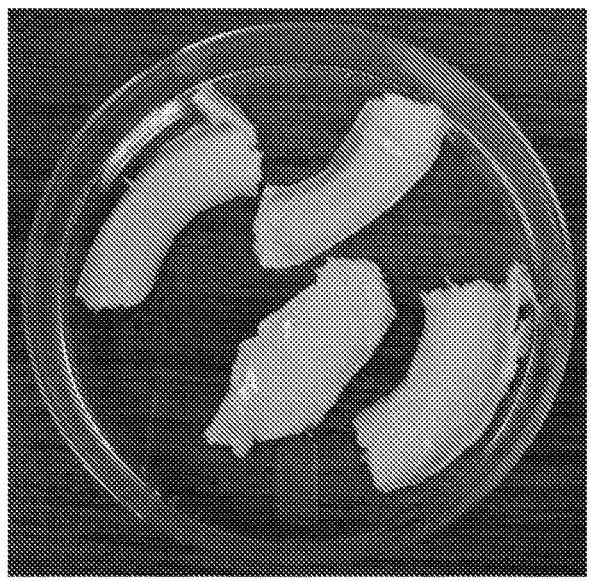
FIG. 4B depicts pieces of meniscus shaped electrospun collagen.
Figure 5A:
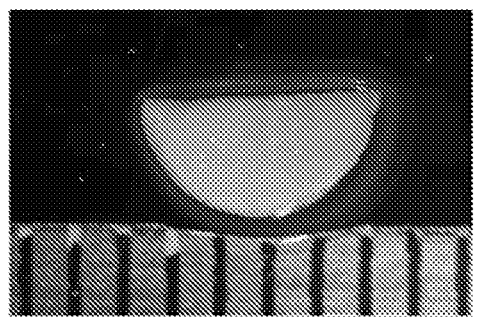
FIG. 5A-D depicts macroscopic images of aligned collagen electrospun onto a cylindrical rotating drum cylinder and subsequently cut into discs to form multi-layered constructs seeded with human mesenchymal stem cells in tri-matrix gel and encapsulated in alginate and cultured for 2 weeks using different growth factors.
Figure 5B:
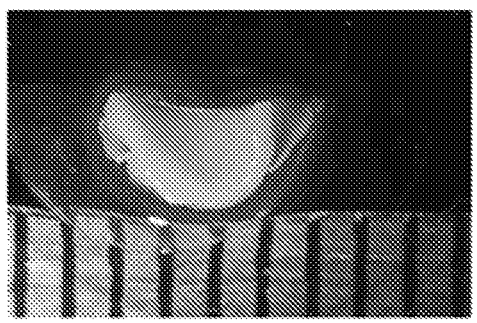
Figure 5C:
Figure 5D:
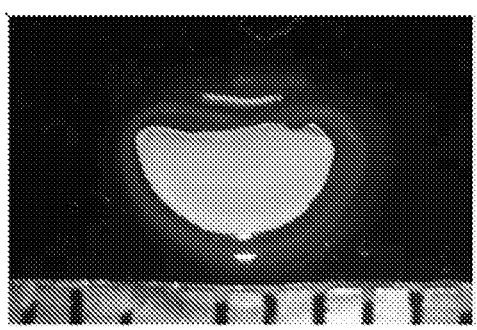

In some embodiments, the collector is a grounded plate collector. In some embodiments, the collector is a rotating collector. In some embodiments, the collector is a rotating drum collector. In some embodiments, the collector is a mandrel. In some embodiments, the rotating collector is cylindrical. In some embodiments, the rotating collector, as viewed down its axis of rotation, is circular, ovular, irregular, square, flat, planar, pointed, curved, rectangular or polygonal. In some embodiments, the rotating collector, as viewed down its axis of rotation, is circular. In some embodiments, the rotating collector, as viewed down its axis of rotation, has a variable width or diameter. In some embodiments, the rotating collector, as viewed down its axis of rotation, has a variable shape. Referring to FIGS. 3 and 4A, in some embodiments, the rotating collector is a v-shaped rotating collector. Referring to FIGS. 4B and 5, in some embodiments, electrospinning a polymer solution on to a v-shaped rotating collector produces pieces of meniscus-shaped electrospun collagen. In some embodiments, the collector is shaped to produce a polymer scaffold composition that mimics a shape and size of a desired body part or portion thereof. In some embodiments, the desired body part is a meniscus. In some embodiments, the rotating collector is cone-shaped. In some embodiments, the rotating collector possesses two ends. In some embodiments, a first end of the rotating collector has a smaller width or diameter than a second end. In some embodiments, the first end of the rotating collector has a similar or the same width or diameter as the second end. In some embodiments, the first end of the rotating collector has a different shape than the second end. In some embodiments, the first end of the rotating collector has a similar or the same shape as the second end. In some embodiments, the width or diameter of an end of the rotating collector is about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm or about 20 cm. In some embodiments, the diameter of an end of the rotating collector is about 25 cm, about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, or about 1 meter.

Device Controller

In some embodiments, the systems further comprise a computer for executing the methods disclosed herein and producing the compositions disclosed herein. In some embodiments, the computer comprise a processor, a memory device, an operating system, and a software module for operating the syringe for electrospinning the polymer solution. In some embodiments, the computer comprise a digital processing device and includes one or more hardware central processing units (CPU) that carry out the controllers' functions. In further embodiments, the system includes an operating system configured to perform executable instructions. In some embodiments, the operating system is software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®). In some embodiments, the system includes a storage and/or memory device. In some embodiments, the storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the device is a storage device including, by way of non-limiting examples, CD-ROMs, DVDs, flash memory devices, magnetic disk drives, magnetic tapes drives, optical disk drives, and cloud computing based storage. In some embodiments, the storage and/or memory device is a combination of devices such as those disclosed herein. In some embodiments, the systems described herein include user interfaces. In further embodiments, the user interfaces include graphic user interfaces (GUIs). In still further embodiments, the user interfaces are interactive and present a user with menus and options for interacting with the systems and printheads described herein. In further embodiments, the system includes a display screen to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of displays such as those disclosed herein. In still further embodiments, the device includes an input device to receive information from a user. In some embodiments, the input device is a keyboard. In further embodiments, the input device is a key pad. In a particular embodiment, the input device is a simplified key pad for use by a subject with communications limitations (e.g., due to age, infirmity, disability, etc.), wherein each key is associated with a color, a shape, and health/communication concept. In some embodiments, the input device is a pointing device including, by way of non-limiting examples, a mouse, trackball, track pad, joystick, game controller, or stylus. In some embodiments, the input device is the display screen, which is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein. In some embodiments, the systems, and software modules disclosed herein are intranet-based. In some embodiments, the systems and software modules are Internet-based. In further embodiments, the systems and software modules are World Wide Web-based. In still further embodiments, the systems and software modules are cloud computing-based. In other embodiments, the systems and software modules are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof.

In some embodiments, the systems further comprise a photocrosslinking device.

Methods of Treatment

Disclosed herein, in some embodiments, are methods of treating a tissue defect in a subject comprising administering to the subject a polymer scaffold composition disclosed herein. In some embodiments, the polymer scaffold composition comprises a plurality of polymer fibers, wherein the polymer fibers are electrospun and crosslinked. In some embodiments, the polymer fibers consist essentially of collagen. In some embodiments, the polymer fibers comprise a shell. In some embodiments, the shell comprises collagen. In some embodiments, the shell consists essentially of collagen. In some embodiments, the polymer fibers comprise a core. In some embodiments, the core comprises polylactic acid.

Further disclosed herein, in some embodiments, are methods of treating a tissue defect in a subject comprising administering to the subject a cell-seeded polymer scaffold composition disclosed herein. Further disclosed herein, in some embodiments, are methods of treating a tissue defect in a subject comprising administering to the subject a cell-seeded multilayer construct disclosed herein. In some embodiments, the polymer scaffold composition comprises a plurality of polymer fibers, wherein the polymer fibers are electrospun and crosslinked. In some embodiments, the tissue defect comprises a joint defect. In some embodiments, the polymer fibers consist essentially of collagen. In some embodiments, the polymer fibers comprise a shell. In some embodiments, the shell comprises collagen. In some embodiments, the shell consists essentially of collagen. In some embodiments, the polymer fibers comprise a core. In some embodiments, the core comprises polylactic acid.

In some embodiments, the joint defect comprises or comprised articular cartilage. In some embodiments, the articular cartilage is worn, eroded, damaged, torn, degraded, degenerated, frayed, scarred or deteriorated. In some embodiments, the articular cartilage is a meniscus or portion thereof. In some embodiments, the meniscus is to provide a cushion between a femur condyle and a tibia. In some embodiments, the methods of treating the tissue defect comprises administering the polymer scaffold composition between the femur condyle and the tibia. In some embodiments, the cell-seeded polymer scaffold composition prevents cartilage loss from the meniscus. In some embodiments, the cell-seeded polymer scaffold composition prevents damage to the meniscus, femur condyle or tibia. One skilled in the art would appreciate that these methods could be applied to similar joints and conditions.

In some embodiments, the tissue defect is due to a disease or condition. In some embodiments, the disease or condition comprises osteoarthritis. In some embodiments, the disease or condition comprises deterioration of a joint. In some embodiments, the disease or condition comprises a joint defect or a joint injury. In some embodiments, the joint is located in an elbow, a wrist, a neck, a jaw, a clavicle, a shoulder blade, a hip, a shoulder, a knee, an ankle, a foot, a spinal column, a finger or a toe. In some embodiments, the joint injury comprises a knee injury. In some embodiments, the joint injury comprises a meniscus lesion. In some embodiments, the disease or condition comprises a discoid meniscus. In some embodiments, the subject is in need of a meniscus transplant. In some embodiments, the subject has had a menisectomy.

In some embodiments, the disease or condition is selected from rheumatoid arthritis, gout, pseudo-gout, septic arthritis, ankylosing spondylitis, juvenile idiopathic arthritis, Still's disease, lupus, infections arthritis, psoriasis, reactive arthritis, Ehlers-Danlos Syndrome, haemochromatosis, hepatitis, Lyme disease, Crohn's disease, ulcerative colitis, Henoch-Schonlein purpura, hyperimmunoglobulinemia D, sarcoidosis, TNF receptor associated periodic syndrome, Wegener's granulomatosis, familial Mediterranean fever, systemic lupus erythematosus, achondroplasia, costochondritis, or relapsing polychondritis. In some embodiments, the subject has a spinal disc herniation, a chondroma, a chondrosarcoma and a pleomorphic adenoma.

In some embodiments, the disease or condition comprises an arthropathy. In some embodiments, the arthropathy is selected from spondylarthropathy, reactive arthropathy, enteropathic arthropathy, crystal arthropathy, diabetic arthropathy, neuropathic arthropathy.

In some embodiments, the disease or condition is obesity. In some embodiments, the condition is aging. In some embodiments, the condition is a burn. In some embodiments, the condition is an amputation. In some embodiments, the condition is a birth defect or a congenital defect. In some embodiments, the disease or condition is an autoimmune disease.

In some embodiments, the condition is selected from a musculoskeletal trauma, a sport injury, an automobile accident, an infection or a tumor.

In some embodiments, the methods of treating the tissue defect further comprise deriving the plurality of cells from the subject in an effort to avoid an immune response or a tissue rejection. In some embodiments, the methods further comprise deriving the plurality of cells from a second subject. In some embodiments, the subject is human. In some embodiments, the methods of treating a tissue defect further comprise deriving the plurality of cells from a non-human animal. In some embodiments, the animal is selected from a human, a cow, a horse, a sheep, a goat, a chimpanzee, a monkey, a rat, a pig, a mouse and a rabbit. In some embodiments, the animal is a pig.

In some embodiments, the methods of treating a tissue defect further comprise active joint motion, wherein the active joint motion prevents restrictive adhesions and scar tissue formation. In some embodiments, the methods further comprise a tissue remodeling activity. In some embodiments, the tissue remodeling activity is selected from neo-tissue formation, extracellular matrix deposition, extracellular matrix formation and integration of host tissue with the polymer scaffold composition.

Polymer Solution

Disclosed herein, in some embodiments, are methods and systems for electrospinning a polymer solution. In some embodiments, the polymer solution comprises a protein. In some embodiments, the polymer solution comprises a carbohydrate. In some embodiments, the carbohydrate is a glycosaminoglycan. In some embodiments, the polymer solution comprises an aliphatic polyester. In some embodiments, the aliphatic polyester is selected from polylactic acid, polycaprolactone, a copolymer thereof or a blend thereof. In some embodiments, the polymer solution comprises a biodegradable polymer. In some embodiments, the polymer solution comprises a polymer selected from a collagen, chitosan, gelatin, latex, dextran, fibroin, keratin, poly(lactic acid-co-glycolic acid), polyglycolic acid, polydiaxanone, poly(propylene carbonate), poly(ethylene oxide), poly(ester-urethane)urea, poly(lactide-co-caprolactone) or a combination thereof. In some embodiments, the polymer solution comprises a chitosan-poly(L-lactic acid-co-s-caprolactone blend. In some embodiments, the polymer solution comprises a polylactic acid-gelatin blend. In some embodiments, the polymer solution comprises a polylactic acid-keratin blend. In some embodiments, the polymer solution comprises a gelatin-hydroxyapatite blend. In some embodiments, the polymer solution comprises hyaluronic acid or a derivative thereof. In some embodiments, the polymer solution comprises a copolymer of caprolactone and ethyl ethylene phosphate. In some embodiments, the polymer solution comprises polylactic acid. In some embodiments, the polymer solution comprises polylactic acid dissolved in a mixed solvent of dichloromethane and N,N-dimethylacetamide.

In some embodiments the polymer solution comprises a biocompatible polymer. In some embodiments, the biocompatible polymer comprises collagen. In some embodiments, the collagen is selected from type I collagen, type II collagen, type III collagen, type IV collagen, type V collagen, type VI collagen, type VII collagen, type VIII collagen, type IX collagen, type X collagen, type XI collagen, type XII collagen, type XIII collagen, type XIV collagen, type XV collagen, type XVI collagen, type XVII collagen, type XVIII collagen, type XIX collagen, type XX collagen, type XXI collagen, type XXII collagen, type XXIII collagen, type XXIV collagen, type XXV collagen, type XXVI collagen, type XXVII collagen, type XXVIII collagen and a combination thereof.

In some embodiments, the polymer solution consists essentially of one type of polymer. In some embodiments, the polymer consists essentially of collagen (e.g. a collagen solution). In some embodiments, the polymer solution consists essentially of collagen and does not include any other polymer. In some embodiments, the polymer is about 90%, about 92%, about 94%, about 96%, about 98%, about 99% or about 100% pure collagen. In some embodiments, the polymer is essentially pure collagen. In some embodiments, the collagen comprises methacrylated collagen. In some embodiments, the collagen is dissolved in a solvent selected from PBS, ethanol, water, hexafluoro-2-propanol (HFIP) and a combination thereof. In some embodiments, the collagen is dissolved in a PBS/ethanol mixture. In some embodiments, the collagen is dissolved in water. In some embodiments, the collagen is dissolved in HFIP. In some embodiments, the collagen solution provides for a polymer scaffold composition comprising polymer fibers consisting essentially of collagen (e.g. a collagen scaffold composition). In some embodiments, the collagen scaffold composition is capable of being administered to a subject.

In some embodiments, the polymer scaffold composition consisting essentially of one type of polymer, wherein the polymer is collagen, is non-toxic to the subject. In some embodiments, the polymer scaffold composition consisting essentially of one type of polymer, wherein the polymer is collagen, is less toxic to the subject relative to a polymer scaffold composition comprising a polymer other than collagen. In some embodiments, the polymer scaffold composition consisting essentially of one type of polymer, wherein the polymer is collagen, does not elicit an immune response from the subject. In some embodiments, the polymer scaffold composition consisting essentially of one type of polymer, wherein the polymer is collagen, elicits less of an immune response from the subject than the polymer scaffold composition comprising a polymer other than collagen. In some embodiments, the polymer scaffold composition consisting essentially of one type of polymer, wherein the polymer is collagen, is readily remodeled and/or integrated in the subject. In some embodiments, the collagen is selected from type I collagen, type II collagen, type III collagen, type IV collagen, type V collagen, type VI collagen, type VII collagen, type VIII collagen, type IX collagen, type X collagen, type XI collagen, type XII collagen, type XIII collagen, type XIV collagen, type XV collagen, type XVI collagen, type XVII collagen, type XVIII collagen, type XIX collagen, type XX collagen, type XXI collagen, type XXII collagen, type XXIII collagen, type XXIV collagen, type XXV collagen, type XXVI collagen, type XXVII collagen, type XXVIII collagen and a combination thereof. In some embodiments, the collagen comprises methacrylated collagen.

In some embodiments, the polymer is dissolved to about a 1 wt % solution, about a 2 wt % solution, about a 4 wt % solution, about a 6 wt % solution, about a 8 wt % solution, about a 10 wt % solution, about a 12 wt % solution, about a 14 wt % solution, about a 15 wt % solution, about a 16 wt % solution, about 17 wt % solution, about a 18 wt % solution, about a 19 wt % solution, about a 20 wt % solution, or about a 22 wt % solution. In some embodiments, the polymer solution comprises type I collagen dissolved to a 16 wt % solution.

In some embodiments, the polymer solution comprises polylactic acid dissolved to about a 1 wt % solution, about a 2 wt % solution, about a 4 wt % solution, about a 6 wt % solution, about a 8 wt % solution, about a 10 wt % solution, about a 12 wt % solution, about a 14 wt % solution, about a 15 wt % solution, about a 16 wt % solution, about 17 wt % solution, about a 18 wt % solution, about a 19 wt % solution, about a 20 wt % solution, or about a 22 wt % solution. In some embodiments, the polymer solution comprises polylactic acid dissolved to a 10 wt % solution.

In some embodiments, the polymer solution further comprises a hydrophilic component. In some embodiments, the hydrophilic component is selected from polyethylene glycol and hydroxylapatite. In some embodiments, the polymer is conjugated to biotin. In some embodiments, the collector comprises avidin.

In some embodiments, the polymer solution further comprises an extracellular matrix component. In some embodiments, by non-limiting example, the extracellular matrix component is selected from a nidogen, an entactin, a laminin, an integrin, a dystroglycan, a proteoglycan, a perlecan, a fibrillin, a substrate adhesion molecule, and a combination thereof.

In some embodiments, the polymer solution further comprises an enzyme. In some embodiments, the enzyme is a protease. In some embodiments, the protease is selected from a serine protease, a cysteine protease, a threonine protease, a metalloprotease and a collagenase.

In some embodiments, the polymer solution comprises a salt. In some embodiments, by non-limiting example, the salt is selected from a manganese salt, a phosphorus salt, a magnesium salt and a calcium salt.

The Polymer Fibers

Disclosed herein, in some embodiments, are compositions comprising polymer fibers and methods and systems for the production of polymer fibers. In some embodiments, the polymer fibers possess an average diameter of between about 1 nm and 10 nm, between about 10 nm and 20 nm, between about 20 nm and 30 nm, between about 30 nm and 40 nm, between about 40 nm and 50 nm, between about 60 nm and 70 nm, between about 70 nm and 80 nm, between about 80 nm and 90 nm, between about 90 nm and 100 nm, between about 100 nm and 200 nm, between about 200 nm and about 300 nm, between about 300 nm and 400 nm, between about 400 nm and 500 nm, between about 500 nm and 600 nm, between about 600 nm and 700 nm, between about 700 nm and 800 nm, between about 800 nm and 900 nm, between about 900 nm and 1000 nm. In some embodiments, polymer fibers possess an average diameter of between about 100 nm and 1000 nm.

In some embodiments, the polymer fibers possess an average ultimate tensile strength of less than 1 MPa. In some embodiments, the polymer fibers possess an average ultimate tensile strength of between about 0.1 MPa to about 2000 MPa after crosslinking. In some embodiments, the polymer fibers possess an average ultimate tensile strength of between about 0.1 MPa to about 1000 MPa after crosslinking. In some embodiments, the polymer fibers possess an average ultimate tensile strength of between about 1 MPa to about 500 MPa after crosslinking. In some embodiments, the polymer fibers possess an average ultimate tensile strength of between about 1 MPa to about 100 MPa after crosslinking. In some embodiments, the polymer fibers possess an average ultimate tensile strength of between about 1 MPa to about 10 MPa after crosslinking. In some embodiments, the polymer fibers possess an average ultimate tensile strength of between about 10 MPa to about 20 MPa, between about 20 MPa to about 30 MPa, between about 30 MPa to about 40 MPa, between about 40 MPa to about 50 MPa, between about 50 MPa to about 60 MPa, between about 60 MPa to about 70 MPa, between about 70 MPa to about 80 MPa, between about 80 MPa to about 90 MPa, between about 90

MPa to about 100 MPa, between about 100 MPa to about 110 MPa, between about 110 MPa to about 120 MPa, between about 120 MPa to about 130 MPa, between about 130 MPa to about 140 MPa, between about 140 MPa to about 150 MPa, between about 150 MPa to about 160 MPa, between about 160 MPa to about 170 MPa, between about 170 MPa to about 180 MPa, between about 180 MPa to about 190 MPa, between about 190 MPa to about 200 MPa, about 250 MPa, about 300 MPa, about 350 MPa, about 400 MPa or about 500 MPa after crosslinking.

In some embodiments, the polymer fibers comprise polylactic acid fibers. In some embodiments, the polylactic acid fibers are randomly oriented polylactic acid fibers. In some embodiments, the randomly oriented polylactic acid fibers possess an average ultimate tensile strength of between about 25 MPa and about 90 MPa after crosslinking.

In some embodiments, the polymer fibers comprise polylactic acid. In some embodiments, the polylactic acid fibers are aligned. In some embodiments, the aligned polylactic acid fibers possess an average ultimate tensile strength of between about 125 MPa and about 325 MPa after crosslinking.

In some embodiments, the polymer fibers comprise collagenous fibers, elastic fibers, reticular fibers or a combination thereof. In some embodiments, the collagenous fibers comprise alpha polypeptide chains. In some embodiments, the elastic fibers comprise elastic microfibril and elastin. In some embodiments, the reticular fibers comprise type III collagen.

Cells

Disclosed herein, in some embodiments, are methods, compositions and systems comprising a cell or a use thereof. In some embodiments, the plurality of cells are selected from keratinocytes, exocrine secretory epithelial cells, hormone secreting cells, epithelial cells, neural or sensory cells, photoreceptor cells, muscle cells, extracellular matrix cells, blood cells, cardiovascular cells, endothelial cells, vascular smooth muscle cells kidney cells, pancreatic cells, immune cells, stem cells, germ cells, nurse cells, interstitial cells, stellate cells liver cells, gastrointestinal cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblasts, myofibroblasts, Schwann cells, adipose cells, bone cells, bone marrow cells, cartilage cells, pericytes, mesothelial cells, cells derived from endocrine tissue, stromal cells, progenitor cells, lymph cells, endoderm-derived cells, ectoderm-derived cells, mesoderm-derived cells, pericytes, progenitors thereof and a combination thereof.

In some embodiments, the plurality of cells are selected from cartilaginous cells, chondrocytes, chondroblasts, connective tissue fibroblasts, tendon fibroblasts, bone marrow reticular tissue fibroblasts, nonepithelial fibroblasts, pericytes, osteoprogenitor cells, osteoblasts, osteoclasts, meniscal cells or a combination thereof.

In some embodiments, the plurality of cells comprises cartilaginous cells. In some embodiments, the cartilaginous cells are vascular. In some embodiments, the cartilaginous cells are avascular. In some embodiments, the plurality of cells comprises meniscal cells. In some embodiments, the meniscal cells are vascular. In some embodiments, the meniscal cells are avascular.

In some embodiments the plurality of cells is derived from or isolated from a tissue. In some embodiments, the tissue comprises a connective tissue. In some embodiments, the connective tissue comprises cartilage. In some embodiments, the connective tissue comprises tendon. In some embodiments, the connective tissue comprises ligament. In some embodiments, the connective tissue comprises fascia. In some embodiments, the connective tissue comprises dura mater.

In some embodiments, the plurality of cells are selected from stem cells, bone marrow stem cells, progenitor cells, totipotent cells, pluripotent cells, induced pluripotent stem cells, undifferentiated cells, differentiated cells, differentiating cells, trans-differentiating cells, cells from an adult, cells from a child, germ cells, umbilical cells, circulating cells, resident cells, adherent cells, malignant cells, tumor cells, proliferating cells, quiescent cells, senescent cells, apoptotic cells, cytokine-producing cells, migrating cells and a combination thereof.

In some embodiments, the plurality of cells expresses cell adhesion molecules. In some embodiments, cell adhesion molecules are selected from one or more of an adherin, a cadherin, a calsyntenin, a claudin, a cluster differentiation protein, a contactin, an immunoglobulin, an integrin, a lectin, a nectin, an occludin, a vinculin, a porimin, a podoplanin, a podocalyxin, a periostin, a neurotrimin, a neurexin, and a selectin. In some embodiments, the cell adhesion molecule is a receptor. In some embodiments, the cell adhesion molecule is a transmembrane protein.

In some embodiments, the plurality of cells comprise genetically modified cells. In some embodiments, the genetically modified cells are genetically modified by transient transfection of a nucleic acid. In some embodiments, transient transfection is selected from calcium phosphate transfection, liposome transfection, electroporation, lipofection or sono-poration. In some embodiments, the genetically modified cells are genetically modified by a retrovirus, an adenovirus or an adeno-associated virus transducing the nucleic acid. In some embodiments, the nucleic acid is selected from a vector, a plasmid, a gene, a non-coding nucleic acid, an exon, an intron, a double stranded DNA, a single stranded DNA, a RNA, a siRNA or a miRNA. In some embodiments, the nucleic acid comprises a gene. In some embodiments, the gene is a eukaryotic gene. In some embodiments, the gene is a prokaryotic gene.

In some embodiments, the plurality of cells comprises a genetic mutation. In some embodiments, the plurality of cells comprises a naturally-occurring genetic mutation. In some embodiments, the naturally-occurring genetic mutation is a germline genetic mutation or a somatic genetic mutation. In some embodiments, the plurality of cells comprises an induced genetic mutation. In some embodiments, the induced genetic mutation comprises a random genetic mutation or a targeted genetic mutation. In some embodiments, one or more genes in the plurality of cells comprise a genetic mutation. In some embodiments, 1, 2, 3, 4, 5, 6, 7, 8, 9 or 10 genes in the plurality of cells comprise a genetic mutation. In some embodiments, more than 10 genes in the plurality of cells comprise a genetic mutation. In some embodiments, a gene comprises a plurality of genetic mutations.

In some embodiments, the plurality of cells expresses a tag, a marker or a protein with detectable enzymatic activity. In some embodiments, the tag is a fluorescent protein. In some embodiments, the fluorescent protein is mPlum, mCherry, tdTomato, mStrawberry, J-Red, DsRed-monomer, mOrange, mKO, mCitrine, Venus, YPet, EYFP, Emerald EGFP, CyPet, mCFPm, Cerulean, T-Sapphire, GFP or YFP. In some embodiments the tag is a peptide. In some embodiments, the peptide is myc-tag, c-myc tag, FLAG-tag, His-tag, polyhistidine tag, HA-tag, V5, VSVG, softag 1, softag 3, express tag, S tag, fluorescein isothiocyanate (FITC), dinitrophenyl, trinitrophenyl, peridinin chlorophyll protein complex, green fluorescent protein (GFP), red fluorescent protein (RFP), biotin, phycoerythrin (PE), streptavidin, avidin, horse radish peroxidase (HRP), alkaline phosphatase, glucose oxidase, glutathione-S-transferase (GST), SUMO tag, thioredoxin, poly(NANP), poly-Arg, calmodulin binding protein, PurF fragment, ketosteroid isomerase, PaP3.30, TAF12 histone fold domain, maltose binding protein, a bead, and a combination or portion thereof. In some embodiments, the marker is palmitoylation, myristoylation, glycosylation or nitrosylation.

Cell Solution

In some embodiments, the plurality of cells is in a cell solution. In some embodiments, the plurality of cells is suspended in the cell solution. In some embodiments, the plurality of cells is suspended in the cell solution prior to adding the plurality of cells to the polymer scaffold composition. In some embodiments, the plurality of cells is suspended in the cell solution prior to electrospraying. In some embodiments, the cell solution is selected from a biogel, hydrogel, biomimetic gel, cell culture medium, buffer solution, saline solution or biological medium.

In some embodiments, by non-limiting example, the cell solution comprises a cell culture medium. In some embodiments, the cell culture medium is selected from Balanced Salts, Dulbecco's Modified Eagle's Medium, Dulbecco's Modified Eagle's Medium/Nutrient F-12 Media, Ham's F-10 Media, Ham's F-12 Media, Minimum Essential Medium Eagle, Medium 199, RPMI-1640 Medium, Ames' Media, BGJb Medium (Fitton-Jackson Modification), Click's Medium, CMRL-1066 Medium, Fischer's Medium, Glasgow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E and a combination thereof. In some embodiments, the cell culture medium comprises a biological serum. In some embodiments, the biological serum comprises fetal bovine serum, fetal calf serum, fetal goat serum, horse serum or a combination thereof. In some embodiments, the biological serum content of the cell culture medium is about 0.5% v/v, about 1% v/v, about 2% v/v, about 5% v/v, about 10% v/v, about 15% v/v, about 20% v/v, about 50% v/v, about 99% v/v, or about 100% v/v. In some embodiments, the cell culture medium comprises a buffering agent. In some embodiments, by non-limiting example, the buffering agent is selected from MES, ADA, PIPES, ACES, MOPSO, MOPS, BES, TES, HEPES, DIPSO, Acetamidoglycine, TAPSO, POPSO, HEPPSO, HEPPS, Tricine, Glycinamide, Bicine, TAPS and a combination thereof.

In some embodiments, the cell solution comprises a biomimetic gel. As used herein, in some embodiments, the terms biomimetic gel, biogel and hydrogel are used interchangeably. In some embodiments, the biomimetic gel comprises a polymer. In some embodiments, by non-limiting example, the polymer is selected from polyethylene glycol (PEG), a PEG macromer, polyethylene glycol methacrylate (PEGMA), polyethylene dimethacrylate (PEGDMA), poly (hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, PEG-glycolide or a combination thereof. In some embodiments, the biomimetic gel comprises a PEGDMA hydrogel. In some embodiments, the PEGDMA hydrogel is a 10% w/v PEGDMA hydrogel. In some embodiments, the PEGDMA hydrogel is a 20% w/v PEGDMA hydrogel. In some embodiments, the biomimetic gel does not comprise a polymer. In some embodiments, the PEG macromer comprises a reactive chain end such as acrylate, methacrylate, allyl ether, maleimide, vinyl sulfone, NHS ester and a vinyl ether group. In some embodiments, an alcohol chain ends of a PEG is esterified by an acid chloride (e.g., acryloyl chloride, methacryloyl chloride) in the presence of a base. In some embodiments, a PEG chain end is etherified under basic conditions by a reaction with an alkyl halide such as 2-chloroethyl vinyl ether or allyl bromide. In some embodiments, the acrylate, methacrylate, vinyl sulfone, maleimide, vinyl ether and allyl ether are capable of step growth network formation or polymerization. In some embodiments, polymerization is initiated using redox-generated radicals (e.g., ammonium persulfate and TEMED), or radicals generated with light.

In some embodiments, the biomimetic gel further comprises alginate, Matrigel, hyaluronan, fibrinogen, chondroitin sulfate, glycerol, cellulose, agarose, gelatin, chitosan, paraffin, silica, fibrin or a combination thereof. In some embodiments, the biomimetic gel comprises a peptide, an amino acid, a dipeptide, a proteoglycan, a glycoprotein, a surfactant, a starch, or a combination thereof.

In some embodiments, the cell solution comprises a glycoprotein. In some embodiments, the glycoprotein comprises lubricin. In some embodiments, the cell solution comprises a joint lubricant. In some embodiments, the joint lubricant comprises gelatin, heparin, synovial fluid or a combination thereof.

In some embodiments, the cell solution comprises a protein, a peptide, a salt, a pH buffer, an extracellular matrix component, a chemical, a biochemical factor, a polysaccharide, a drug and a carboxylic acid.

In some embodiments, by non-limiting example, the drug is selected from an antibiotic and/or an antimycotic. In some embodiments, by non-limiting example, the antibiotic is selected from penicillin, streptomycin, actinomycin D, ampicillin, blasticidin, carbenicillin, cefotaxime, fosmidomycin, gentamicin, kanamycin, neomycin, polymyxin B and a combination thereof. In some embodiments, by non-limiting example, the antimycotic is selected from amphotericin B, nystatin, natamycin and a combination thereof. In some embodiments, by non-limiting example, the drug is an anti-inflammatory drug. In some embodiments, the anti-inflammatory drug is a non-steroidal anti-inflammatory drug (NSAID). In some embodiments, by non-limiting example, the NSAID is selected from a salicylic acid, an acetylsalicylic acid, an ibuprofen, an ibuprofen lysine, a deflunisal, a salsalate, a choline magnesium trisalicylate, a naproxen, a fenoprofen, a ketoprofen, a dexketoprofen, a flubiprofen, a exaprozin, a loxoprofen, an indomethacin, a tolmetin, a sulindac, an etodolac and a sulfonanilide. In some embodiments, the non-steroidal anti-inflammatory drug is a cyclooxygenase (COX) inhibitor. In some embodiments, the COX inhibitor is selected from a COX1 inhibitor, a COX2 inhibitor and a combination thereof. In some embodiments, the COX inhibitor is acetaminophen or a derivative thereof. In some embodiments, the anti-inflammatory drug is a steroid. In some embodiments, by non-limiting example, the steroid is selected from a glucocorticoid, a prednisone, a methylprednisone, a prednisolone, a medrol, a beclomethsone, a budesonide, a flunisolide, a fluticasone and a triamcinolone.

In some embodiments, by non-limiting example, the cell solution comprises a protein and/or a peptide. In some embodiments, the protein and/or peptide is selected from a hormone, a growth factor, a protease, an enzyme, a kinase, a cytokine, a chemokine, a structural protein, a ligand and a combination thereof.

In some embodiments, by non-limiting example, the growth factor is selected from Adrenomedullin (AM), Angiopoietin (Ang), Autocrine motility factor, Bone morphogenetic proteins (BMPs), Brain-derived neurotrophic factor (BDNF), Colony-stimulating factor (CSF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), insulin, Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-alpha), Transforming growth factor beta (TGF-beta), Tumor necrosis factor-alpha (TNF-α), Vascular endothelial growth factor (VEGF), placental growth factor (PlGF), Foetal Bovine Somatotrophin and a combination thereof. In some embodiments, the growth factor is TGF-beta.

In some embodiments, TGF-beta possesses a concentration of about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL or about 20 ng/mL. In some embodiments, the TGF-beta is present at a concentration of about 50 ng/mL, about 100 ng/mL, about 200 ng/mL, about 300 ng/mL, about 400 ng/mL, about 500 ng/mL, or about 1 µg/mL in the cell culture medium. In some embodiments, TGF-beta is possesses a concentration of 10 ng/ml of the cell culture media.

In some embodiments, the protein is selected from type II collagen, chondroitin sulfate, hyaluronan and a combination thereof. In some embodiments, the protein is an enzyme. In some embodiments, the enzyme is a protease. In some embodiments, by non-limiting example, the protease is selected from a serine protease, a threonine protease, a cysteine protease, an aspartate protease, a glutamic acid protease, a metalloprotease, an exopeptidase, an endopeptidase, a trypsin, a chymotrypsin, a pepsin, a papain, an elastase, a carboxypeptidase, an aminopeptidase, a thrombin, a plasmin, a cathepsin or snake venom. In some embodiments, the protease is a collagenase.

In some embodiments, the cell solution comprises a support material. In some embodiments, the support material comprises an extracellular matrix component or fragment thereof. In some embodiments, by non-limiting example, the extracellular matrix component is selected from a nidogen, an entactin, a laminin, an integrin, a dystroglycan, a perlecan, a fibrillin, a fibrin, a fibronectin, a substrate adhesion molecule, and a combination thereof.

In some embodiments, the extracellular matrix component is derived from a human, a cow, a horse, a sheep, a goat, a chimpanzee, a monkey, a rat, a pig, a mouse, a rabbit or a synthetic reaction.

In some embodiments, the cell solution comprises a cellular differentiation agent. In some embodiments, the cell solution comprises a cell culture supernatant or a cell culture conditioned media.

In some embodiments, the plurality of cells possess a density in the cell solution of less than one cell per milliliter.

In some embodiments, the plurality of cells possess a density in the cell solution of less than about 10 cells/mL. In some embodiments, the plurality of cells possess a density in the cell solution of less than about 100 cells/mL. In some embodiments, the plurality of cells possess a density in the cell solution of about 100 cells/mL, about 200 cells/mL, about 300 cells/mL, about 400 cells/mL, about 500 cells/mL, about 600 cells/mL, about 700 cells/mL, about 800 cells/mL, about 900 cells/mL or about 1,000 cells/mL. In some embodiments, the plurality of cells possess a density in the cell solution of more than 1,000 cells/mL. In some embodiments, the plurality of cells possess a density in the cell solution of about 10,000, about 15,000, about 20,000, about 25,000, about 30,000, about 35,000, about 40,000, about 45,000, about 50,000, about 55,000, about 60,000, about 65,000, about 70,000, about 75,000, about 80,000, about 85,000, about 90,000, about 95,000 or about 100,000 cells per milliliter. In some embodiments, the plurality of cells possess a density in the cell solution of more than 100,000 cells/mL. In some embodiments, the plurality of cells possess a density in the cell solution of about 50,000 cells per milliliter.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are employed in practicing the invention. It is intended that the following claims define the scope of the invention and that methods and structures within the scope of these claims and their equivalents be covered thereby.

EXAMPLES

Example 1

Electrospinning a Nanofibrous, Biodegradable and Biomimetic Scaffold with Aligned Fibers from a Polylactic Acid (PLA) Solution In the present study, a nanofibrous matrix of PLA was electrospun into a biodegradable and biomimetic scaffold. The PLA nanofibrous scaffold was aligned by directing fiber deposition onto a rotating collector, with the degree of alignment controlled by the rotating speed of the collector. This controllable scaffold in turn determined the anisotropic mechanical properties of the scaffolds. To assay the cytocompatibility and cell behavior of electrospun PLA nanofibers, meniscus cells of normal human vascular and avascular regions were seeded on the PLA nanofibrous matrix. Multilayer constructs were then formed and characterized by histology.

Materials and Methods

Fabrication of Poly Lactic Acid (PLA) Scaffolds

PLA (Mw=100,000, NatureWorks LLC, USA) was dissolved in a mixed solvent of dichloromethane and N,N-dimethylacetamide (DMAc) (8/2 w/w) by stirring for 48 h at room temperature to obtain homogeneous 10 wt % solution. The PLA solution was loaded in a syringe, which was driven by a syringe pump (KDS200, KD Scientific Inc., USA) at a feeding rate of 2.0 mL/h. A Teflon tube was used to connect the syringe and a 21-G needle (inner diameter of 0.5 mm), which was set up horizontally. A voltage regulated DC power supply (NNC-30 kV-2 mA portable type, NanoNC, South Korea) was used to apply a voltage varying from 15 to 20 kV to the PLA solution to generate the polymer jet. The electrospun fibers were deposited in the form of a web on collectors covered by aluminum foil. For collecting random fibers, the tip-to-collector distance (TCD) was set to 16 cm on a flat plate as a collector. For collecting aligned fibers, a rotating drum collector (~2400 rpm) was placed at 12 cm from the tangent of the drum to the needle tip. An overview of the systems used to generate random and aligned electrospun scaffolds is shown in FIGS. 6A and 6B.

Assessment of Structural Morphology of PLA Scaffolds

The morphology of electrospun PLA scaffolds was studied under scanning electron microscopy (SEM) (Philips XL30, FEI Co., Andover, Mass.) with an accelerating voltage of 10 kV. Scaffolds were coated with iridium using a sputter coater (Emitech K575X, EM Technologies Ltd, England). The diameter of individual electrospun fibers was measured from the SEM images using image processing software (Image J, National Institutes of Health, USA).

Tissues and Cell Isolation

Normal human menisci (medial and lateral) were obtained from tissue banks (with Scripps Institutional Review Board approval), from 6 donors (mean age: 29.8±4.7; age range: 23-35 years; 2 females, 4 males). Normal menisci were selected following a previously reported macroscopic and histologic grading system (Pauli, et al., 2011). The outer ⅓ (avascular region) and the inner ⅔ of the meniscus (vascular region) was separated with a scalpel and enzymatically digested using collagenase (2 mg/mL; C5138, Sigma-Aldrich, St. Louis, Mo.) in DMEM (Mediatech Inc, Manassas, Va.) and 1% Penicillin-Streptomycin-Fungizone (Life Technologies, Carlsbad, Calif.) for 5-6 hours. The digested tissues were filtered through 100 μm cell strainers (BD Biosciences, San Jose, Calif.) and seeded in monolayer culture in DMEM (Mediatech) supplemented with 10% calf serum (Omega Scientific Inc. Tarzana, Calif.) and 1% Penicillin/Streptomycin/Gentamycin (Life Technologies). Cells were cultured for 1 passage before use in scaffold seeding experiments.

Cell Cultures on Single Layered ES PLA Scaffolds

Human cells from avascular or vascular regions of the meniscus were separately seeded onto random and aligned PLA scaffolds at a density of $1 \times 10^6$ per mL in 6-well plates. Cells were cultured in DMEM supplemented with 10% calf serum and 1% Penicillin, Streptomycin, and Gentamycin for 3-5 days to permit cell attachment and scaffold colonization. Subsequently, the medium was changed to serum free ITS+ medium (Sigma-Aldrich) supplemented with 10 ng/mL TGF beta 1 (PeproTech, Rocky Hill, N.J.). After 2 weeks in culture with medium changes every 3-4 days, the cells on the scaffolds were assessed for cell viability by confocal microscopy and for cell morphology by histology and SEM.

Mechanical Properties of PLA Scaffolds

The mechanical properties of PLA scaffolds were quantified via tensile testing (n=10 per group). Both random and aligned scaffolds were tested under three different conditions: i) freshly electrospun dry scaffolds tested were within 1 day of production; ii) scaffolds were seeded with avascular human meniscus cells and cultured for 1 and 3 weeks; and iii) scaffolds were cultured for 1 and 3 weeks without cells. Electrospun scaffolds were cut into dog-bone shaped specimens with a gauge length of 8 mm and width of 2 mm using a custom punch. The thickness of each scaffold was measured using a digital caliper and reported as mean±standard deviation (SD). For mechanical testing of cultured cell-seeded and acellular scaffolds, human avascular cells (0.5× $10^6$ cells/each sample) were seeded on the dog-bone shaped aligned PLA scaffold. All cultures were in DMEM supplemented with 10% calf serum and 1% Penicillin, Streptomycin, and Gentamycin for 1 day to permit cell attachment and scaffold colonization. Subsequently, the medium was changed to serum free ITS+ medium (Sigma-Aldrich, St. Louis, Mo.) supplemented with 10 ng/mL TGF beta 1 (PeproTech, Rocky Hill, N.J.). After 1 week and 3 weeks in culture with medium changes every 3-4 days, the cell-seeded and non-seeded scaffolds were evaluated for mechanical properties.

The specimens were mounted in the grips of a uniaxial testing machine (Instron® Universal Testing Machine, 3342 Single Column Model; Norwood, Mass.) with a 500 N load cell and tested to failure at a strain rate of 1 mm/sec. Data from samples that failed outside the gauge length were discarded. Young's modulus was calculated from the slope of the linear segment of the stress-strain curve. Ultimate tensile strength (UTS) was calculated at the maximum load before failure. Values were presented as mean±standard deviation.

Mechanical Properties of PLA Scaffolds

Figure 6C:
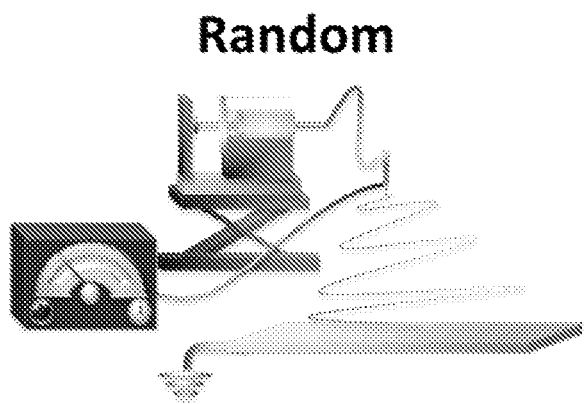
Figure 6C:
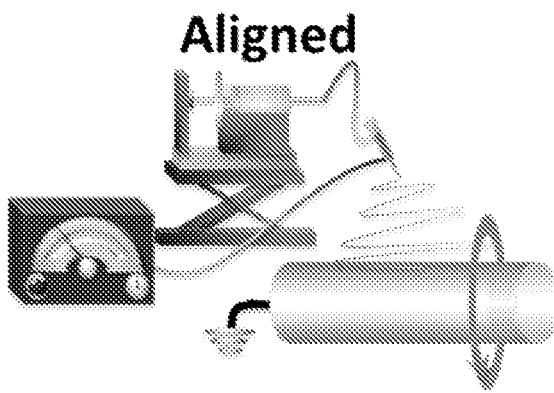
Figure 6C:
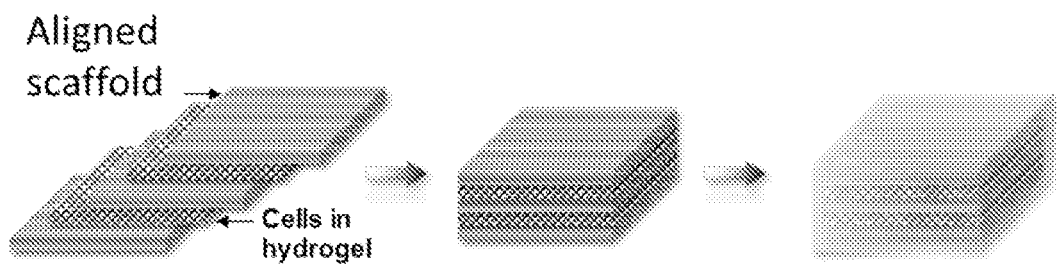

Human avascular meniscus cells (passage 1) were suspended in a hydrogel consisting of collagen type II, chondroitin sulfate and hyaluronan (1 mg each) at $1 \times 10^6$ cells per mL. Cells suspended in hydrogel were seeded onto one aligned PLA scaffold (50 μL), followed by layering another scaffold sheet on top. Another cell layer was applied, followed by a final, third scaffold on the top (FIG. 6C). To stabilize the scaffold layers, a layer of 2% alginate (PRONOVA UP LVG; Novamatrix, Sandvika, Norway) was dispensed over the construct and crosslinked in calcium chloride (120 mM; Sigma-Aldrich) for 20 minutes. Layered constructs were cultured in serum free medium supplemented with TGF beta 1 (10 ng/mL).

Cell Viability Assessments

The viability of cells cultured on PLA scaffolds was observed using the live/dead kit consisting of Calcein-AM and Ethidium Homodimer-1 (Life Technologies) and a laser confocal microscope (LSM-510, Zeiss, Jena, Germany) as previously described (Grogan, et al., 2002).

Cellular Morphology of Avascular Meniscus Cells on Single Layer PLA Scaffolds

SEM was employed to observe high-resolution features of cells grown on the electrospun PLA scaffolds. After a culture time of 7 day and 14 day the cells on the substrates were washed with PBS and fixed with 2.5% w/v glutaraldehyde solution (Sigma-Aldrich) in PBS for 1 h. After fixation they were washed 3 times with PBS for 10 minutes each. Then the cells were dehydrated in a graded series of ethanol (50%, 70%, and 90%) for 30 minutes each and left in 100% ethanol for 24 h at temperatures below minus 4° C. Next, they were kept in 100% ethanol until they were completely dried in a critical point dryer (Autosamdri-815, Series A, Tousimis Inc., Rockville, Md.). Then the dried samples were surface metalized by sputter coating with iridium for SEM examination. The morphology of the scaffolds and the adherent cells was observed by SEM (Philips XL30, FEI Co., Andover, Mass.).

Histology and Immunohistochemistry

PLA scaffold layers seeded with avascular meniscus cells were fixed in Z-Fix (ANATECH, Battle Creek, Mich.) and embedded in paraffin. Sections of 5-7 μm were stained with H&E and Safranin O-Fast Green. For detection of collagen type I by immunohistochemistry, cut sections were treated with hyaluronidase for 2 h (Roberts, et al., 2009) and incubated with a primary antibody against collagen type I (clone: I-8H5; MP Biomedicals, Santa Ma, Calif.) at 10

µg/mL. Secondary antibody staining and detection procedures were followed as previously described (Grogan, et al., 2009). An isotype control was used to monitor nonspecific staining.

RNA Isolation and RT-PCR

Total RNA was isolated from single layer PLA constructs using the RNeasy mini kit (Qiagen, Hilden, Germany) and first strand cDNA was made according to the manufacturer's protocol (Applied Biosystems, Foster City, Calif.). Quantitative RT-PCR was performed using TaqMan® gene expression reagents. COL1A1, aggrecan, SOX9, COMP and GAPDH were detected using Assays-on-Demand™ primer/probe sets (Applied Biosystems). To normalize gene expression levels, GAPDH was employed using the ΔCt method.

Statistical Analysis

Student's t-test was used to assess statistically significance of differences in fiber diameter, mechanical properties, and gene expression levels. P-values less than 0.05 were considered significant.

Results

Controlled Production of Electrospun Random and Aligned PLA Fibrous Scaffolds

The morphological structures of aligned and random electrospun PLA fibers are shown in FIG. 7. The rotating drum speed (~2400 rpm) and delivery parameters used produced scaffold structures with a high degree of alignment (FIG. 7B). The average diameter of aligned fibers was 1.25±0.31 µm (range: 0.46-2.32 µm) and that for random PLA fibers was 1.31±0.56 µm (range: 0.70-3.84 µm). Random scaffolds had a thickness of 0.15±0.04 mm; the thickness of aligned scaffolds was 0.09±0.03 mm.

Cell Morphology and Organization is Dependent on PLA Fiber Orientations

Figure 7A:
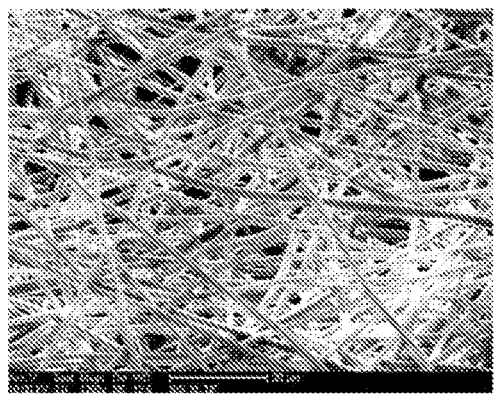
FIG. 7A-F depicts scanning electron micrographs (SEM) of electrospun (ES) PLA scaffolds and cellular response. (A) SEM of randomly oriented and (B) aligned ES PLA fibers (Mag. 1250×). (C) SEM of human meniscus cells cultivated on random (Mag. 625×) and (D) aligned ES PLA fibers Mag. 500×). (E-F) Confocal microscopy demonstrating viability (live/dead) and aligned cells cultivated on random and aligned scaffolds (Mag. 10×).
Figure 7B:
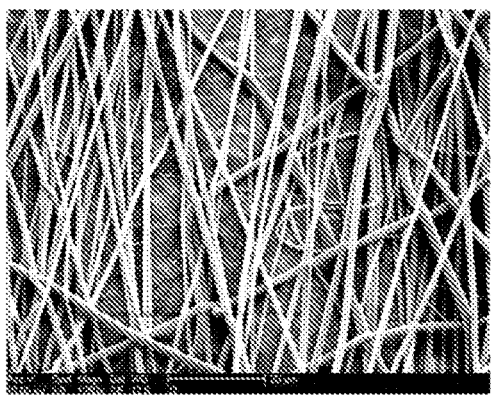
Figure 7C:
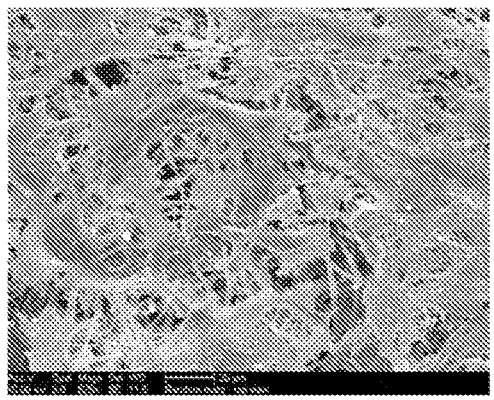
Figure 7D:
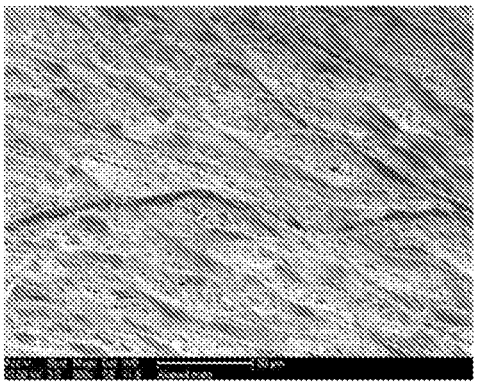
Figure 7E:
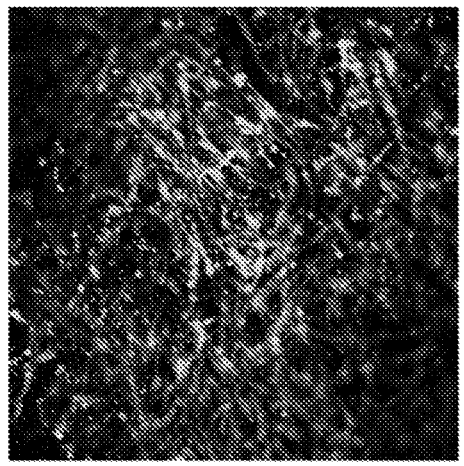
Figure 7F:
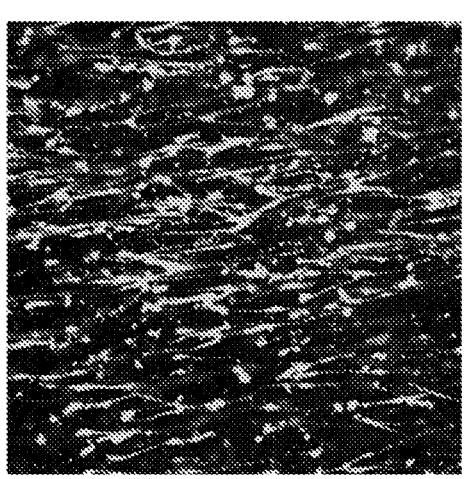

Cells seeded upon randomly spun PLA scaffolds were flattened and spread-out with multi-directional extensions (FIG. 7C), while cells on aligned PLA scaffolds were elongated in line with the direction of the fibers (FIG. 7D). These differences in morphology and alignment were also reflected in the confocal images (FIGS. 7E and 7F), which provided evidence of high cell viability for both scaffolds.

Figure 8A:
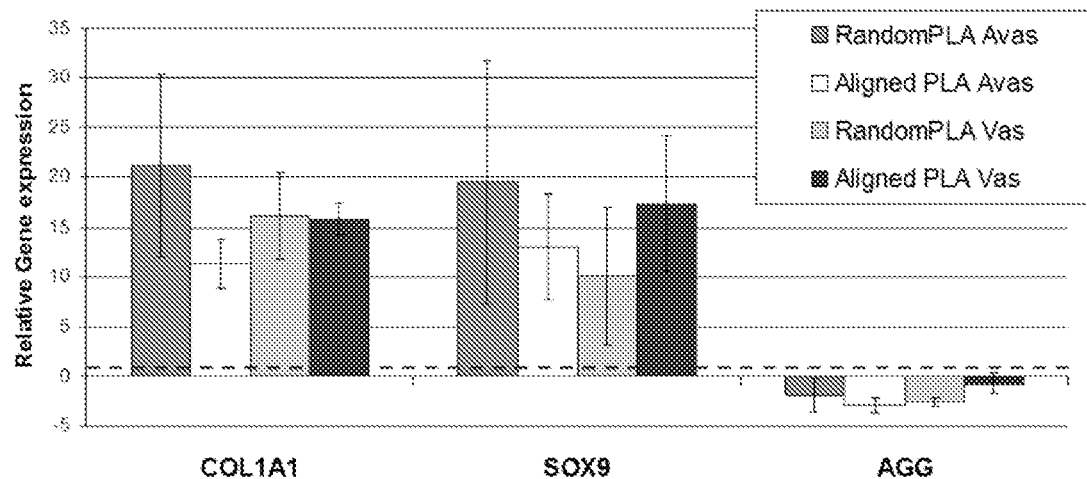
FIG. 8A-B depicts relative fold change in gene expression of human vascular and avascular meniscus cells cultivated on either random or aligned PLA electrospun scaffolds. (A) Increased COL1A1 and SOX9 gene expression. Reduced Aggrecan expression relative to monolayer controls. (B) COMP expression on random and aligned PLA electrospun scaffolds (n=4-5 donors). Expression levels are relative to monolayer controls (dotted line).
Figure 8B:
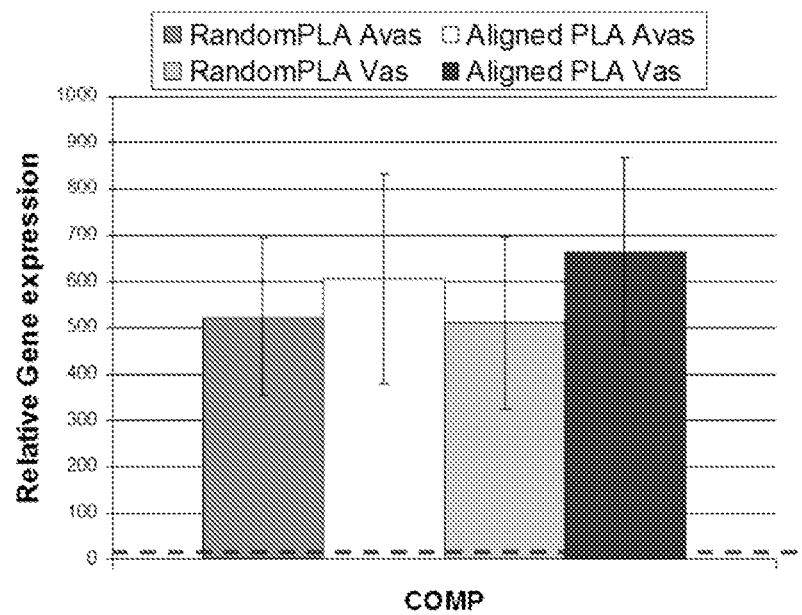
Figure 9A:
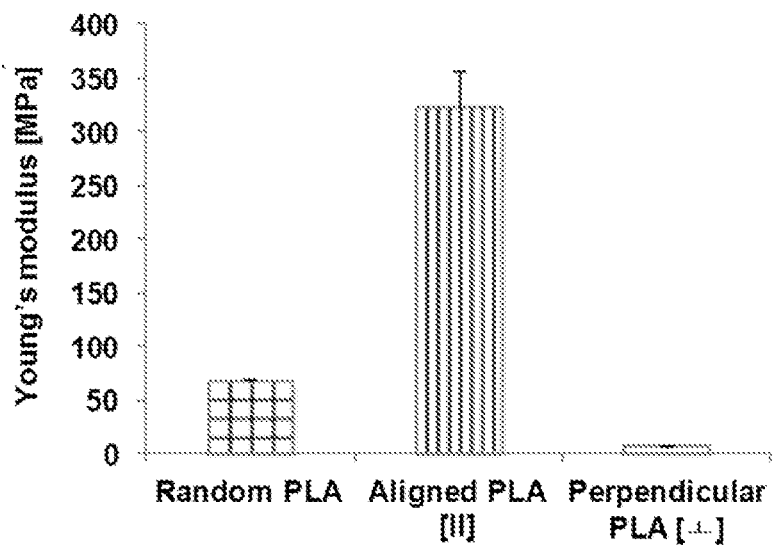
FIG. 9A-F depicts results of mechanical testing of randomly oriented and aligned ES PLA scaffolds. (A) Young's modulus (MPa) for randomly oriented, aligned (along fiber orientation), and perpendicular to fiber orientation. (B) Young's modulus (MPa) of randomly oriented & aligned electrospun PLA scaffolds over time in culture with or without cells (1 week and 3 weeks). (C) Stress/strain curve for each condition. (D) Dotted outlined area of stress strain curve in (C) showing "toe-region" in the aligned PLA scaffold strain. (E) Ultimate stress readings (MPa) for each condition. (F) Ultimate stress (MPa) for random & aligned electrospun PLA scaffolds over time in culture with or without cells (1 week and 3 weeks).
Figure 9B:
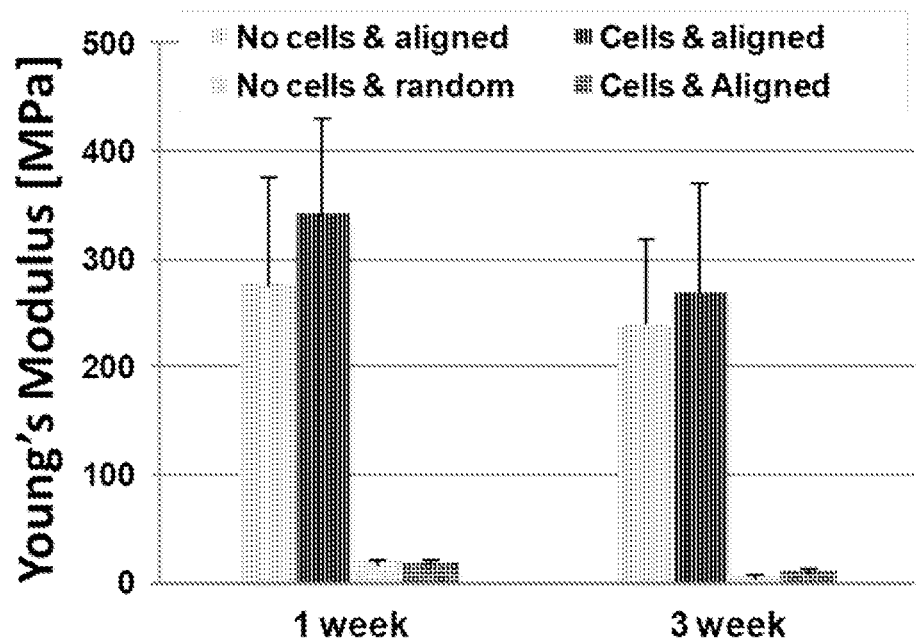
Figure 9C:
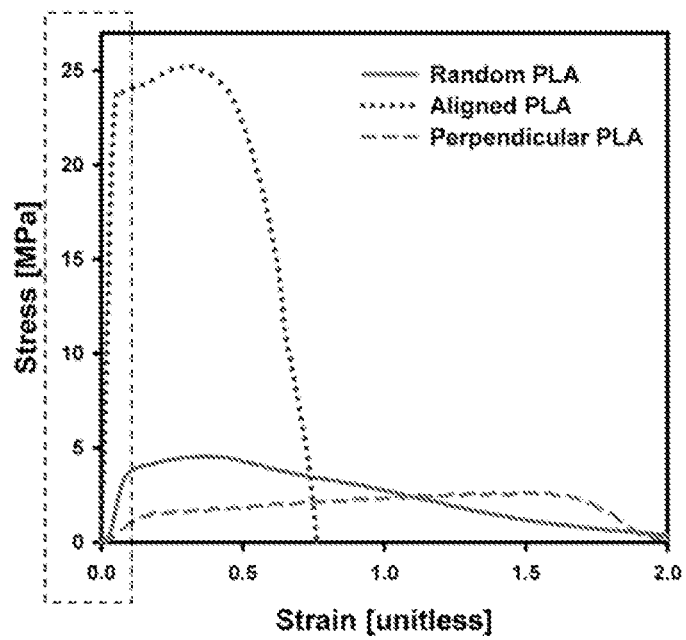
Figure 9D:
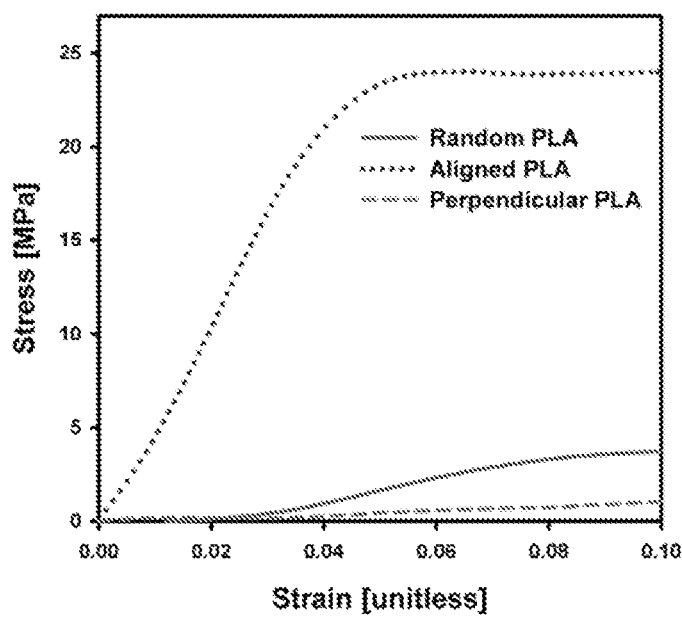
Figure 9E:
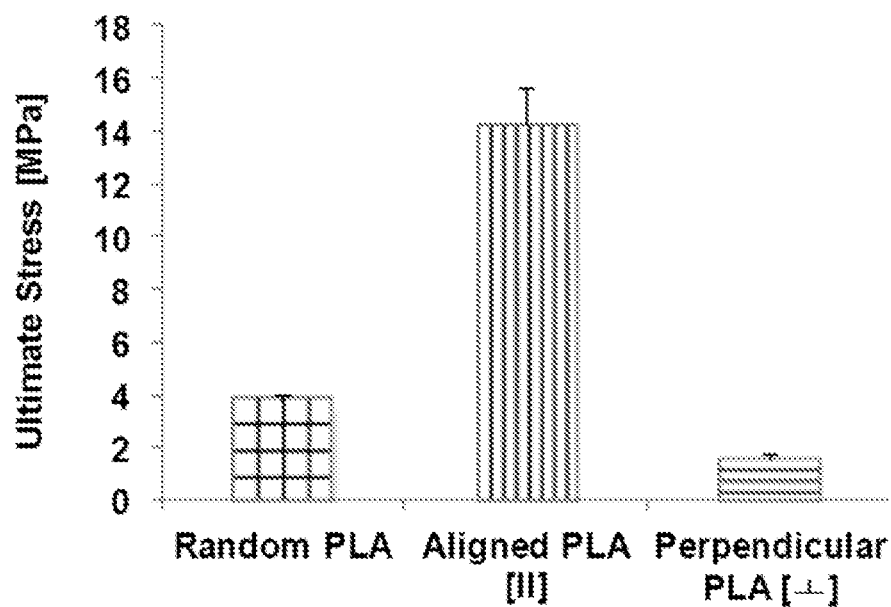
Figure 9F:
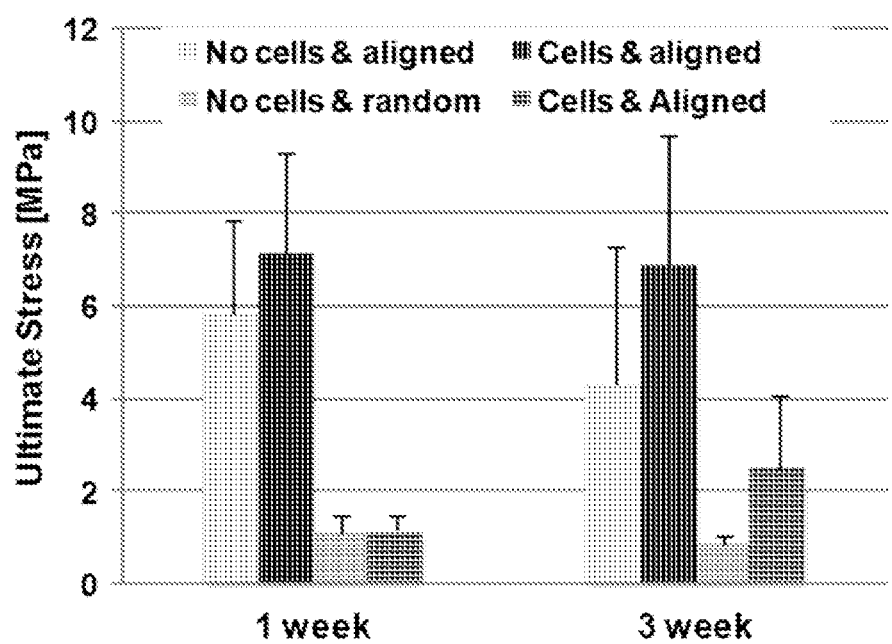

Meniscus Cell Phenotype is not Altered by Fiber Orientation or from Region of Isolation In comparison to meniscal cells in monolayer culture (baseline control gene expression levels indicated by dotted line in FIG. 8), cells derived from either vascular and avascular regions cultivated on both random and aligned ES PLA scaffolds displayed increased COL1A1, SOX9 (FIG. 8A), and COMP (FIG. 8B) gene expression levels. Decreased aggrecan mRNA was seen (2-fold) in cells on both scaffolds (FIG. 8A).

High Tensile Mechanical Properties of Aligned Electrospun PLA Scaffolds

Young's modulus and ultimate tensile strength (UTS) in the random and aligned scaffolds are presented in FIG. 9 and Table 1. Random scaffolds possess an average tensile modulus of 67.31±2.04 MPa. Aligned scaffolds, tested in the direction parallel to the aligned nanofibers generated a significantly greater (p<0.001) tensile modulus of 322.42±34.40 MPa, compared to random scaffolds. However, the tensile modulus perpendicular to the aligned direction was 7.18±1.27 MPa, significantly weaker than random scaffolds (p<0.001). Similarly, UTS of aligned scaffolds was significantly (p<0.001) higher: 14.24±1.45 MPa (parallel to direction of alignment) compared to 3.8±0.21 MPa measured in the random ES scaffolds.

Random scaffolds showed a relatively linear stress strain curve in the pre-yield region, and extended nonlinearly after yield. Aligned scaffolds tested in the direction of fiber orientation generated a sharper increase in stress with a "toe region" and increasing deformation (FIG. 9C), and yielded and failed at comparatively adjacent points earlier in the strain region. Aligned scaffolds were measured in the perpendicular direction to rotation direction, exhibiting a much lower stress-strain response.

TABLE 1

Ultimate tensile strength and Young's modulus (MPa) of freshly made and non-cultured random and aligned electrospun PLA scaffolds.

| | Random PLA | Aligned PLA | Perpendicular to aligned PLA |
|---|---|---|---|
| Ultimate Tensile Strength [MPa] | 3.80 ± 0.21 | 14.24 ± 1.45 | 1.54 ± 0.26 |
| Young's Modulus [MPa] | 67.31 ± 2.04 | 322.42 ± 34.40 | 7.18 ± 1.27 |

Mechanical properties of cell-seeded and paired acellular scaffolds were assessed via tensile testing with time in culture (Table 2). The stiffness of all scaffolds showed some decrease with time in culture. However, cell-seeded scaffolds consistently generated higher stiffness and reached a high ultimate tensile stress.

TABLE 2

Ultimate tensile strength and Young's modulus (MPa) of random & aligned electrospun PLA scaffolds over time in culture with or without cells (1 week and 3 weeks).

| Time in Culture | Electrospun nanofiber [type] | Tensile Strength [MPa] | Young's Modulus [MPa] |
|---|---|---|---|
| 1 week | Cells and Aligned | 5.87 ± 1.97 | 342.13 ± 36.45 |
| | No cells and Aligned | 7.16 ± 0.87 | 275.76 ± 43.91 |
| 3 week | Cells and Aligned | 6.88 ± 1.07 | 268.98 ± 41.42 |
| | No cells and Aligned | 4.32 ± 0.64 | 239.35 ± 33.31 |
| 1 week | Cells and Random | 1.18 ± 0.29 | 17.70 ± 5.82 |
| | No cells and Random | 1.14 ± 0.33 | 16.26 ± 6.08 |
| 3 week | Cells and Random | 2.53 ± 1.53 | 10.03 ± 4.72 |
| | No cells and Random | 0.89 ± 0.19 | 4.67 ± 3.28 |

Multi-Layer PLA Cell-Seeded Scaffold Support Meniscus-Like Neotissue Formation

Figure 10A:
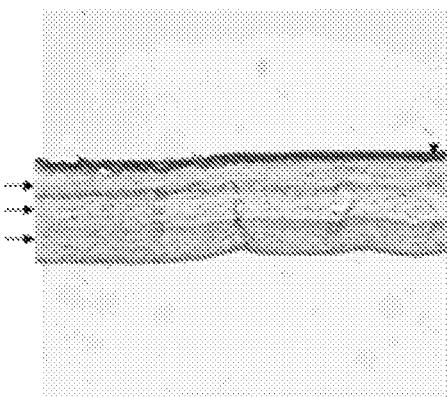
FIG. 10A-F depicts histology and immunohistochemistry of multi-layer aligned PLA cell seeded scaffolds. (A-B) Safranin O/Fast-green stain of 2 weeks cultured construct. Arrows indicate 3 aligned PLA scaffold layers and the arrow head points to the layer of alginate. (C-D) Collagen type I immunostain. (E-F) Isotype control stain. (Mag. A and C=10×; B and D=40×).
Figure 10B:
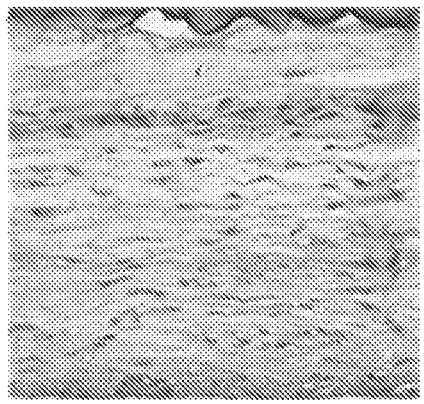
Figure 10C:
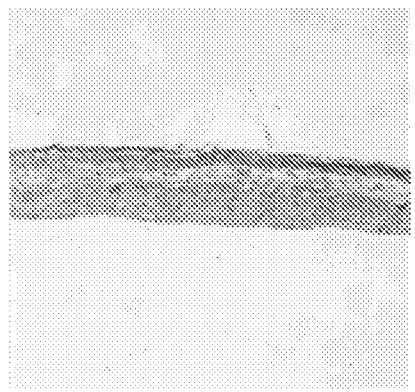
Figure 10D:
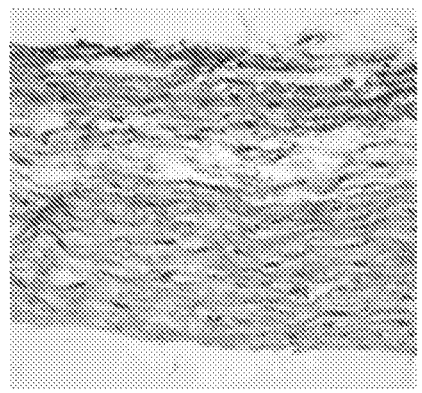
Figure 10E:
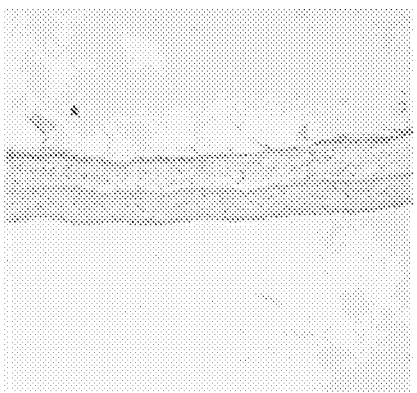
Figure 10F:
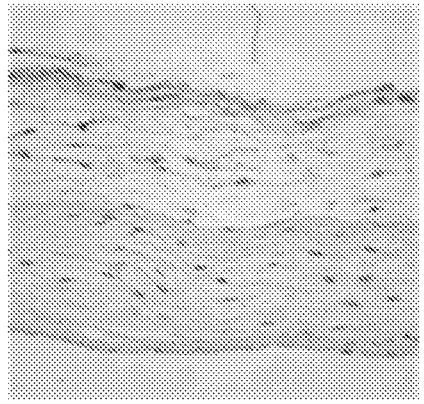

Multilayer constructs using aligned scaffolds were made since this would mimic the circumferential collagen fibrous bundles with a tensile modulus greater than 300 MPa. Human avascular meniscus cells were seeded onto three scaffolds within a biomimetic gel composed of collagen type II, chondroitin sulfate and hyaluronan (1 mg each) and held in place with a layer of 2% alginate crosslinked with calcium chloride (FIG. 6C). Two-week old constructs produced neotissue that was Safranin-O negative (FIGS. 10A and 10B), with extracellular matrix composed of collagen type I (FIGS. 10C and 10D) and with cells elongated in the same direction/orientation as the ES PLA fibers. Moreover, the neotissues fused together the three layers of PLA scaffold, and cells infiltrated and distributed inside and throughout the triple-layered construct.

Example 2

Meniscal Tissue Engineering: Cell Seeding into Electrospun Collagen

In the present study, electrospinning structures composed of collagen type I and production of natural hydrogels seeded with human meniscus cells from vascular and avascular regions of the meniscus were combined to produce scaffolds that mimic the native tissue.

Materials and Methods

Bovine collagen type I (16 wt % solution in PBS and ethanol) was electrospun (ES) by delivery of a syringe pump at a feeding rate of 0.1 mL/h and a voltage of 15 to 20 kV. Random ES scaffolds were generated on a flat plate collector and aligned ES scaffolds were collected on a rotating drum cylinder. ES scaffolds were crosslinked in glutaraldehyde solution (0.25%) in PBS. Human menisci from four donors were obtained from tissue banks (approved by Scripps Institutional Review Board) and cells were isolated via enzymatic digestion in collagenase and culture expanded for one passage in DMEM with 10% CS+1% PSG. The cultured cells were seeded on the scaffolds at a density of $50 \times 10^3$ per scaffold (2×3 cm) in 6-well plates. The seeded scaffolds (random or aligned collagen) were cultured in DMEM with 10% CS medium for 4-5 days before changing to a serum free medium (ITS+) supplemented with TGF beta 1 (10 ng/ml) to promote neo-meniscus tissue formation. The cell-seeded scaffolds were cultured for 2 weeks before analysis. To produce multi-layered cell-seeded scaffolds, human avascular meniscus cells were encapsulated in a hydrogel consisting of collagen type II, chondroitin sulfate and hyaluronan (1 mg each) at $50 \times 10^3$ cells per ml. Cells were seeded onto one aligned collagen scaffold (50 µl), which were cut into 6 mm diameter disks. Three layers of cell-seeded scaffolds were stabilized with 2% alginate and cultured in serum-free medium supplemented with TGF beta 1 (10 ng/ml). To determine cell viability selected mats were incubated in a live/dead reagent. The two-week old multi-layer constructs were fixed (Z-fix) and stained (H&E and Safranin O) or processed for immunostaining of type I collagen. The morphology and average diameter of ES collagen scaffolds and cell interactions was observed by Scanning electron microscopy. Gene expression levels of CHAD, COL1A1, Aggrecan, THY1, relative to GAPDH, were assessed in meniscus cells cultured on random and aligned collagen scaffolds after 2 weeks. Each gene per sample was normalized by GAPDH mRNA levels and gene expression levels in the neotissue samples were compared to monolayer cultured normalized mRNA levels. Mechanical stiffness and strength in uniaxial tension was measured on scaffolds cut into dog-bone shaped specimens with a gauge length of 8 mm and width of 2 mm.

Results

Figure 11A:
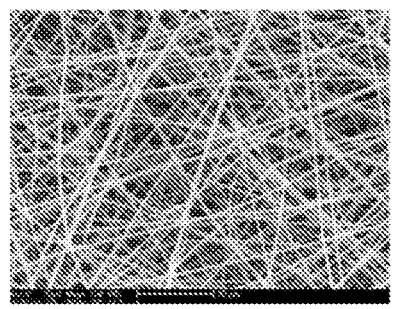
FIG. 11A-F depicts scanning electron micrographs (SEM) of electrospun (ES) collagen scaffolds and cellular response. (A) SEM of randomly oriented and (B) aligned ES collagen fibers. (C) SEM of human meniscus cells cultivated on randomly oriented and (D) aligned ES collagen fibers (Scale bar=5 μm). Mechanical testing of random and aligned ES collagen scaffolds according to crosslinking (E) Young's modulus (MPa) for random, aligned (along fiber orientation), and perpendicular to fiber orientation. (F) Stress/strain curve for each condition. White bars represent non-crosslinked ES collagen scaffolds and the black bars are ES collagen scaffolds crosslinked in 0.25% glutaraldehyde in 1×PBS for 1 hour.
Figure 11B:
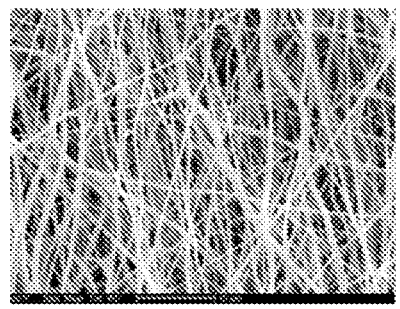

ES collagen scaffold characterization: The morphological features of aligned and random ES collagen type I fibers are shown in FIGS. 11A and 11B. While randomly ES collagen fibers appeared truly random (FIG. 11A), scaffolds produced using the rotating drum speed and delivery parameters used successfully produced scaffold structures with a high order of alignment (FIG. 11B). The mean aligned fiber diameter was 456±97 nm (range: 340-860 nm) and 467±76 nm for the random fibers (range: 250-720 nm).

Figure 11C:
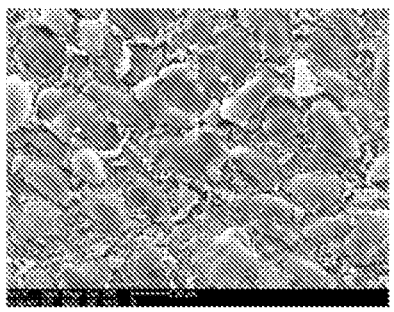
Figure 11D:
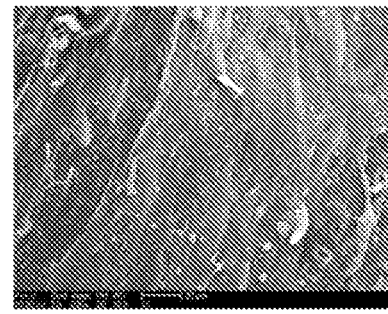

Cell morphology and collagen fiber arrangement: Cells seeded upon randomly ES collagen scaffolds were flattened and spread-out with multidirectional extensions (FIG. 11C), while cells on aligned collagen scaffolds were elongated in line with the direction of the fibers (FIG. 11D). This morphology and alignment reaction was also captured in the confocal images, where the cells were more than 80% viable.

Figure 11E:
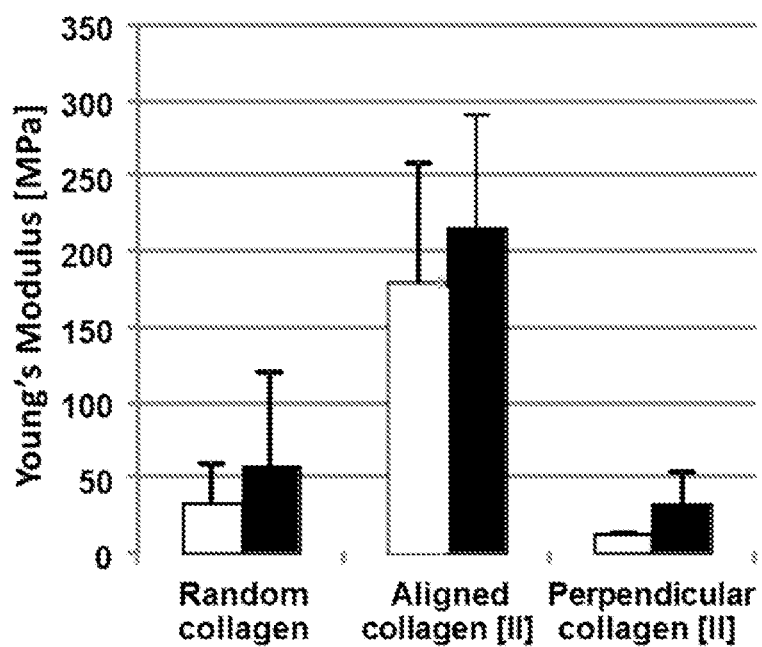
Figure 11F:
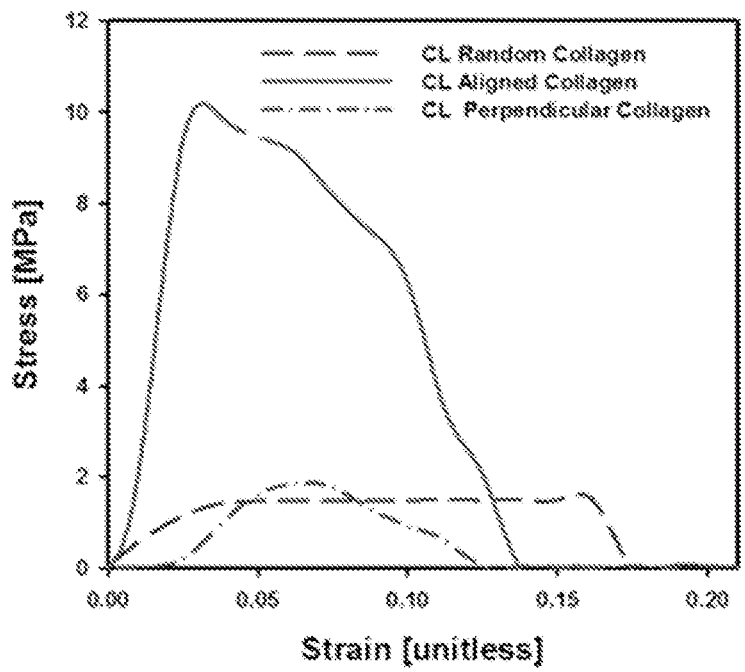

Mechanical properties: Non-GA crosslinked randomly ES oriented scaffolds possessed an average tensile modulus of 32.48±11.84. MPa, while crosslinked random scaffolds possessed an average tensile modulus of 57.56±28.11 MPa. Non-crosslinked aligned scaffolds, tested in the direction parallel to the aligned nanofibers, had a significantly greater ($p<0.001$) tensile modulus of 178.72±78.53 MPa, and further increased to 214.76±75.41 MPa when crosslinked in comparison to random scaffolds regardless of crosslinking (FIG. 11E-F).

Figure 12A:
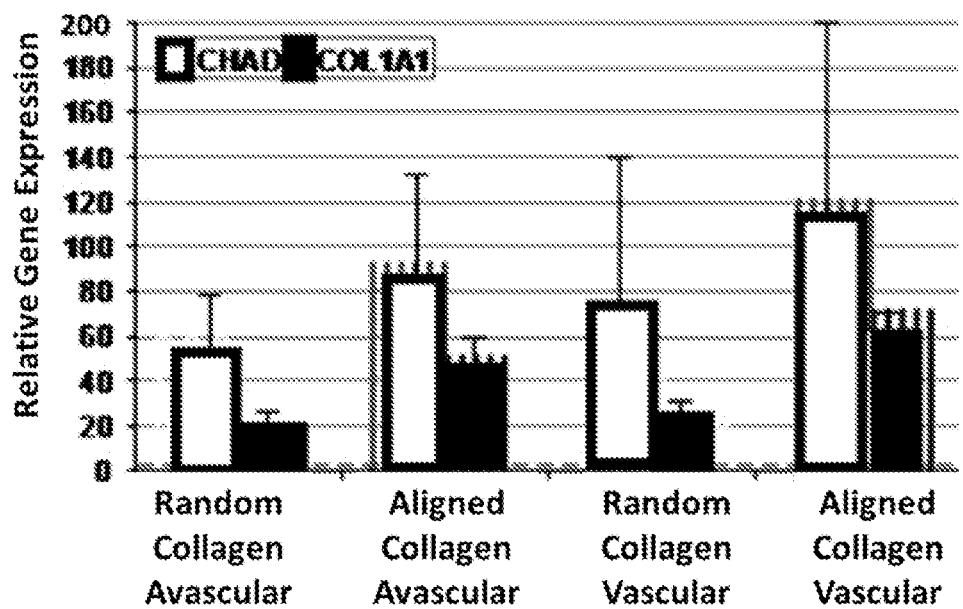
FIG. 12A-C depicts relative gene expression profiles of human meniscus cells (n=4) from the vascular and avascular regions seeded on randomly oriented and aligned ES collagen scaffolds with tri-matrix gel and cultured for 14 days in ITS+ with TGF beta 1 (10 ng/ml).
Figure 12B:
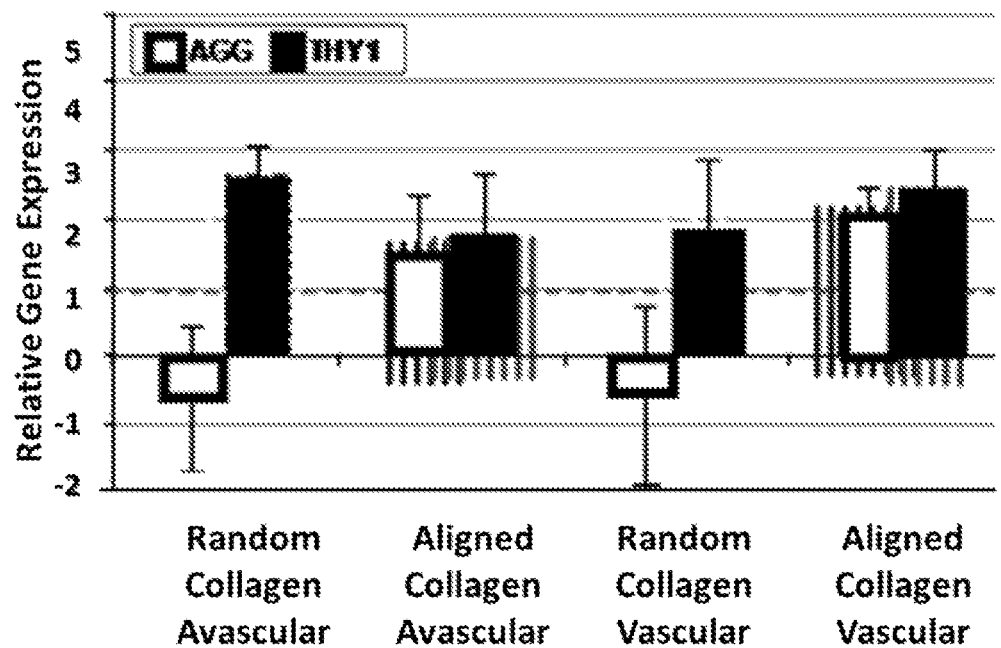
Figure 12C:
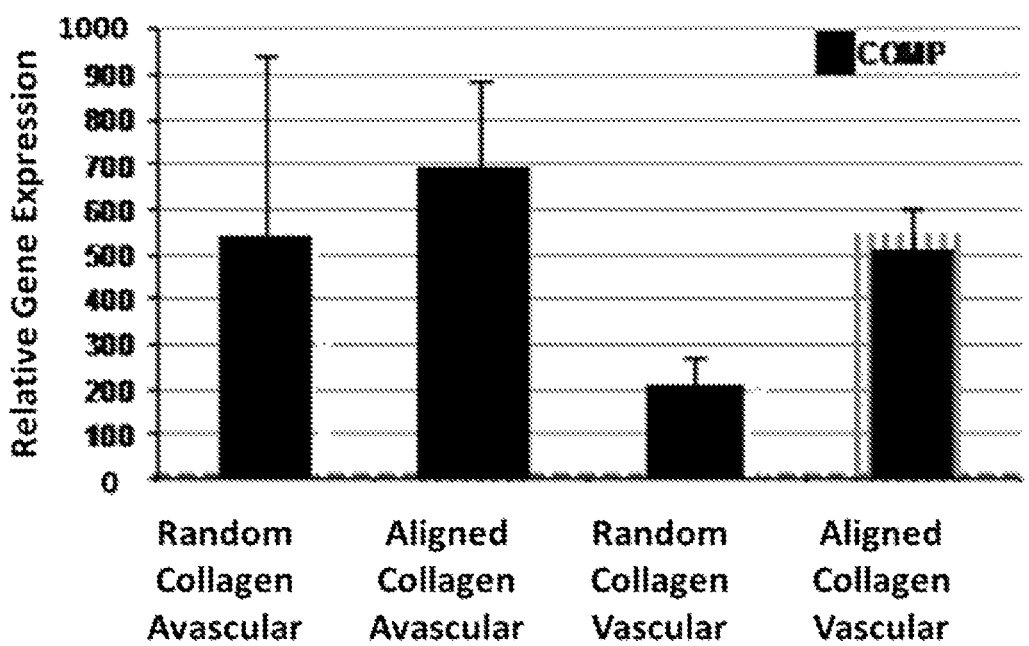
Figure 15:
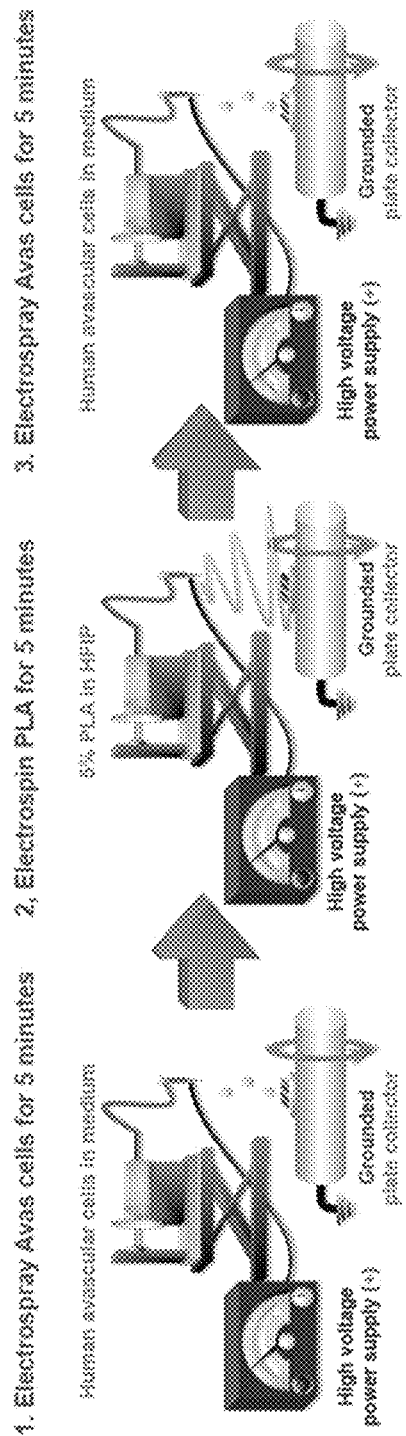
FIG. 15 depicts alternating electrospinning a polymer solution and electrospraying cells to generate layers of electrospun mats with live cells between the electrospun layers.
Figure 16A:
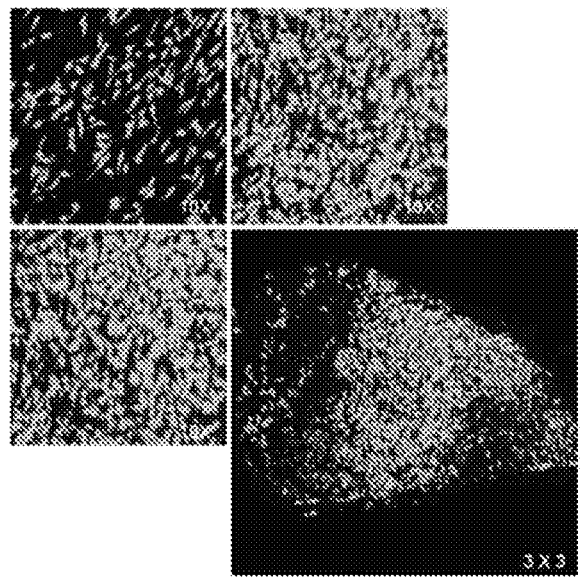
FIG. 16A-B depicts high cell viability one month after sequential electrospraying and electrospinning: (A) Cells electrosprayed onto a grounded collector; (B) cells electrosprayed onto a negatively charged collector.
Figure 16B:
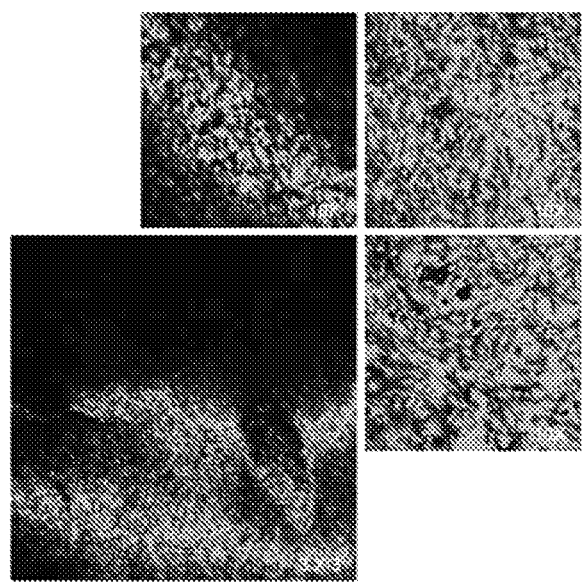
Figure 17A:
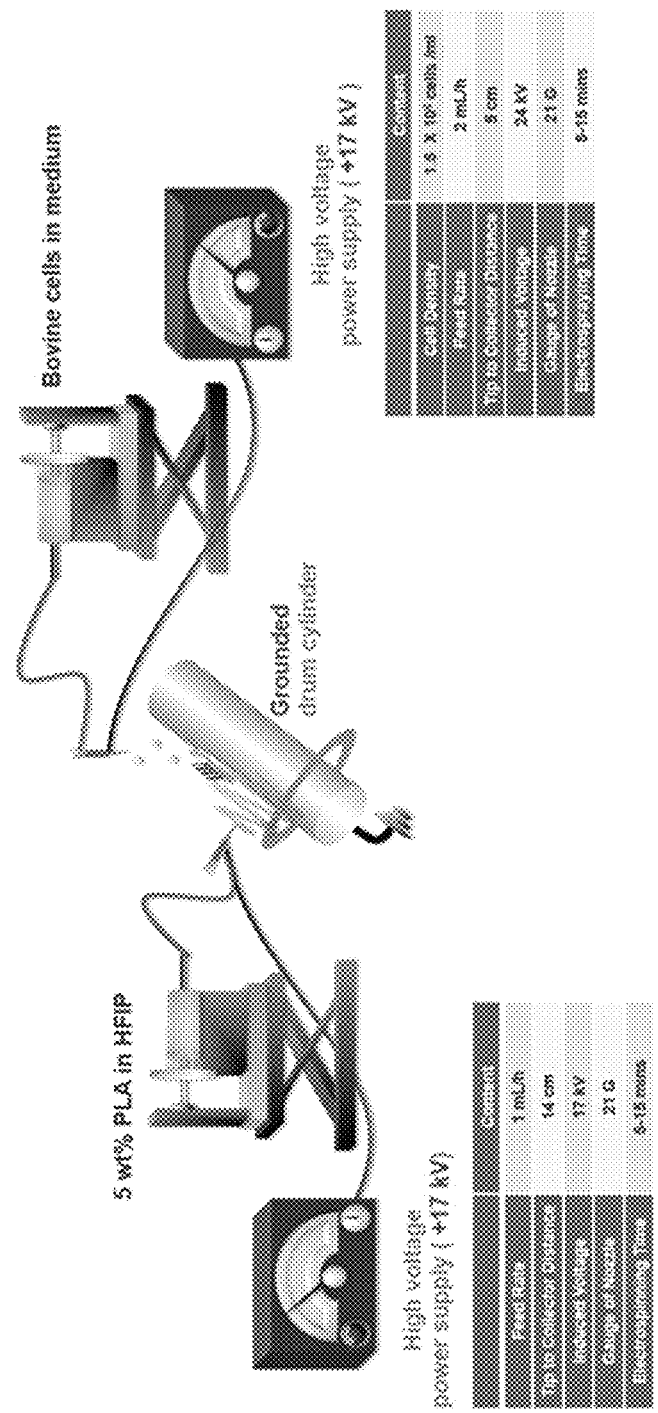
FIG. 17A exemplifies simultaneous electrospinning and electrospraying to generate layers of electrospun mats with embedded live cells.
Figure 19:
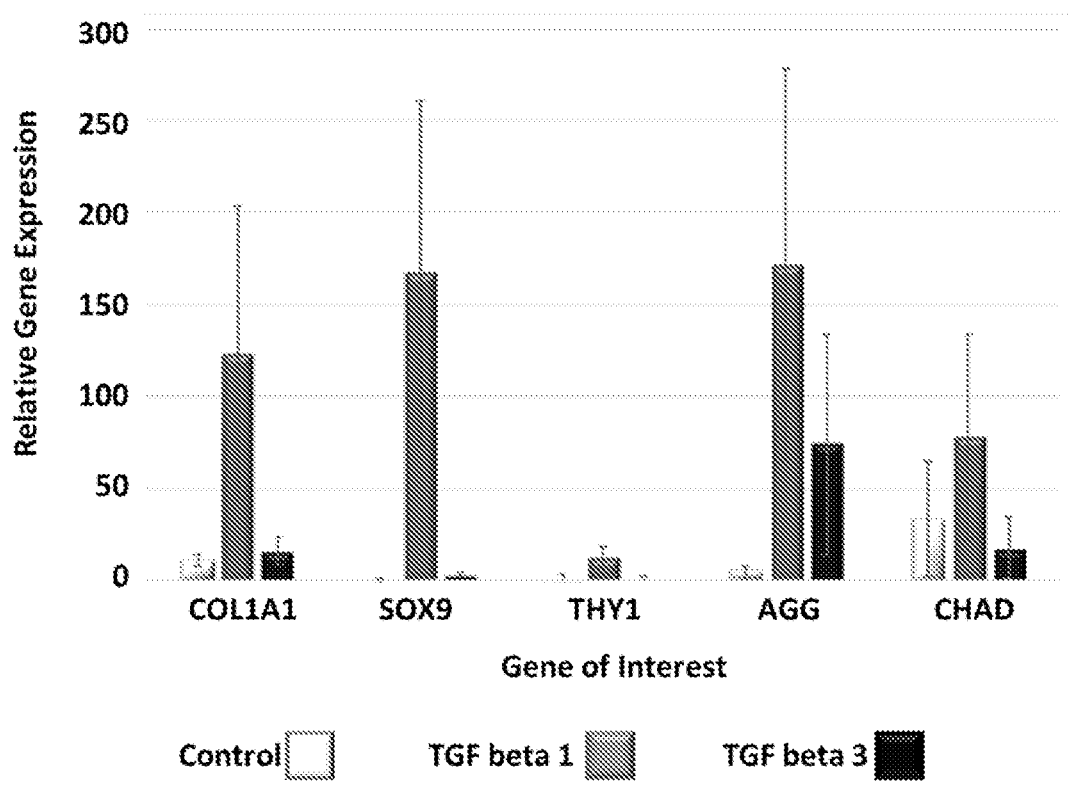
FIG. 19 depicts meniscus-like gene expression from multiple collagen layers with mesenchymal stem cells, stimulated with TGF beta 1 or 3.

Neo-Meniscus tissue formation: In comparison to monolayer culture, meniscus cells cultivated on both random and aligned ES collagen scaffolds showed increased COL1A1, CHAD and COMP mRNA levels (FIG. 12). For both meniscus cell types, aligned ES collagen scaffolds increased COL1A1 mRNA levels compared to cells cultured on random ES scaffolds. Higher AGG gene expression was observed in the aligned collagen condition (FIG. 12B), yet no significant change in AGG levels was seen with cells cultured on random collagen scaffolds. Vascular meniscus cells cultured on random mats showed a relative decrease in COMP mRNA levels compared to vascular cells cultured on aligned mats (FIG. 12C). All neotissues produced displayed a lack of Safranin-O stain and extensive deposition of collagen type I.

Discussion

This study demonstrates the capacity to produce random and aligned ES collagen scaffolds. Both scaffolds possess similar and uniform fiber diameters, permitted cell attachment, altered cell morphology and alignment, both showed minimal cytotoxicity and appear to support neo-meniscus tissue formation. While the aligned ES collagen scaffolds promoted cell alignment that emulates meniscus tissue, randomly ES collagen scaffolds appeared to support the differentiation of monolayer cultured meniscus cells to a meniscus phenotype with high expression of CHAD, COMP and COL1A1. A range of anisotropic behaviors was generated, with an 8-fold difference in tensile moduli parallel and perpendicular to the direction of the aligned collagen scaffolds, while the tensile modulus of aligned scaffolds was approximately 5-fold higher than randomly oriented scaffolds. In humans, significant regional variations are observed in the stiffness and strength of the normal meniscus in circumferential tension with a Young's modulus ranging from 93-298 MPa. The mechanical properties of collagen scaffolds produced in this study resulted in tensile properties similar to those of human meniscus. Overall, production of ES collagen scaffolds might be a promising means to engineer a meniscus graft tissue that appears to possess the biological and mechanical qualities to survive in a joint-loading environment.

Untreated damaged or degenerated meniscus can lead to the development of osteoarthrities. Scaffold systems that can emulate meniscus tissue characteristics and mechanical properties and support meniscus tissue formation represent a promising means to treat meniscus lesions and to prevent or delay degenerative changes that lead to osteoarthritis formation.

Example 3

Cell-Seeded Polymer Scaffold Production: Simultaneous Electrospinning and Electrospraying Embed Cells in a Polymer Scaffold A polymer solution is electrospun (ES) by delivery of a syringe pump. Random polymer fibers are generated on a flat plate collector and aligned ES polymer fibers are collected on a rotating drum cylinder. Simultaneously, cells are electrosprayed on to the collector, to produce a cell-seeded polymer scaffold composition with embedded cells. ES polymer fibers are photocrosslinked as they are collected. Alternative to photocrosslinking, a non-toxic chemical crosslinking solution is added after electrospinning and electrospraying to cross-link the polymer fibers.

Example 4

Cell-Seeded Collagen Scaffold Production: Simultaneous Electrospinning and Electrospraying Embed Cells in a Collagen Scaffold A collagen solution is electrospun by delivery of a syringe pump. The collagen is dissolved in water. Alternatively, collagen is dissolved in hexafluoro-2-propanol (HFIP) at a working concentration of 16% collagen by weight in HFIP. Random collagen fibers are generated on a flat plate collector and aligned ES polymer fibers are collected on a rotating drum cylinder. Simultaneously, cells are electrosprayed on to the collector, to produce a cell-seeded polymer scaffold composition with embedded cells. ES collagen fibers are photocrosslinked as they are collected. Alternative to photocrosslinking, a non-toxic chemical crosslinking solution is added after electrospinning and electrospraying to cross-link the polymer fibers. An oxidant is released from methacrylated collagen fibers by adding riboflavin to the polymer scaffold composition. Alternatively, a photoinitiator is added to the polymer scaffold composition and exposing the polymer scaffold composition to an ultraviolet light releases an oxidant from the methacrylated collagen fibers, resulting in a chemical bond between the methacrylated collagen fibers.

Example 5

Production of a Biodegradable Meniscal Collagen Implant (Collagen, Methacrylated, v-Shaped, Meniscal Cells)

Methacrylated collagen is dissolved in water to produce a methacrylated collagen solution. Alternatively collagen is dissolved in hexafluoro-2-propanol (HFIP) at a working concentration of 16% collagen by weight in HFIP. The methacrylated collagen solution is electrospun by delivery of a syringe pump on to a rotating v-shaped drum cylinder to produce a collagen scaffold that is shaped like a meniscus composed of aligned ES methacrylated collagen fibers. Human menisci from four donors are obtained from tissue banks and meniscal cells are isolated via enzymatic digestion in collagenase and culture expanded for one passage in DMEM with 10% CS+1% PSG. The meniscal cells are electrosprayed on to the collector simultaneously with electrospinning the methacrylated collagen solution on the collector, to produce a meniscal cell-embedded methacrylated collagen scaffold composition. A solution comprising a photoinitiator is also added to the collagen fibers as they are produced and the cell-seeded collagen scaffold composition is exposed to intermittent UV light as it is being formed on the collector. Exposing the meniscal cell-embedded methacrylated collagen scaffold composition to an ultraviolet light releases oxidants from the methacrylated collagen fibers, resulting in chemical bonds between the methacrylated collagen fibers, thereby making the resulting meniscal cell-embedded methacrylated collagen scaffold composition insoluble in a biological media, but non-toxic and biodegradable in vivo. The meniscal cell-embedded methacrylated collagen scaffold composition results in a meniscal implant that is immediately implanted in a subject. Alternatively, the meniscal implant is cultured in a cell culture media or further modified before implanting in a subject.

Example 6

Electrospun Collagen Fibrous Scaffolds, Mechanical Properties and Gene Expression 16% w/v Bovine Collagen type I (Semed S, acid-soluble, DSM, NL) was dissolved in 20× Phosphate buffered Saline (PBS) and ethanol at a ratio of 1:1 v/v. The collagen solution was placed in a syringe, which was controlled by a syringe pump (KDS200, KD Scientific Inc., USA) at a feeding rate of 0.1-0.2 mL/h. A Teflon tube was used to connect the syringe to a 21-G needle, with an inner diameter of 0.5 mm. Collagen fibers were electrospun on to collectors covered by aluminum foil. For fabricating random fibers, a flat plate was used as a collector with a tip-to-collector distance of 16 cm. For fabricating aligned fibers, a drum rotating nominally at 2400 rpm was placed at 12 cm (from the tangent surface of the drum) from the needle tip. The applied voltage was varied from 15 to 20 kV by a voltage regulated DC power supply (NNC-30 kV-2 mA portable type, NanoNC, South Korea) to generate the polymer jet. Electrospun collagen scaffolds were crosslinked by soaking in 0.25% glutaraldehyde (Sigma-Aldrich) in 1×PBS for 1 hour. After fixation scaffolds were washed three times for 10 min each with ethanol.

Figure 20A:
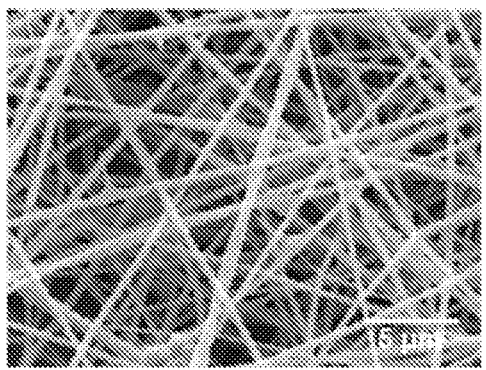
Figure 20B:
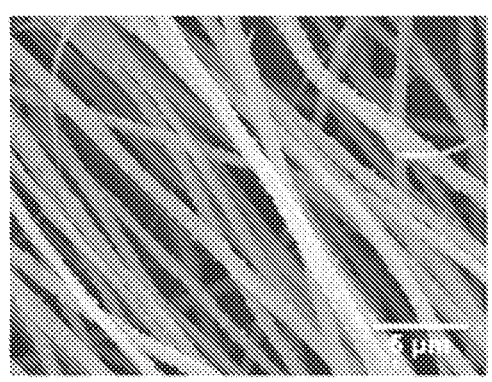

The morphological structure of aligned and random ES collagen fibers is shown in FIGS. 20A and 20B. A rotating drum speed of 2400 rpm was used to produce scaffold structures with a high degree of alignment. The average diameter of aligned fibers was 496±97 nm and that for random collagen fibers was 467±76 nm. Crosslinked random scaffolds were 0.25±0.04 mm while crosslinked aligned scaffolds were 0.25±0.03 mm in thickness. Confocal images (FIGS. 1C and D) provided evidence of higher cell viability in aligned scaffolds. Meniscus avascular and vascular cells seeded upon randomly aligned electrospun collagen scaffolds were flattened and spread-out with multi-directional extensions (FIG. 20C); while cells on aligned collagen scaffolds were elongated in line with the direction of the fibers (FIG. 20D).

Figure 21B:
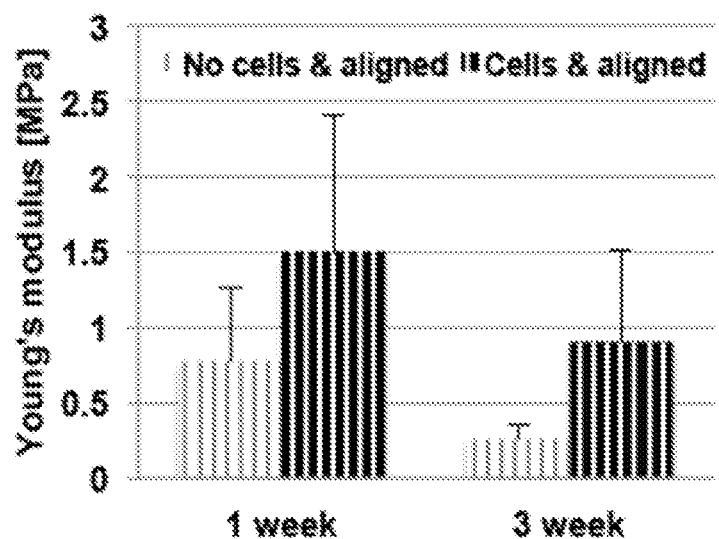
Figure 21C:
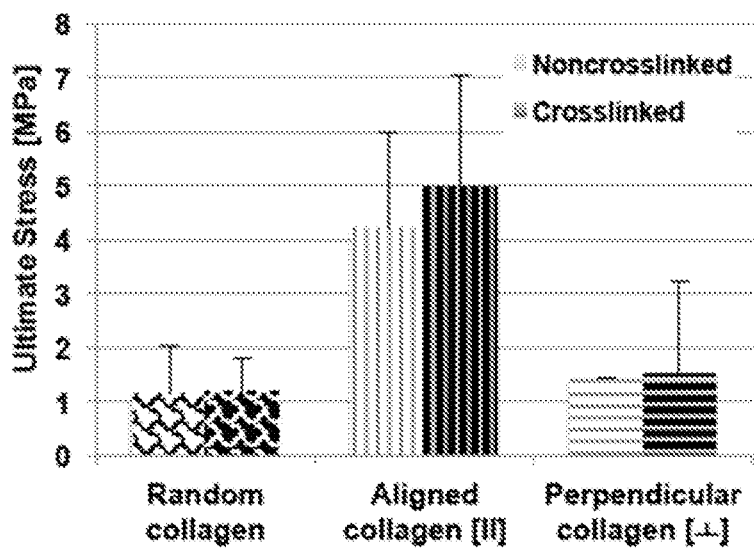
Figure 21D:
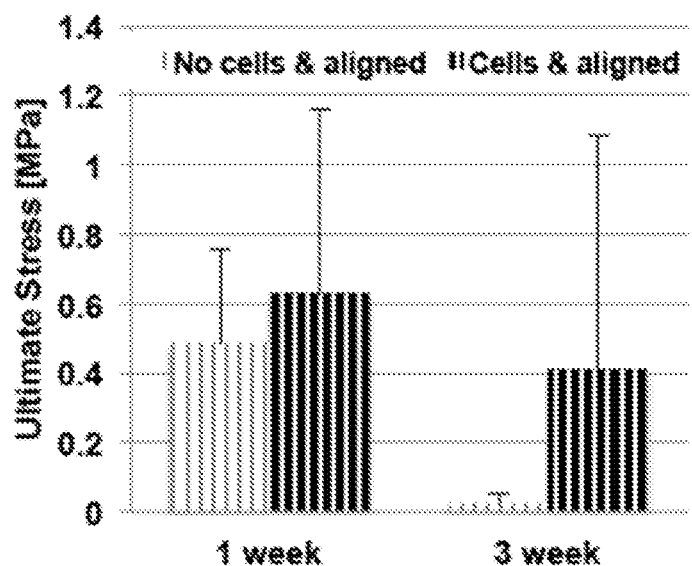

Crosslinking with glutaraldehyde increased the average tensile modulus of dry random scaffolds to 57.56±28.11 MPa (FIG. 21A). Crosslinking also increased the average tensile modulus of dry aligned collagen fibers when tested in tension parallel to or perpendicular to the direction of aligned fibers (21A). Aligned scaffolds, when tested in the direction parallel to the aligned nanofibers generated a significantly greater tensile modulus compared to random scaffolds regardless of crosslinking (p<0.001). On the other hand, the tensile modulus perpendicular to the direction of the aligned fibers was 32.18±21.68 MPa after crosslinking, significantly weaker than random scaffolds (p<0.001). Similar to the tensile modulus, the UTS of crosslinked aligned scaffolds was significantly (p<0.001) higher: 4.97±2.01 MPa (parallel to direction of alignment) compared to 1.19±0.63 MPa measured in the crosslinked random scaffolds (FIG. 21C). The stiffness of both cellular and acellular scaffolds decreased with time in culture (FIG. 21B). However, cell-seeded scaffolds were consistently stiffer and reached a higher ultimate tensile stress than acellular scaffolds (FIG. 21D).

Figure 22A:
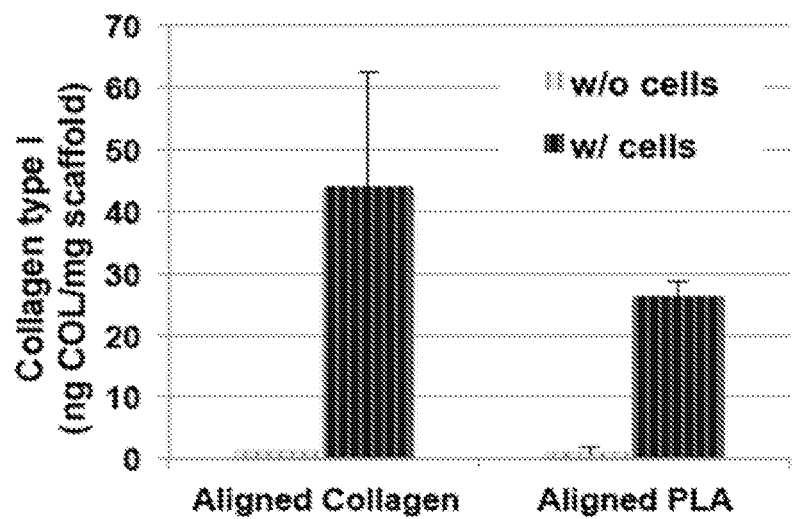
FIG. 22A-F depicts quantity of collagen type I in newly synthesized aligned ES pure collagen and mixed collagen and polylactic acid layers (A) and relative gene expression of cells derived from either vascular or avascular regions cultivated on either random or aligned collagen scaffolds (B—F).
Figure 22B:
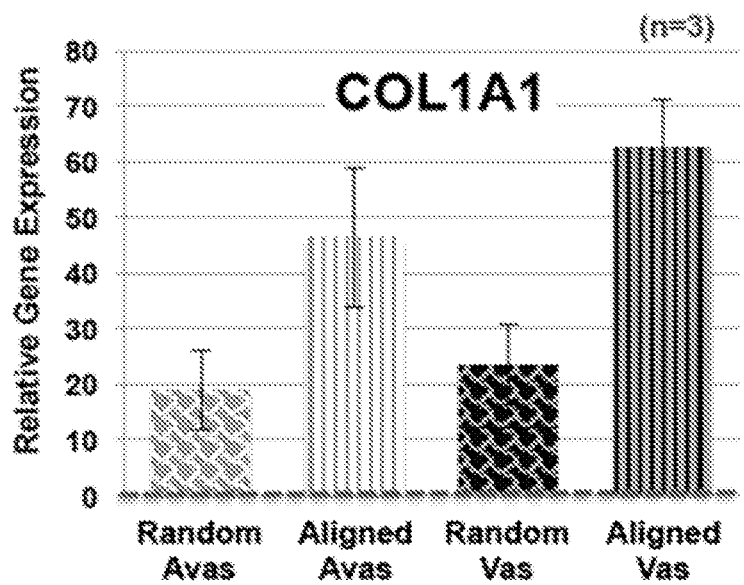
Figure 22C:
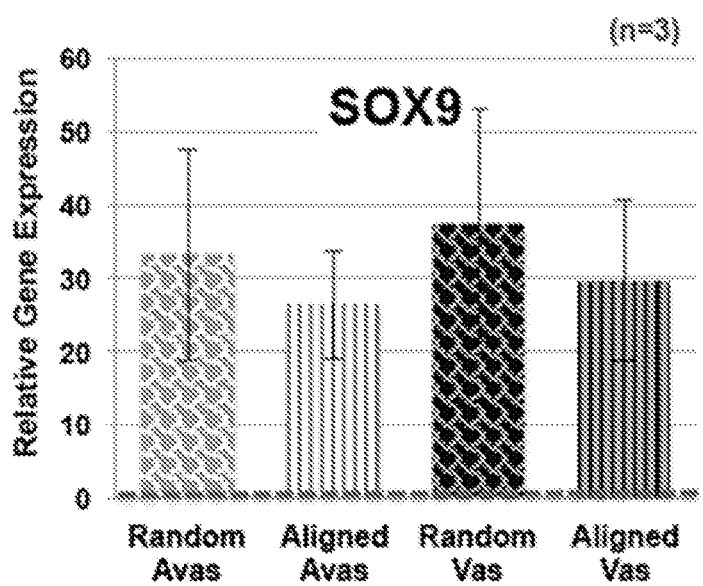
Figure 22D:
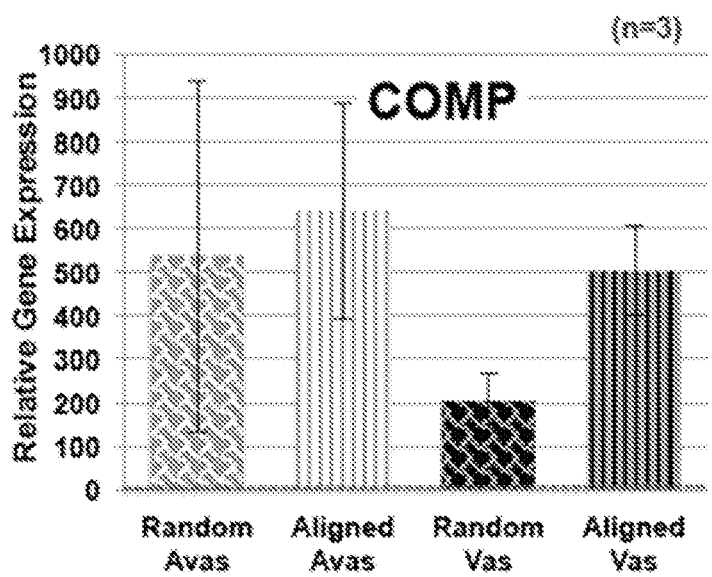

To identify the reason for the increased mechanical property of cell-seeded scaffolds we used ELISA to measure newly synthesized collagen type I (FIG. 22A) and qPCR to measure COL1A1 gene expression (FIG. 22B). Collagen type I protein in cell-seeded scaffolds was significantly higher than the negative control (acellular scaffold); demonstrating that the ELISA was detecting newly synthesized protein and not the collagen used to fabricate the scaffold.

Figure 22E:
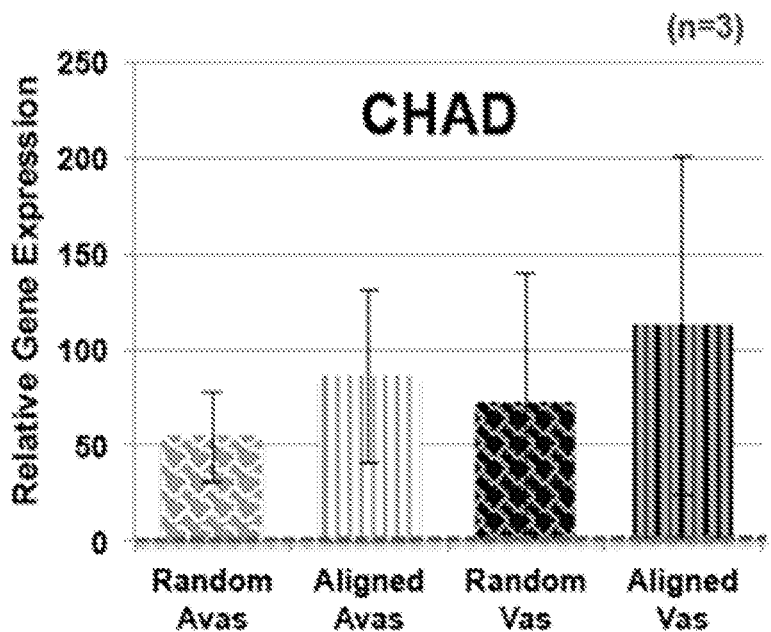
Figure 22F:
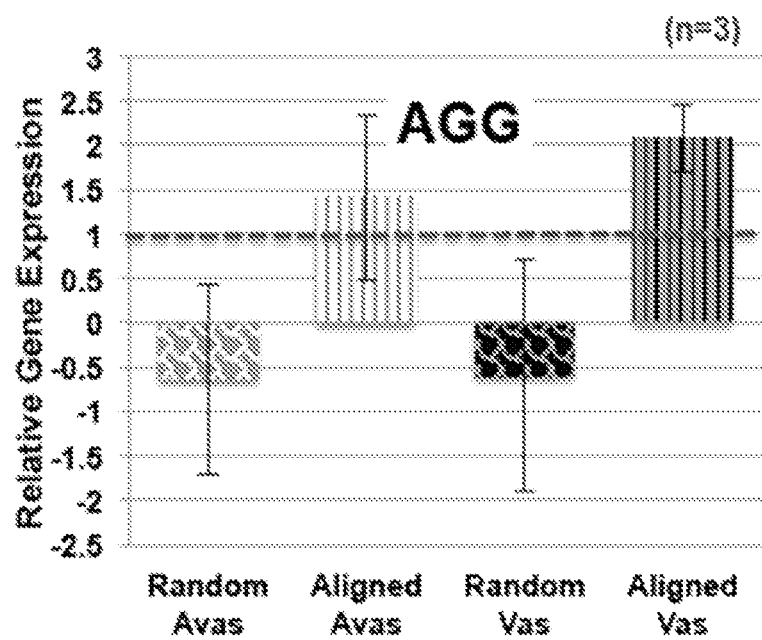

A meniscus-like phenotype supported by scaffold and specific gene responses differed between cell source and scaffold organization. In comparison to meniscal cells in monolayer culture (baseline control gene expression levels indicated by dotted line in (FIGS. 22B-F), cells derived from either vascular or avascular regions cultivated on either random or aligned collagen scaffolds expressed significantly (P<0.05) higher levels of COL1A1, SOX9, COMP, CHAD, and AGG genes. Aggrecan mRNA levels were either decreased (random scaffolds) or unchanged (aligned scaffolds, FIG. 22F). In overview, COL1A1 and CHAD mRNA expression levels were comparable for both meniscus cell sources on both scaffolds (FIGS. 22B and 22E).

Example 7

Figure 23A:
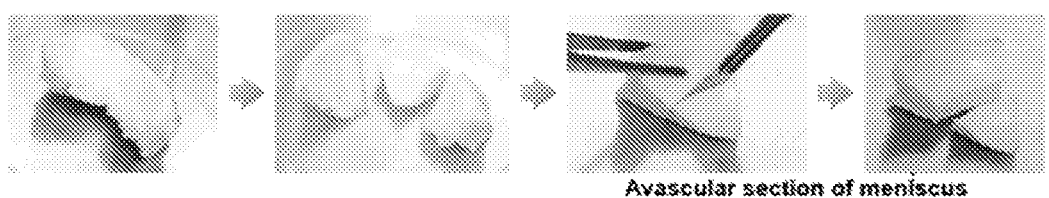
FIG. 23A-F depicts fresh menisci harvested from bovine knees and sectioned with surgical cuts within the avascular meniscal tissue to simulate a meniscal tear (A); a schematic of cell-seeded collagen scaffolds implanted in the surgically created longitudinal tears of the bovine menisci (B); histological analysis within the tear between the implanted scaffolds and the native tissue for a control unrepaired tear (C), tear repaired with scaffold without cells (D), a vertical tear repaired with scaffold and cells (E), and a horizontal tear repaired with scaffold and cells (F). Arrows point to unhealed tears (C & D) and healed tears (E & F).
Figure 23B:
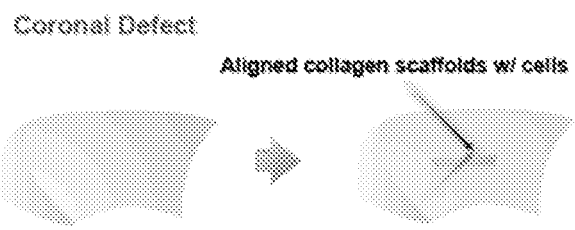
Figure 23C:
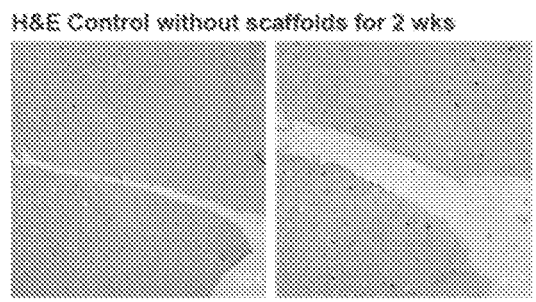
Figure 23D:
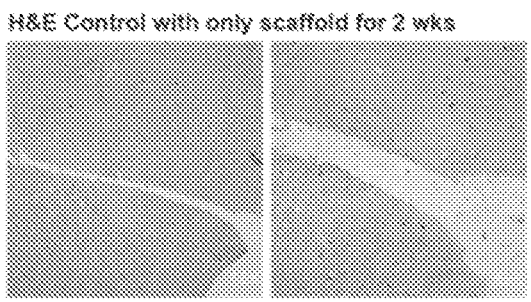
Figure 23E:
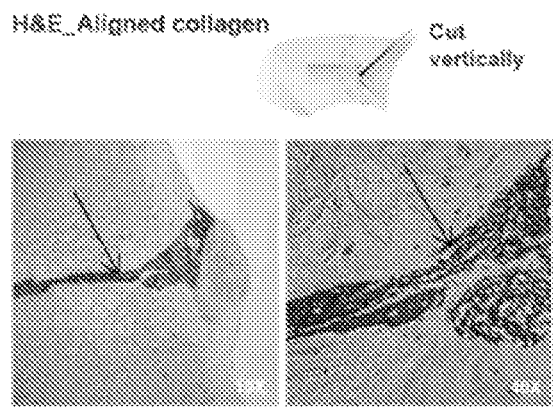
Figure 23F:
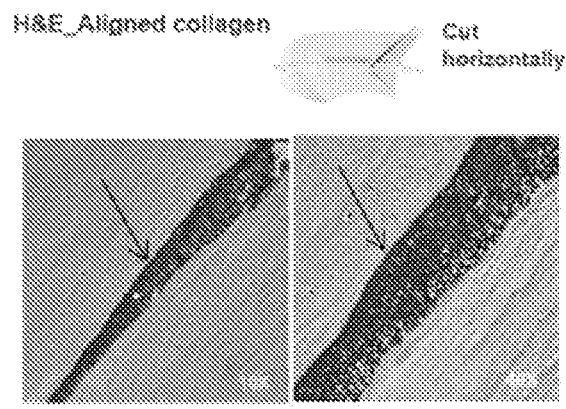
Figure 24:
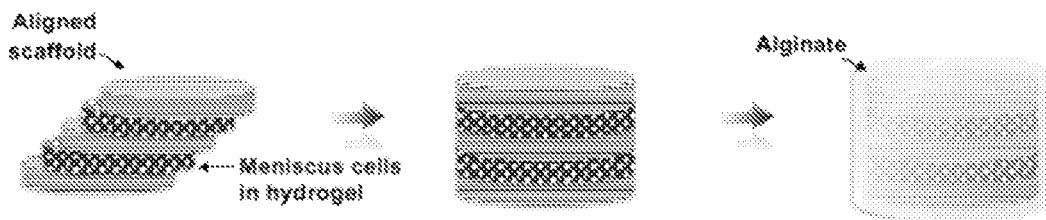
FIG. 24 depicts a schematic exemplary process of producing multiple collagen layers with human meniscus cells in a hydrogel, the hydrogel containing collagen type II, chondroitin sulfate and hyaluronan and cells seeded at a density of one million cells per ml in 50 microliters for each layer. The resulting multi-layer constructs would mimic the circumferential collagen fibrous bundles in tissues.

Integration and Neo-Tissue Formation of ES Cell Seeded Scaffolds in an Ex Vivo Meniscus Defect Model Fresh menisci were harvested from bovine knees and sectioned. Surgical cuts were created within the avascular meniscal tissue to simulate a meniscal tear (FIG. 23A). Human meniscus cells were seeded on collagen aligned scaffolds and precultured for 4 weeks. Cell-seeded scaffolds were then implanted in surgically created longitudinal tears in bovine meniscus tissue explants (FIG. 23B). After culturing the repaired meniscal tissue for 3 weeks, histological analysis revealed the generation of new tissue within the tear between the implanted scaffolds and the native tissue; and with integration of neotissue into host tissue (FIG. 23C): unrepaired tear; (FIG. 23D): tear repaired with scaffold without cells; FIGS. 23E and 23F: tears repaired with scaffolds with cells. Arrows point to unhealed tears (FIGS. 23C & D) and healed tears (FIGS. 23E & F).

Example 8

Production of Multi-Layer Constructs with Pure Collagen Fibers

Figure 25A:
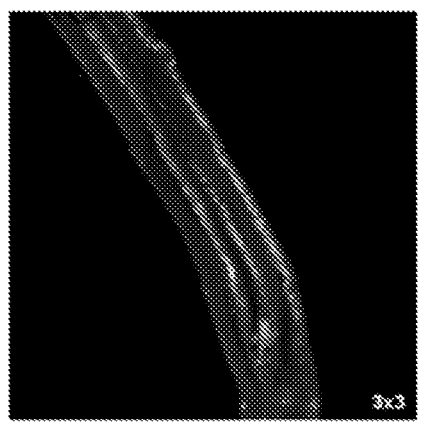
FIG. 25A-B depicts live (light or white regions) staining of meniscus cells seeded in multi-layer constructs after 14 days at low (A) and higher (B) magnification, mimicking circumferential collagen fibrous bundles in tissue.
Figure 25B:
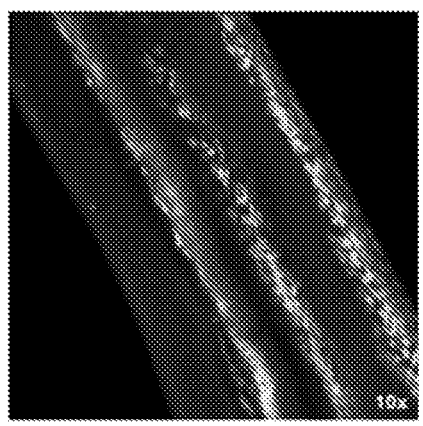
Figure 26A:
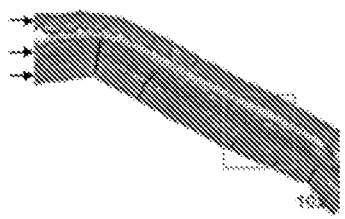
FIG. 26A-D depicts formation of meniscus-like fibrous tissue with safranin O fast-green stain of two week cultured multi-layer constructs at (A) 10× and (B) 40× magnification, as well as H & E stain of 2 week cultured constructs at (C) 10× and (D) 40× magnification
Figure 26B:
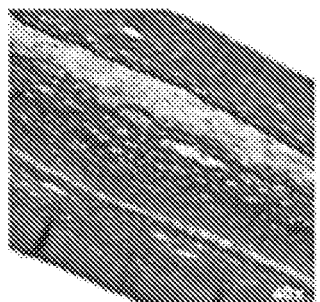
Figure 26C:
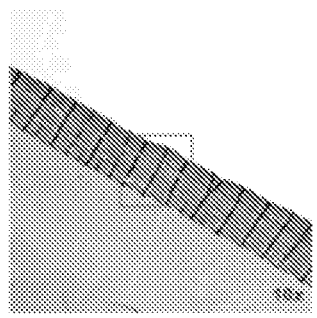
Figure 26D:
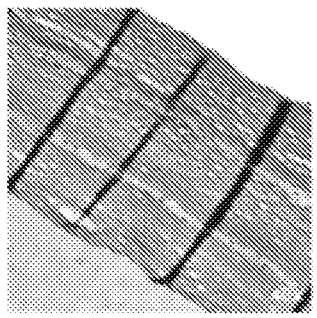

Electrospun single layer collagen scaffolds were produced as is detailed in Example 6. The scaffolds were then cut into discs. Multi-layer constructs were produced by layering the discs with alternating layers of human meniscus cells in hydrogel containing collagen type II, chondroitin sulfate and hyaluronan. The resulting multi-layer constructs mimicked the circumferential collagen fibrous bundles in tissues. Cells were seeded at a density of one million cells per ml in 50 microliters for each layer. Cells survived 14 days after seeding as shown in FIGS. 25A and B and Safranin O fast-green stain of two-week cultured constructs showed the presence of cartilage (FIG. 26A-B). Macro top and side views of disc halves are shown in FIGS. 28A & B.

Example 9

Co-Axial Electrospinning Method

Voltage was applied to collagen and PLA solutions in separate syringes onto a drum to create electrospun fibers with a PLA fiber core and collagen fiber shell. The syringes were separate and connected to a hollow needle that has two concentric channels (like a hollow cylinder within a hollow cylinder). The PLA solution was ejected through the inner channel of the needle and the collagen solution was ejected through the outer channel of the needle. At the tip of the needle the collagen surrounds (encapsulates) the PLA and a thread of PLA coated with collagen is formed. See FIG. 29 for a schematic illustration of this set-up. Solutions and electrospinning parameters are shown in Table 3.

TABLE 3

Solutions and electrospinning parameters for co-axial electrospinning

| | Collagen | PLA |
|---|---|---|
| Material | Collagen type 1 powder | PLA (poly lactic acid) |
| Weight Ratio | 10 wt % | 5 wt % |
| Solvents | 1,1,1,3,3,3-hexafluoro-2-propanol | |
| Induced Voltage | 18 kV | |
| Feed Rate | 1 ml/h | |
| Tip to Collect Distance | 13 cm | |

Figure 30A:
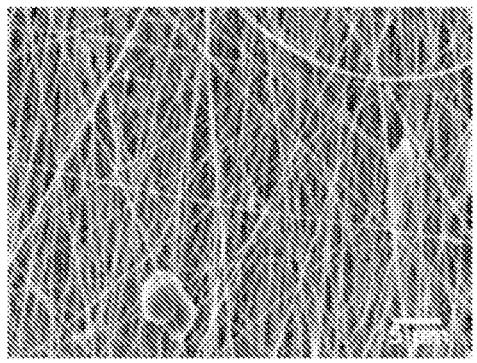
FIG. 30A-D depicts structural morphology of co-axial spun collagen before washing (A) and after washing (C), which dissolves fibers, and co-axial spun collagen crosslinked with 0.25% glutaraldehyde before washing (B) and after washing (D) which does not dissolve fibers.
Figure 30B:
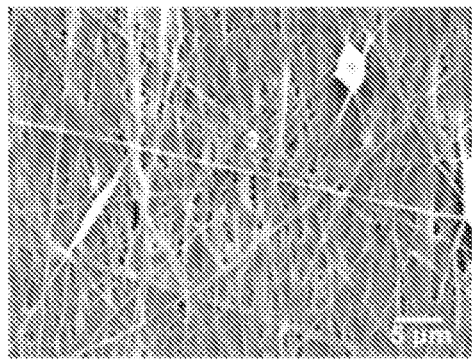
Figure 30C:
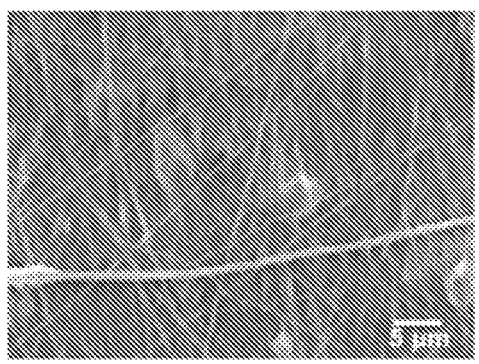
Figure 30D:
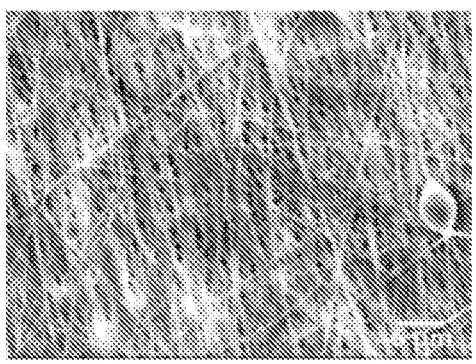
Figure 31:
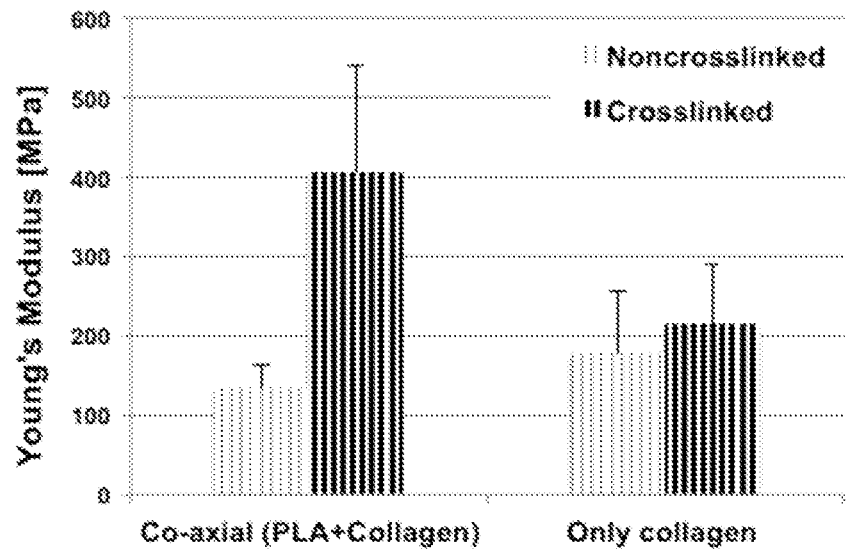
FIG. 31 depicts mechanical properties of co-axial spun PLA-core, collagen-shell fibers compared to electrospun pure collagen fibers, both cross linked and non-crosslinked.
Figure 32A:
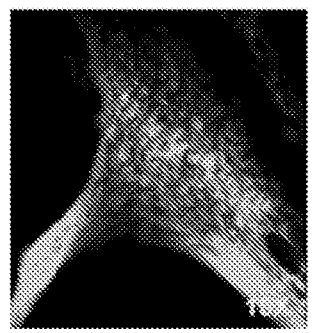
FIG. 32A-D depicts confocal microscopy of calcein AM-stained (live) meniscal avascular cells seeded on non-crosslinked co-axial spun collagen-shell/PLA-core scaffolds one week (A) and two weeks (B) after seeding, as well as cross-linked co-axial spun collagen-shell/PLA-core scaffolds one week (C) and two weeks (D) after seeding.
Figure 32B:
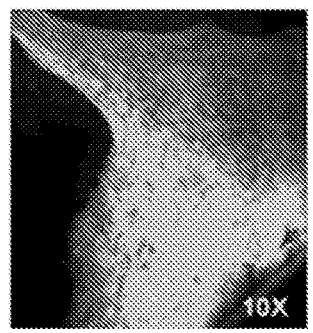
Figure 32C:
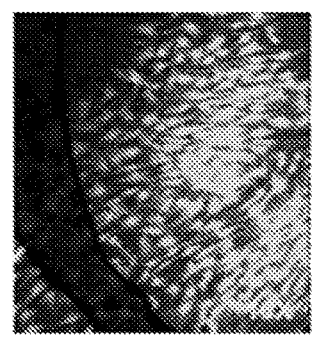
Figure 32D:
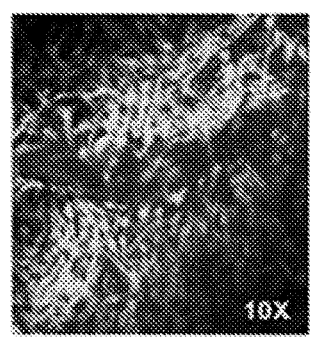
Figure 33A:
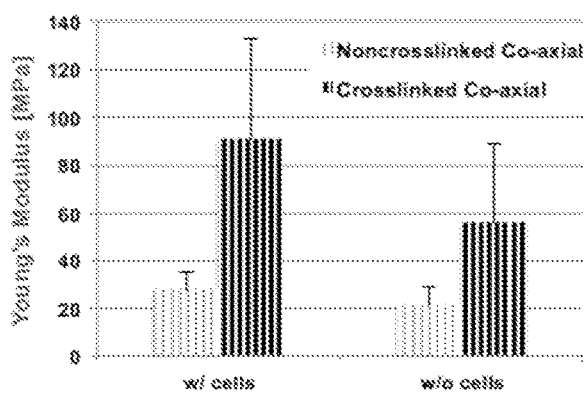
FIG. 33A-B depicts mechanical properties of cell-laden versus non-cellular co-axial spun scaffolds (A) and cell-laden versus non-cellular crosslinked pure collagen scaffolds (B) after 1 week.
Figure 33B:
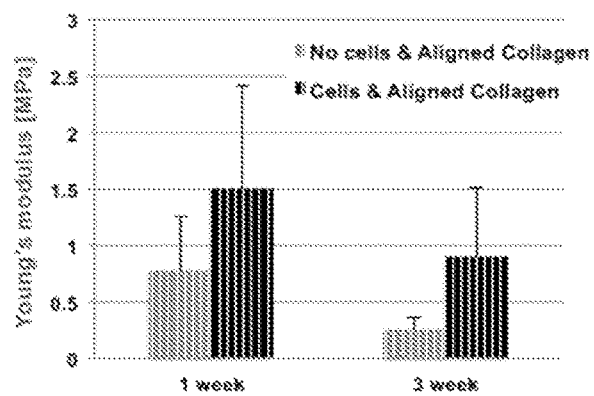

Cells were crosslinked with 0.25% glutaraldehyde and washed once with PBS (FIG. 30D). Scaffolds were dissolved if not cross-linked (FIG. 30C). Young's modulus was measured with an Instron® Universal Testing Machine (3342 Single Column Model), which showed the mechanical property of co-axial scaffolds is higher than collagen only scaffolds, and comparable to Young's modulus of human menisci (circumferential direction: 100-300 MPa, radial direction 10-30 MPa).

Cell viability was assessed with calcein AM for live cells and ethidium homodimer-1 for dead cells using fluorescence confocal microscopy. In the case of non-cross-linked co-axial scaffolds, collagen materials dissolved and were collected on surface of PLA fibers, demonstrating higher compatibility than PLA fibers alone. Cells were distributed evenly on crosslinked co-axial scaffolds (see FIGS. 32A-D). Cell-laden co-axial scaffolds have much higher mechanical property than cell-laden single collagen scaffolds (see FIGS. 33A-B, note y-axis scales).

What is claimed is:

1. A method of producing a meniscal implant, the method comprising:
   a) forming polymer fibers by electrospinning a first polymer solution comprising a first polymer and a second polymer solution comprising a second polymer, the electrospinning comprising:
      i) applying a first voltage to the first polymer solution in a first emitter and ejecting the first polymer solution through a first emitter outlet; and
      ii) applying a second voltage to the second polymer solution in a second emitter and ejecting the second polymer solution through a second emitter outlet,
   wherein the electrospinning the first polymer solution and the second polymer solution occurs simultaneously;
   b) collecting the polymer fibers onto a rotating collector;
   c) electrospraying a plurality of cells onto the rotating collector and the polymer fibers; and
   d) crosslinking the polymer fibers to produce the meniscal implant,
   wherein the electrospinning and the electrospraying occur before the crosslinking,
   wherein the rotating collector comprises a V shape or a custom shape of meniscus,
   wherein the meniscal implant comprises the V shape or the custom shape of meniscus, and wherein the meniscal implant has a Young's modulus of about 100 MPa to about 300 MPa measured in a circumferential direction.

2. The method of claim 1, wherein the first polymer, the second polymer, or both, is selected from the group consisting of: polylactic acid, collagen, methacrylated collagen, and combinations thereof.

3. The method of claim 1, wherein the electrospinning the first polymer solution produces a first plurality of polymer fibers on the rotating collector and wherein the second polymer solution produces a second plurality of polymer fibers on the rotating collector.

4. The method of claim 1, wherein the first emitter outlet comprises a first tube with a first interior and the second emitter outlet comprises a second tube with a second interior, wherein the second tube is within the first interior of the first tube, and the first tube and the second tube are co-axial.

5. The method of claim 4, wherein the first polymer solution encapsulates the second polymer solution as they are ejected from the emitter outlets onto the rotating collector to form the polymer fibers, wherein the polymer fibers have a structure comprising:
   a) a shell comprising the first polymer; and
   b) a core comprising the second polymer.

6. The method of claim 5, wherein the first polymer is selected from the group consisting of: collagen, methacrylated collagen, and both.

7. The method of claim 5, wherein the second polymer is selected from the group consisting of: polylactic acid, polycaprolactone, a copolymer thereof, and a blend thereof.

8. The method of claim 1, further comprising applying a voltage to the rotating collector.

9. The method of claim 1, wherein the electrospinning and the electrospraying occur simultaneously.

10. The method of claim 1, wherein the plurality of cells is selected from the group consisting of: chondrocytes, cartilaginous cells, fibrocartilaginous cells, chondroblasts, meniscal cells, and progenitors thereof.

11. The method of claim 1, wherein the plurality of cells is selected from the group consisting of: mesenchymal stem cells, meniscal cells, chondroblasts, chondrocytes, and a combination thereof.

12. The method of claim 1, further comprising contacting the meniscal implant with a biomimetic gel.

13. The method of claim 1, further comprising producing a plurality of meniscal implants.

14. The method of claim 1, further comprising combining a plurality of the polymer fibers to form a multilayer meniscal implant.

15. The method of claim 1, wherein the crosslinking the polymer fibers comprises photocrosslinking.

16. The method of claim 8, wherein a voltage differential between the voltage applied to the rotating collector and the voltage applied to the first or second polymer ranges from about 10 kV to about 30 kV.

17. A method of producing a meniscal implant, the method comprising:
   a) forming polymer fibers by electrospinning a first polymer solution comprising a first polymer and a second polymer solution comprising a second polymer to form the polymer fibers, the electrospinning comprising:
      i) applying a first voltage to the first polymer solution in a first emitter and ejecting the first polymer solution through a first emitter outlet; and
      ii) applying a second voltage to the second polymer solution in a second emitter and ejecting the second polymer solution through a second emitter outlet,
      wherein the electrospinning the first polymer solution and the second polymer solution occurs simultaneously;
   b) collecting the polymer fibers onto a rotating collector;
   c) crosslinking the polymer fibers to produce the meniscal implant; and
   d) electrospraying a plurality of cells onto the rotating collector and the polymer fibers;
wherein the electrospinning, the crosslinking, and the electrospraying occur simultaneously,
wherein the rotating collector comprises a V shape or a custom shape of meniscus,
wherein the meniscal implant comprises the V shape or the custom shape of meniscus, and
wherein the meniscal implant has a Young's modulus of about 100 MPa to about 300 MPa measured in a circumferential direction.

18. The method of claim 17, wherein the electrospinning the first polymer solution and the second polymer solution comprises co-axial electrospinning, wherein the first polymer solution surrounds the second polymer solution as they are ejected from the emitter outlets onto the rotating collector to form the polymer fibers, wherein the polymer fibers have a structure comprising:
   a) a shell comprising the first polymer; and
   b) a core comprising the second polymer.

19. The method of claim 1, further comprising crosslinking the polymer fibers intermittently.

20. The method of claim 1, further comprising rotating the rotating collector.

21. The method of claim 20, wherein the rotating comprises rotating the rotating collector at a constant speed.

22. The method of claim 20, wherein the rotating collector comprises a drum collector.

23. The method of claim 10, wherein the plurality of cells comprises meniscal cells.

24. The method of claim 20, wherein the rotating comprises rotating the rotating collector at an alternating speed.

* * * * *